United States Patent
Sherman et al.

(10) Patent No.: US 11,008,553 B2
(45) Date of Patent: May 18, 2021

(54) HALOGENATION OF COMPLEX ORGANIC COMPOUNDS

(71) Applicant: THE REGENTS OF THE UNIVERSITY OF MICHIGAN, Ann Arbor, MI (US)

(72) Inventors: David H. Sherman, Ann Arbor, MI (US); Amy E. Fraley, Ann Arbor, MI (US); Ashootosh Tripathi, Ypsilanti, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 0 days.

(21) Appl. No.: 16/516,102

(22) Filed: Jul. 18, 2019

(65) Prior Publication Data

US 2020/0048617 A1    Feb. 13, 2020

Related U.S. Application Data

(60) Provisional application No. 62/700,152, filed on Jul. 18, 2018.

(51) Int. Cl.
*C12P 5/00* (2006.01)
*C12N 9/02* (2006.01)
*A61K 31/4995* (2006.01)
*C12P 17/18* (2006.01)

(52) U.S. Cl.
CPC ........ *C12N 9/0071* (2013.01); *A61K 31/4995* (2013.01); *C12P 17/182* (2013.01)

(58) Field of Classification Search
CPC .............................................. C12Y 114/14009
See application file for complete search history.

(56) References Cited

U.S. PATENT DOCUMENTS

2015/0044735 A1* 2/2015 Li .......................... C12N 9/93
                                                      435/119

OTHER PUBLICATIONS

Adams et al., "PHENIX: a comprehensive Python-based system for macromolecular structure solution," Biol. Crystallogr. 66:213-221 (2010).
Andorfer et al., "Directed evolution of RebH for catalyst-controlled halogenation of indole C—H bonds," Chem. Sci. 7:3720-3729 (2016).
Barone et al., "Quantum Calculation of Molecular Energies and Energy Gradients in Solution by a Conductor Solvent Model," J. Phys. Chem. A. 102:1995-2001 (1998).
Bayly et al., "A Well-Behaved Electrostatic Potential Based Method Using Charge Restraints for Deriving Atomic Charges: The RESP Model," J. Phys. Chem. 97:10269-10280 (1993).
Besler et al., "Atomic Charges Derived from Semiempirical Methods," J. Comput. Chem. 11:431-439 (1990).
Buedenbender et al., "Structure and Action of the Myxobacterial Chondrochloren Halogenase CndH: A New Variant of FAD-dependent Halogenases," J. Mol. Biol. 385(2):520-530 (2009).
Cacho et al., "Complexity Generation in Fungal Polyketide Biosynthesis: A Spirocycle-Forming P450 in the Concise Pathway to the Antifungal Drug Griseofulvin," ACS Chem. Biol. 8:2322-2330 (2013).
Chakraborty et al., "Studies on the Mechanism of p-Hydroxyphenylacetate 3-Hydroxylase from Pseudomonas aeruginosa—a System Composed of a Small Flavin Reductase and a Large Flavin-Dependent Oxygenase," Biochemistry 49(2):372-385 (2010).
Chankhamjon et al., "Biosynthesis of the Halogenated Mycotoxin Aspirochlorine in Koji Mold Involves a Cryptic Amino Acid Conversion," Angew. Chem. Int. Ed. 53:13409-13413 (2014).
Chankhamjon et al., "Regioselective Dichlorination of a Non-Activated Aliphatic Carbon Atom and Phenolic Bismethylation by a Multifunctional Fungal Flavoenzyme," Angew. Chem. Int. Ed. 55:11955-11959 (2016).
Chung et al., "Stereoselective Halogenation in Natural Product Synthesis," Angew. Chem. Int. Ed. 55:4396-4434 (2016).
Cossi et al., "Energies, Structures, and Electronic Properties of Molecules in Solution with the C-PCM Solvation Model," J. Comp. Chem. 24:669-681 (2003).
Darden et al., "Particle mesh Ewald: An N log(N) method for Ewald sums in large systems," J. Chem. Phys. 98:10089-10092 (1993).
Ding et al.,"Premalbrancheamide: Synthesis, Isotopic Labeling, Biosynthetic Incorporation, and Detection in Cultures of Malbranchea aurantiaca," Org. Lett. 10(21):4863-4866 (2008).
Dong et al., "Tryptophan 7-Halogenase (Prna) Structure Suggests a Mechanism for Regioselective Chlorination," Science 309:2216-2219 (2005).
Dorrestein et al., "Dichlorination of a pyrrolyl-S-carrier protein by FADH2-dependent halogenase PltA during pyoluteorin biosynthesis," Proc. Natl. Acad. Sci. 102(39):13843-13848 (2005).
El Gamal et al., "Biosynthesis of coral settlement cue tetrabromopyrrole in marine bacteria by a uniquely adapted brominase-thioesterase enzyme pair," Proc. Natl. Acad. Sci. 113(14):3797-3802 (2016).
Emsley et al., "Coot: model-building tools for molecular graphics," Biol. Crystallogr. 60:2126-2132 (2004).
Ferrara et al., "Identification of a Halogenase Involved in the Biosynthesis of Ochratoxin A in Aspergillus carbonarius," Appl. Environ. Microbiol. 82(18):5631-5641 (2016).
Figueroa et al., "Fluorescence, circular dichroism, NMR, and docking studies of the interaction of the alkaloid malbracheamide with calmodulin," J. Enzyme Inhib. Med. Chem. 26(3): 378-385 (2011).
Finefield et al., "Fungal Origins of the Bicyclo[2.2.2]diazaoctane Ring System of Prenylated Indole Alkaloids," J. Nat. Prod. 75:812-833 (2012).

(Continued)

*Primary Examiner* — Tekchand Saidha
(74) *Attorney, Agent, or Firm* — Marshall, Gerstein & Borun LLP

(57) ABSTRACT

The disclosure provides biocatalysts that halogenate complex chemical compounds in specific and predictable ways. Also disclosed are halogenated complex organic compounds. The disclosure further provides methods for the halogenation of complex chemical compounds and methods of inhibiting the contraction of smooth muscle in mammals.

19 Claims, 21 Drawing Sheets

Specification includes a Sequence Listing.

(56) References Cited

OTHER PUBLICATIONS

Fraley et al., "Function and structure of MalA/MalA', iterative halogenases for late-stage C—H functionalization of indole alkaloids," J Am Chem Soc. 139(34):12060-12068 (2017).
Glenn et al., "Reengineering a Tryptophan Halogenase to Preferentially Chlorinate a Direct Alkaloid Precursor," J. Am. Chem. Soc. 133:19346-19349 (2011).
Gutekunst et al., "C—H functionalization logic in total synthesis," Chem. Soc. Rev. 40:1976-1991 (2011).
Hillwig et al., "A new family of iron-dependent halogenases acts on freestanding substrates," Nat. Chem. Biol. 10:921-923 (2014).
International Search Report and Written Opinion from International Application No. PCT/US2019/042469 dated Dec. 2, 2019.
Jorgensen et al., "Comparison of simple potential functions for simulating liquid water," J. Chem. Phys. 79:926-935 (1983).
Kabsch, "XDS," Acta. Cryst. D66:125-132 (2010).
Klas et al., "Natural Diels—Alderases: Elusive and Irresistable," J. Org. Chem. 80:11672-11685 (2015).
Lang et al, "Changing the Regioselectivity of the Tryptophan 7-Halogenase PrnA by Site-Directed Mutagenesis," Angew. Chem. Int. Ed. 50:2951-2953 (2011).
Laws, "Total Synthesis of (+)-Malbrancheamide B Utilizing a Stereoselective Domino Reaction Sequence to Establish the Bicyclo{2.2] diazaoctane Core," Dissertations, Theses, and Masters Projects (2013).
Li et al., "Comparative analysis of the biosynthetic systems for fungal bicyclo[2.2.2] diazaoctane indole alkaloids: the (+)/(−)-notoamide, paraherquamide and malbrancheamide pathways," Med. Chem. Commun. 3:987-996 (2012).
Li et al., "On the Dielectric "Constant" of Proteins: Smooth Dielectric Function for Macromolecular Modeling and Its Implementation in DelPhi," J. Chem. Theory Comp. 9:2126-2136 (2013).
Madariaga-Mazón et al., "Insights on the vasorelaxant mode of action of malbrancheamide," J. Pharm. Pharmacol. 67(4):551-558 (2015).
Martínez-Luis et al., "Malbrancheamide, a new calmodulin inhibitor from the fungus *Malbranchea aurantiaca*," Tetrahedron. 62:1817-1822 (2006).
Menon et al., "RadH: A Versatile Halogenase for Integration into Synthetic Pathways," Angew. Chem. Int. Ed. 56:11841-11845 (2017).
Neumann et al., "A flavin-dependent halogenase catalyzes the chlorination step in the biosynthesis of Dictyostelium differentiation-inducing factor 1," Proc. Natl. Acad. Sci. 107(13):5798-803 (2010).
Nielsen et al., "Heterologous Reconstitution of the Intact Geodin Gene Cluster in Aspergillus nidulans through a Simple and Versatile PCR Based Approach," PLoS One. 8(8)e72871:1-10 (2013).
Olsson et al., "PROPKA3: consistent treatment of internal and surface residues in empirical pKa predictions," J. Chem. Theory Comput. 7(2):525-537 (2011).
Payne et al., "Directed Evolution of RebH for Site Selective Halogenation of Large, Biologically Active Molecules," Angew. Chem. Int. Ed. 54:4226-4230 (2015).
Payne et al., "Regio-Selective Arene Halogenation Using the FAD-Dependent Halogenase RebH," Angew. Chem. Int. Ed. 52:5271-5274 (2013).
Podzelinska et al., "Chloramphenicol Biosynthesis: The Structure of CmlS, a Flavin-Dependent Halogenase Showing a Covalent Flavin-Aspartate Bond," J. Mol. Biol. 397:316-331 (2010).
Salomon-Ferrer et al., "Routine Microsecond Molecular Dynamics Simulations with AMBER on GPUs. 2. Explicit Solvent Particle Mesh Ewald," J. Chem. Theory Comput. 9:3878-3888 (2013).
Sato et al., "Combinatorial Generation of Chemical Diversity by Redox Enzymes in Chaetoviridin Biosynthesis," Org. Lett. 18:1446-1449 (2016).
Schutz et al., "What Are the Dielectric "Constants" of Proteins and How to Validate Electrostatic Models?" Proteins: Struct. Funct. Bioinf. 44:400-417 (2001).
Seibold et al., "A flavin-dependent tryptophan 6-halogenase and its use in modification of pyrrolnitrin biosynthesis," Biocatal. Biotransform. 24(6):401-408 (2006).
Shepherd et al., "A Structure-Guided Switch in the Regioselectivity of a Tryptophan Halogenase," ChemBioChem. 17:821-824 (2016).
Shepherd et al., "Extending the biocatalytic scope of regiocomplementary flavin-dependent halogenase enzymes," J. Chem. Sci. 6:3454-3460 (2015).
Simon et al., "How reliable are DFT transition structures? Comparison of GGA, hybrid-meta-GGA and meta-GGA functionals," Org. Biomol. Chem. 9:689-700 (2011).
Singh et al., "An Approach to Computing Electrostatic Charges for Molecules," J. Comput. Chem. 5:129-145 (1984).
Sondergaard et al., "Improved Treatment of Ligands and Coupling Effects in Empirical Calculation and Rationalization nof pKa Values," J. Chem. Theory Comput. 7(7):2284-2295 (2011).
Stocking et al., "Chemistry and Biology of Biosynthetic Diels-Alder Reactions," Angew. Chem. Int. Ed. 42:3078-3115 (2003).
Stols et al., "A New Vector for High-Throughput, Ligation-Independent Cloning Encoding a Tobacco Etch Virus Protease Cleavage Site," Protein Expression and Purification. 25:8-15 (2002).
Wang et al., "Development and Testing of a General Amber Force Field," J. Comput. Chem. 25:1157-1174 (2004).
Wang et al., "How Well Does a Restrained Electrostatic Potential (RESP) Model Perform in Calculating Conformational Energies of Organic and Biological Molecules," J. Comput. Chem. 21:1049-1074 (2000).
Watts et al., "Utilizing DART Mass Spectrometry to Pinpoint Halogenated Metabolites from a Marine Invertebrate-Derived Fungus," J. Org. Chem. 76(15):6201-6208 (2011).
Weichold et al., "Specific Enzymatic Halogenation—From the Discovery of Halogenated Enzymes to Their Applications In Vitro and in Vivo," Angew. Chem. Int. Ed. 55:6375-6389(2016).
Yeh et al., "Chlorination by a Long-Lived Intermediate in the Mechanism of Flavin-Dependent Halogenases," Biochemistry 46(5):1284-1292 (2007).
Yeh et al., "Robust in vitro activity of RebF and RebH, a two-component reductase/halogenase, generating 7-chlorotryptophan during rebeccamycin biosynthesis," Proc. Natl. Acad. Sci. 102(11):3960-3965 (2005).
Zehner et al., "A Regioselective Tryptophan 5-Halogenase Is Involved in Pyrroindomycin Biosynthesis in *Streptomyces rugosporus* LL-42D005," Chem. Biol. 12:445-452 (2005).
Zeng et al., "A Novel Fungal Flavin-Dependent Halogenase for Natural Product Biosynthesis," J. ChemBioChem. 11: 2119-2123 (2010).
Zeng et al., "Characterization of a tryptophan 6-halogenase from *Streptomyces toxytricini*," J. Biotechnol. Lett. 33:1607-1613 (2011).
Zhao et al., "The M06 suite of density functionals for main group thermochemistry, thermochemical kinetics, noncovalent interactions, excited states, and transition elements: two new functionals and systematic testing of four M06-class functioanls and 12 other functions," Theor. Chem. Acc. 120:215-241 (2008).

* cited by examiner

SEQUENCE LISTING

<160> NUMBER OF SEQ ID NOS: 39

<210> SEQ ID NO 1
<211> LENGTH: 2004
<212> TYPE: DNA
<213> ORGANISM: Malbranchea aurantiaca
<220> FEATURE:
<221> NAME/KEY: misc_feature
<223> OTHER INFORMATION: Wild-type MalA coding region

<400> SEQUENCE: 1

```
atggcgccga caccaaagta tacgtttacc gagagggctg cggcaggcaa tctcagcgac      60
gctgagattc tcaactccaa taatcctact ggatctgagc tcccagatga atcggatgtg     120
gtggtgggcg gtgctggtat ccatggtctg atctatgccc ttcacgcttc aaagtataaa     180
ccgaacaacc tcaagatctc cgttattgag aagaacacta ggcctggtta caagattggc     240
gagagcactc tacctatctt ttacacctgg tgcaaactcc acggcatctc cgcggcatac     300
ctccttcgac tattcggact caaggatggg ctgtgctttt actttcttga tcgagagaac     360
caggggcagt acacagactt ctgcagtgtt ggggctccag gtttggtatt agccagttta     420
cagattgagc ggccaatgag cgagctgctc tttacaattc ttgcgcaacg aaatggagtc     480
aatgtctatc acggccggga ggtggatttt aaaagcacgg tggtccaagg gggtggccag     540
ggcaacaaga tcgcagtctc ccggggcaaa tatgatagca cacccaagac aatagattca     600
gccctcttcg ttgacgcaac aggccgcttc cgccaatttt gctccaagaa agcccccga      660 caccgattcg atggatggaa ctgcaacgcc ttctggggtt atttcactgc cccaaaggat     720
gagagcaaga ttcctttga tctctatgaa ggtgatcaca caaccacct gtgttttccg      780 gaaggttggg tctgggttat tcgtctaccc tcttgggaag ggagcctcat agcgaacttg     840
atggatatgg tgacatacat actcgaatgc gctgacgccg gagtacctgg tgatgaactc     900
ccgagttctg aagagcttgc caggatgttt gggctcaagt ttcagtgggt gacaagtatt     960
ggctttgccg tgcgcaatga tgtcaagtac ccggaagatc tctcagccta tgggacccgt    1020
gaggcagagc aaaaattcaa ctactttgtt cagaagtatg agctgcttca gcagttcatg    1080
tcaaactttg agcttattga aaatctttat ggccctggga ccacatggtt catccgtaag    1140
acgctggcat accagtctcc agtggtttct ggacctggct ggcttgccat tggtgatgcc    1200
tgtggtttca ccaacccgct ctattctccg gggattaatg ttggcatgtc gacttcaaca    1260
tgggccgcac agctttcgca ccgaattgtg gagattggga aaagtgcgcc tgcagatgcg    1320
gcggagtcct ctattcgaaa attactggtc ccatatgacg attattgcaa gtccctagtt    1380
ccggcactcg agcaaatgaa tcgatttaac tacgtctgtt atcgcgatac acgtttaggt    1440
ccccaggtgg catgcctctg gcagttttc gctggcatag agcgatattt gtcagatgtt    1500
aacattgaaa ccttcgcaca ttacgcgatt aaatgggttt ggggagccat ggtgcctgaa    1560
tatcaacaag tcgcacagaa atgcattgag catatcgaaa ccgtccccct cgatgagcga    1620
cttcccgatg cgatggttga tgagttgctt gcgttttcga accgaattaa aagtgctgcc    1680
gtggccgcag acgacttcag tctccggtgg gatgcgatcc tgcgctcttt cgatcggtct    1740
ttgaatttcg tcgaagggaa gacaagcagg gacatctata cgagacaatg ctcgggttgc    1800
```

-continued

```
gggcatggc tccaactccg cccagattgg aaaaagtgcc actcatgcgg tcttctgggc    1860
accgagccgc aaacggccgt tacctttgat cccccgctga ccgcagaaga agaagcgtta    1920
ctttacgctg cctggaatac tgcgcctaaa tacgacccct cgaaggagtt aaagctacca    1980 accctacca ggccagctgc atag                                            2004
```

<210> SEQ ID NO 2
<211> LENGTH: 667
<212> TYPE: PRT
<213> ORGANISM: Malbranchea aurantiaca
<220> FEATURE:
<221> NAME/KEY: MISC_FEATURE
<223> OTHER INFORMATION: Wild-type MalA protein

<400> SEQUENCE: 2

```
Met Ala Pro Thr Pro Lys Tyr Thr Phe Thr Glu Arg Ala Ala Gly
1               5                   10                  15

Asn Leu Ser Asp Ala Glu Ile Leu Asn Ser Asn Asn Pro Thr Gly Ser
            20                  25                  30

Glu Leu Pro Asp Glu Ser Asp Val Val Gly Gly Ala Gly Ile His
        35                  40                  45

Gly Leu Ile Tyr Ala Leu His Ala Ser Lys Tyr Lys Pro Asn Asn Leu
    50                  55                  60

Lys Ile Ser Val Ile Glu Lys Asn Thr Arg Pro Gly Tyr Lys Ile Gly
65                  70                  75                  80

Glu Ser Thr Leu Pro Ile Phe Tyr Thr Trp Cys Lys Leu His Gly Ile
                85                  90                  95

Ser Ala Ala Tyr Leu Leu Arg Leu Phe Gly Leu Lys Asp Gly Leu Cys
            100                 105                 110

Phe Tyr Phe Leu Asp Arg Glu Asn Gln Gly Gln Tyr Thr Asp Phe Cys
        115                 120                 125

Ser Val Gly Ala Pro Gly Leu Val Leu Ala Ser Leu Gln Ile Glu Arg
    130                 135                 140

Pro Met Ser Glu Leu Leu Phe Thr Ile Leu Ala Gln Arg Asn Gly Val
145                 150                 155                 160

Asn Val Tyr His Gly Arg Glu Val Asp Phe Lys Ser Thr Val Val Gln
                165                 170                 175

Gly Gly Gly Gln Gly Asn Lys Ile Ala Val Ser Arg Gly Lys Tyr Asp
            180                 185                 190

Ser Thr Pro Lys Thr Ile Asp Ser Ala Leu Phe Val Asp Ala Thr Gly
        195                 200                 205

Arg Phe Arg Gln Phe Cys Ser Lys Lys Ala Pro Arg His Arg Phe Asp
    210                 215                 220

Gly Trp Asn Cys Asn Ala Phe Trp Gly Tyr Phe Thr Ala Pro Lys Asp
225                 230                 235                 240

Glu Ser Lys Ile Pro Phe Asp Leu Tyr Glu Gly Asp His Thr Asn His
                245                 250                 255

Leu Cys Phe Pro Glu Gly Trp Val Trp Val Ile Arg Leu Pro Ser Trp
            260                 265                 270

Glu Gly Ser Leu Ile Ala Asn Leu Met Asp Met Val Thr Tyr Ile Leu
        275                 280                 285

Glu Cys Ala Asp Ala Gly Val Pro Gly Asp Glu Leu Pro Ser Ser Glu
    290                 295                 300

Glu Leu Ala Arg Met Phe Gly Leu Lys Phe Gln Trp Val Thr Ser Ile
305                 310                 315                 320
```

```
Gly Phe Ala Val Arg Asn Asp Val Lys Tyr Pro Glu Asp Leu Ser Ala
                325                 330                 335

Tyr Gly Thr Arg Glu Ala Glu Gln Lys Phe Asn Tyr Phe Val Gln Lys
            340                 345                 350

Tyr Glu Leu Leu Gln Gln Phe Met Ser Asn Phe Glu Leu Ile Glu Asn
        355                 360                 365

Leu Tyr Gly Pro Gly Thr Thr Trp Phe Ile Arg Lys Thr Leu Ala Tyr
    370                 375                 380

Gln Ser Pro Val Val Ser Gly Pro Gly Trp Leu Ala Ile Gly Asp Ala
385                 390                 395                 400

Cys Gly Phe Thr Asn Pro Leu Tyr Ser Pro Gly Ile Asn Val Gly Met
                405                 410                 415

Ser Thr Ser Thr Trp Ala Ala Gln Leu Ser His Arg Ile Val Glu Ile
                420                 425                 430

Gly Lys Ser Ala Pro Ala Asp Ala Ala Glu Ser Ser Ile Arg Lys Leu
            435                 440                 445

Leu Val Pro Tyr Asp Asp Tyr Cys Lys Ser Leu Val Pro Ala Leu Glu
    450                 455                 460

Gln Met Asn Arg Phe Asn Tyr Val Cys Tyr Arg Asp Thr Arg Leu Gly
465                 470                 475                 480

Pro Gln Val Ala Cys Leu Trp Gln Phe Ala Gly Ile Glu Arg Tyr
                485                 490                 495

Leu Ser Asp Val Asn Ile Glu Thr Phe Ala His Tyr Ala Ile Lys Trp
                500                 505                 510

Val Trp Gly Ala Met Val Pro Glu Tyr Gln Gln Val Ala Gln Lys Cys
            515                 520                 525

Ile Glu His Ile Glu Thr Val Pro Leu Asp Glu Arg Leu Pro Asp Ala
        530                 535                 540

Met Val Asp Glu Leu Leu Ala Phe Ser Asn Arg Ile Lys Ser Ala Ala
545                 550                 555                 560

Val Ala Ala Asp Asp Phe Ser Leu Arg Trp Asp Ala Ile Leu Arg Ser
                565                 570                 575

Phe Asp Arg Ser Leu Asn Phe Val Glu Gly Lys Thr Ser Arg Asp Ile
                580                 585                 590

Tyr Thr Arg Gln Cys Ser Gly Cys Gly Ala Trp Leu Gln Leu Arg Pro
            595                 600                 605

Asp Trp Lys Lys Cys His Ser Cys Gly Leu Leu Gly Thr Glu Pro Gln
        610                 615                 620

Thr Ala Val Thr Phe Asp Pro Pro Leu Thr Ala Glu Glu Ala Leu
625                 630                 635                 640

Leu Tyr Ala Ala Trp Asn Thr Ala Pro Lys Tyr Asp Pro Ser Lys Glu
                645                 650                 655

Leu Lys Leu Pro Thr Pro Thr Arg Pro Ala Ala
            660                 665

<210> SEQ ID NO 3
<211> LENGTH: 2004
<212> TYPE: DNA
<213> ORGANISM: Malbranchea graminicola
<220> FEATURE:
<221> NAME/KEY: misc_feature
<223> OTHER INFORMATION: Wild-type MalA' coding region
```

<400> SEQUENCE: 3

```
atggcgccga caccaaagta tacgtttacc gagagggctg cggcaggcaa tctcagcgac      60
gctgagattc tcaactccaa taatcctact ggatctgagc tcccagatga atcggatgtg     120
gtggtgggcg gtgctggtat ccatggtctg atctatgccc ttcacgcttc aaagtataaa     180
ccgaacaacc tcaagatctc cgttattgag aagaacacta ggcctggtta caagattggc     240
gagagcactc tacctatctt ttacacctgg tgcaaactcc acggcatctc cgcggcatac     300
ctccttcgac tattcggact caaggatggg ctgtgctttt actttcttga tcgagagaac     360
caggggcagt acacagactt ctgcagtgtt ggggctccag gtttggtatt agccagttta     420
cagattgagc ggccaatgag cgagctgctc tttacaattc ttgcgcaacg aaatggagtc     480
aatgtctatc acggccggga ggtggatttt aaaagcacgg tggtccaagg gggtggccag     540
ggcaacaaga tcgcagtctc ccggggcaaa tatgatagca cacccaagac aatagattca     600
gccctcttcg ttgacgcaac aggccgcttc cgccaatttt gctccaagaa agcccccga      660
caccgattcg atggatggaa ctgcaacgcc ttctggggtt atttcactgc ccaaaggat     720
gagagcaaga ttcccttttga tctctatgaa ggtgatcaca caaaccacct gtgttttccg     780
gaaggttggg tctgggttat tcgtctaccc tcttgggaag ggagcccat agcgaacttg     840
atggatatgg tgacatacat actcgaatgc gctgacgccg agtacctggt gatgaactc      900
ccgagttctg aagagcttgc caggatgttt gggctcaagt ttcagtgggt gacaagtatt     960
ggctttgccg tgcgcaatga tgtcaagtac ccggaagatc tctcagccta tgggacccgt    1020
gaggcagagc aaaaattcaa ctactttgtt cagaagtatg agctgcttca gcagttcatg    1080
tcaaactttg agcttattga aaatctttat ggccctggga ccacatggtt catccgtaag    1140
acgctggcat accagtctcc agtggtttct ggacctggct ggcttgccat tggtgatgcc    1200
tgtggtttca ccaacccgct ctattctccg gggattaatg ttggcatgtc gacttcaaca    1260
tgggccgcac agctttcgca cccgattgtg gagattggga aaagtgcgcc tgcagatgcg    1320
gcggagtcct ctattcgaaa attactggtc ccatatgacg attattgcaa gtccctagtt    1380
ccggcactcg agcaaatgaa tcgatttaac tacgtctgtt atcgcgatac acgtttaggt    1440
ccccaggtgg catgcctctg gcagttttc gctggcatag agcgatattt gtcagatgtt    1500
aacattgaaa ccttcgcaca ttacgcgatt aaatgggttt gggagccat ggtgcctgaa     1560
tatcaacaag tcgcacagaa atgcattgag catatcgaaa ccgtccccct cgatgagcga    1620
cttcccgatg cgatggttga tgagttgctt gcgttttcga accgaattaa aagtgctgcc    1680
gtggccgcag acgacttcag tctccggtgg gatgcgatcc tgcgctcttt cgatcggtct    1740
ttgaatttcg tcgaagggaa gacaagcagg gacatctata cgagacaatg ctcgggttgc    1800
ggggcatggc tccaactccg cccagattgg aaaaagtgcc actcatgcgg tcttctgggc    1860
accgagccga aaacggccgt tacctttgat ccccgctga ccgcagaaga gaagcgtta     1920
ctttacgctg cctggaatac tgcgcctaaa tacgaccct cgaaggagtt aaagctacca     1980
acccctacca ggccagctgc atag                                           2004
```

<210> SEQ ID NO 4
<211> LENGTH: 667
<212> TYPE: PRT
<213> ORGANISM: Malbranchea graminicola
<220> FEATURE:
<221> NAME/KEY: MISC_FEATURE
<223> OTHER INFORMATION: Wild-type MalA' protein

<400> SEQUENCE: 4

```
Met Ala Pro Thr Pro Lys Tyr Thr Phe Thr Glu Arg Ala Ala Gly
1               5                   10                  15

Asn Leu Ser Asp Ala Glu Ile Leu Asn Ser Asn Asn Pro Thr Gly Ser
            20                  25                  30

Glu Leu Pro Asp Glu Ser Asp Val Val Gly Ala Gly Ile His
            35                  40                  45

Gly Leu Ile Tyr Ala Leu His Ala Ser Lys Tyr Lys Pro Asn Asn Leu
50                  55                  60

Lys Ile Ser Val Ile Glu Lys Asn Thr Arg Pro Gly Tyr Lys Ile Gly
65                  70                  75                  80

Glu Ser Thr Leu Pro Ile Phe Tyr Thr Trp Cys Lys Leu His Gly Ile
                85                  90                  95

Ser Ala Ala Tyr Leu Leu Arg Leu Phe Gly Leu Lys Asp Gly Leu Cys
                100                 105                 110

Phe Tyr Phe Leu Asp Arg Glu Asn Gln Gly Gln Tyr Thr Asp Phe Cys
            115                 120                 125

Ser Val Gly Ala Pro Gly Leu Val Leu Ala Ser Leu Gln Ile Glu Arg
130                 135                 140

Pro Met Ser Glu Leu Leu Phe Thr Ile Leu Ala Gln Arg Asn Gly Val
145                 150                 155                 160

Asn Val Tyr His Gly Arg Glu Val Asp Phe Lys Ser Thr Val Val Gln
                165                 170                 175

Gly Gly Gly Gln Gly Asn Lys Ile Ala Val Ser Arg Gly Lys Tyr Asp
            180                 185                 190

Ser Thr Pro Lys Thr Ile Asp Ser Ala Leu Phe Val Asp Ala Thr Gly
            195                 200                 205

Arg Phe Arg Gln Phe Cys Ser Lys Lys Ala Pro Arg His Arg Phe Asp
210                 215                 220

Gly Trp Asn Cys Asn Ala Phe Trp Gly Tyr Phe Thr Ala Pro Lys Asp
225                 230                 235                 240

Glu Ser Lys Ile Pro Phe Asp Leu Tyr Glu Gly Asp His Thr Asn His
                245                 250                 255

Leu Cys Phe Pro Glu Gly Trp Val Trp Val Ile Arg Leu Pro Ser Trp
            260                 265                 270

Glu Gly Ser Pro Ile Ala Asn Leu Met Asp Met Val Thr Tyr Ile Leu
            275                 280                 285

Glu Cys Ala Asp Ala Gly Val Pro Gly Asp Glu Leu Pro Ser Ser Glu
290                 295                 300

Glu Leu Ala Arg Met Phe Gly Leu Lys Phe Gln Trp Val Thr Ser Ile
305                 310                 315                 320

Gly Phe Ala Val Arg Asn Asp Val Lys Tyr Pro Glu Asp Leu Ser Ala
                325                 330                 335

Tyr Gly Thr Arg Glu Ala Glu Gln Lys Phe Asn Tyr Phe Val Gln Lys
            340                 345                 350

Tyr Glu Leu Leu Gln Gln Phe Met Ser Asn Phe Glu Leu Ile Glu Asn
            355                 360                 365

Leu Tyr Gly Pro Gly Thr Thr Trp Phe Ile Arg Lys Thr Leu Ala Tyr
        370                 375                 380

Gln Ser Pro Val Val Ser Gly Pro Gly Trp Leu Ala Ile Gly Asp Ala
385                 390                 395                 400

Cys Gly Phe Thr Asn Pro Leu Tyr Ser Pro Gly Ile Asn Val Gly Met
                405                 410                 415
```

```
Ser Thr Ser Thr Trp Ala Ala Gln Leu Ser His Pro Ile Val Glu Ile
            420                 425                 430
Gly Lys Ser Ala Pro Ala Asp Ala Ala Glu Ser Ser Ile Arg Lys Leu
        435                 440                 445
Leu Val Pro Tyr Asp Asp Tyr Cys Lys Ser Leu Val Pro Ala Leu Glu
    450                 455                 460
Gln Met Asn Arg Phe Asn Tyr Val Cys Tyr Arg Asp Thr Arg Leu Gly
465                 470                 475                 480
Pro Gln Val Ala Cys Leu Trp Gln Phe Phe Ala Gly Ile Glu Arg Tyr
                485                 490                 495
Leu Ser Asp Val Asn Ile Glu Thr Phe Ala His Tyr Ala Ile Lys Trp
            500                 505                 510
Val Trp Gly Ala Met Val Pro Glu Tyr Gln Gln Val Ala Gln Lys Cys
        515                 520                 525
Ile Glu His Ile Glu Thr Val Pro Leu Asp Glu Arg Leu Pro Asp Ala
    530                 535                 540
Met Val Asp Glu Leu Leu Ala Phe Ser Asn Arg Ile Lys Ser Ala Ala
545                 550                 555                 560
Val Ala Ala Asp Asp Phe Ser Leu Arg Trp Asp Ala Ile Leu Arg Ser
                565                 570                 575
Phe Asp Arg Ser Leu Asn Phe Val Glu Gly Lys Thr Ser Arg Asp Ile
            580                 585                 590
Tyr Thr Arg Gln Cys Ser Gly Cys Gly Ala Trp Leu Gln Leu Arg Pro
        595                 600                 605
Asp Trp Lys Lys Cys His Ser Cys Gly Leu Leu Gly Thr Glu Pro Gln
610                 615                 620
Thr Ala Val Thr Phe Asp Pro Pro Leu Thr Ala Glu Glu Ala Leu
625                 630                 635                 640
Leu Tyr Ala Ala Trp Asn Thr Ala Pro Lys Tyr Asp Pro Ser Lys Glu
                645                 650                 655
Leu Lys Leu Pro Thr Pro Thr Arg Pro Ala Ala
            660                 665

<210> SEQ ID NO 5
<211> LENGTH: 2004
<212> TYPE: DNA
<213> ORGANISM: Malbranchea aurantiaca
<220> FEATURE:
<221> NAME/KEY: misc_feature
<223> OTHER INFORMATION: MalA (S129A) coding region
<220> FEATURE:
<221> NAME/KEY: misc_feature
<223> OTHER INFORMATION: MalA (S129A) codon variant

<400> SEQUENCE: 5
atggcgccga caccaaagta tacgtttacc gagagggctg cggcaggcaa tctcagcgac      60
gctgagattc tcaactccaa taatcctact ggatctgagc tcccagatga atcgatgtg     120 gtggtgggcg gtgctggtat ccatggtctg atctatgccc tcacgcttc aaagtataaa     180 ccgaacaacc tcaagatctc cgttattgag aagaacacta ggcctggtta caagattggc     240
gagagcactc tacctatctt ttacacctgg tgcaaactcc acggcatctc cgcggcatac     300
ctccttcgac tattcggact caaggatggg ctgtgctttt actttcttga tcgagagaac     360
caggggcagt acacagactt ctgcgcggtt ggggctccag gtttggtatt agccagttta     420
cagattgagc ggccaatgag cgagctgctc tttacaattc ttgcgcaacg aaatggagtc     480
aatgtctatc acggccggga ggtggatttt aaaagcacgg tggtccaagg gggtggccag     540
```

```
ggcaacaaga tcgcagtctc ccggggcaaa tatgatagca cacccaagac aatagattca    600
gccctcttcg ttgacgcaac aggccgcttc cgccaatttt gctccaagaa agccccccga    660
caccgattcg atggatggaa ctgcaacgcc ttctggggtt atttcactgc cccaaaggat    720
gagagcaaga ttcccttga tctctatgaa ggtgatcaca caaaccacct gtgttttccg     780
gaaggttggg tctgggttat cgtctaccc tcttgggaag ggagcctcat agcgaacttg     840
atggatatgg tgcatacat actcgaatgc gctgacgccg gagtacctgg tgatgaactc     900
ccgagttctg aagagcttgc caggatgttt gggctcaagt ttcagtgggt gacaagtatt    960
ggctttgccg tgcgcaatga tgtcaagtac ccggaagatc tctcagccta tgggaccccgt  1020 gaggcagagc aaaaattcaa ctactttgtt cagaagtatg agctgcttca gcagttcatg    1080
tcaaactttg agcttattga aaatctttat ggccctggga ccacatggtt catccgtaag    1140
acgctggcat accagtctcc agtggtttct ggacctggct ggcttgccat tggtgatgcc    1200
tgtggtttca ccaacccgct ctattctccg gggattaatg ttggcatgtc gacttcaaca    1260
tgggccgcac agctttcgca ccgaattgtg agattggga aagtgcgcc tgcagatgcg     1320 gcggagtcct ctattcgaaa attactggtc ccatatgacg attattgcaa gtccctagtt    1380
ccggcactcg agcaaatgaa tcgatttaac tacgtctgtt atcgcgatac acgtttaggt    1440
ccccaggtgg catgcctctg gcagttttc gctggcatag agcgatattt gtcagatgtt     1500
aacattgaaa ccttcgcaca ttacgcgatt aaatgggttt gggagccat ggtgcctgaa     1560 tatcaacaag tcgcacagaa atgcattgag catatcgaaa ccgtcccct cgatgagcga     1620 cttcccgatg cgatggttga tgagttgctt gcgttttcga accgaattaa aagtgctgcc    1680
gtggccgcag acgactcag tctccggtgg gatgcgatcc tgcgctcttt cgatcggtct     1740
ttgaatttcg tcgaagggaa gacaagcagg gacatctata cgagacaatg ctcgggttgc    1800
ggggcatggc tccaactccg cccagattgg aaaaagtgcc actcatgcgg tcttctgggc    1860
accgagccgc aaacggccgt tacctttgat ccccgctga ccgcagaaga agaagcgtta     1920
ctttacgctg cctggaatac tgcgcctaaa tacgaccct cgaaggagtt aaagctacca     1980
acccctacca ggccagctgc atag                                             2004
```

```
<210> SEQ ID NO 6
<211> LENGTH: 667
<212> TYPE: PRT
<213> ORGANISM: Malbranchea aurantiaca
<220> FEATURE:
<221> NAME/KEY: MISC_FEATURE
<223> OTHER INFORMATION: MalA (S129A) protein
<220> FEATURE:
<221> NAME/KEY: MISC_FEATURE
<222> LOCATION: (129)..(129)
<223> OTHER INFORMATION: MalA (S129A) variant

<400> SEQUENCE: 6
```

Met Ala Pro Thr Pro Lys Tyr Thr Phe Thr Glu Arg Ala Ala Gly
1               5                   10                  15

Asn Leu Ser Asp Ala Glu Ile Leu Asn Ser Asn Asn Pro Thr Gly Ser
                20                  25                  30

Glu Leu Pro Asp Glu Ser Asp Val Val Gly Gly Ala Gly Ile His
            35                  40                  45

Gly Leu Ile Tyr Ala Leu His Ala Ser Lys Tyr Lys Pro Asn Asn Leu
        50                  55                  60

Lys Ile Ser Val Ile Glu Lys Asn Thr Arg Pro Gly Tyr Lys Ile Gly
65                  70                  75                  80

-continued

Glu Ser Thr Leu Pro Ile Phe Tyr Thr Trp Cys Lys Leu His Gly Ile
                85                  90                  95

Ser Ala Ala Tyr Leu Leu Arg Leu Phe Gly Leu Lys Asp Gly Leu Cys
            100                 105                 110

Phe Tyr Phe Leu Asp Arg Glu Asn Gln Gly Gln Tyr Thr Asp Phe Cys
            115                 120                 125

Ala Val Gly Ala Pro Gly Leu Val Leu Ala Ser Leu Gln Ile Glu Arg
130                 135                 140

Pro Met Ser Glu Leu Leu Phe Thr Ile Leu Ala Gln Arg Asn Gly Val
145                 150                 155                 160

Asn Val Tyr His Gly Arg Glu Val Asp Phe Lys Ser Thr Val Val Gln
                165                 170                 175

Gly Gly Gly Gln Gly Asn Lys Ile Ala Val Ser Arg Gly Lys Tyr Asp
            180                 185                 190

Ser Thr Pro Lys Thr Ile Asp Ser Ala Leu Phe Val Asp Ala Thr Gly
            195                 200                 205

Arg Phe Arg Gln Phe Cys Ser Lys Lys Ala Pro Arg His Arg Phe Asp
    210                 215                 220

Gly Trp Asn Cys Asn Ala Phe Trp Gly Tyr Phe Thr Ala Pro Lys Asp
225                 230                 235                 240

Glu Ser Lys Ile Pro Phe Asp Leu Tyr Glu Gly Asp His Thr Asn His
                245                 250                 255

Leu Cys Phe Pro Glu Gly Trp Val Trp Val Ile Arg Leu Pro Ser Trp
            260                 265                 270

Glu Gly Ser Leu Ile Ala Asn Leu Met Asp Met Val Thr Tyr Ile Leu
            275                 280                 285

Glu Cys Ala Asp Ala Gly Val Pro Gly Asp Glu Leu Pro Ser Ser Glu
            290                 295                 300

Glu Leu Ala Arg Met Phe Gly Leu Lys Phe Gln Trp Val Thr Ser Ile
305                 310                 315                 320

Gly Phe Ala Val Arg Asn Asp Val Lys Tyr Pro Glu Asp Leu Ser Ala
                325                 330                 335

Tyr Gly Thr Arg Glu Ala Glu Gln Lys Phe Asn Tyr Phe Val Gln Lys
            340                 345                 350

Tyr Glu Leu Leu Gln Gln Phe Met Ser Asn Phe Glu Leu Ile Glu Asn
            355                 360                 365

Leu Tyr Gly Pro Gly Thr Thr Trp Phe Ile Arg Lys Thr Leu Ala Tyr
    370                 375                 380

Gln Ser Pro Val Val Ser Gly Pro Gly Trp Leu Ala Ile Gly Asp Ala
385                 390                 395                 400

Cys Gly Phe Thr Asn Pro Leu Tyr Ser Pro Gly Ile Asn Val Gly Met
                405                 410                 415

Ser Thr Ser Thr Trp Ala Ala Gln Leu Ser His Arg Ile Val Glu Ile
            420                 425                 430

Gly Lys Ser Ala Pro Ala Asp Ala Ala Glu Ser Ser Ile Arg Lys Leu
            435                 440                 445

Leu Val Pro Tyr Asp Asp Tyr Cys Lys Ser Leu Val Pro Ala Leu Glu
    450                 455                 460

Gln Met Asn Arg Phe Asn Tyr Val Cys Tyr Arg Asp Thr Arg Leu Gly
465                 470                 475                 480

Pro Gln Val Ala Cys Leu Trp Gln Phe Phe Ala Gly Ile Glu Arg Tyr
                485                 490                 495

| | | | | | | | | | | | | |
|---|---|---|---|---|---|---|---|---|---|---|---|---|
|Leu|Ser|Asp|Val|Asn|Ile|Glu|Thr|Phe|Ala|His|Tyr|Ala|Ile|Lys|Trp|
| | | |500| | | |505| | | |510| | | | |

Leu Ser Asp Val Asn Ile Glu Thr Phe Ala His Tyr Ala Ile Lys Trp
            500             505             510

Val Trp Gly Ala Met Val Pro Glu Tyr Gln Gln Val Ala Gln Lys Cys
        515             520             525

Ile Glu His Ile Glu Thr Val Pro Leu Asp Glu Arg Leu Pro Asp Ala
    530             535             540

Met Val Asp Glu Leu Leu Ala Phe Ser Asn Arg Ile Lys Ser Ala Ala
545             550             555             560

Val Ala Ala Asp Asp Phe Ser Leu Arg Trp Asp Ala Ile Leu Arg Ser
            565             570             575

Phe Asp Arg Ser Leu Asn Phe Val Glu Gly Lys Thr Ser Arg Asp Ile
        580             585             590

Tyr Thr Arg Gln Cys Ser Gly Cys Gly Ala Trp Leu Gln Leu Arg Pro
    595             600             605

Asp Trp Lys Lys Cys His Ser Cys Gly Leu Leu Gly Thr Glu Pro Gln
        610             615             620

Thr Ala Val Thr Phe Asp Pro Pro Leu Thr Ala Glu Glu Ala Leu
625             630             635             640

Leu Tyr Ala Ala Trp Asn Thr Ala Pro Lys Tyr Asp Pro Ser Lys Glu
            645             650             655

Leu Lys Leu Pro Thr Pro Thr Arg Pro Ala Ala
            660             665

<210> SEQ ID NO 7
<211> LENGTH: 2004
<212> TYPE: DNA
<213> ORGANISM: Malbranchea aurantiaca
<220> FEATURE:
<221> NAME/KEY: misc_feature
<223> OTHER INFORMATION: MalA (S129A/I493S) coding region
<220> FEATURE:
<221> NAME/KEY: misc_feature
<223> OTHER INFORMATION: MalA (S129A) codon variant
<220> FEATURE:
<221> NAME/KEY: misc_feature
<223> OTHER INFORMATION: MalA (I493S) codon variant

<400> SEQUENCE: 7

```
atggcgccga caccaaagta tacgtttacc gagagggctg cggcaggcaa tctcagcgac     60
gctgagattc tcaactccaa taatcctact ggatctgagc tcccagatga atcggatgtg    120
gtggtgggcg gtgctggtat ccatggtctg atctatgccc ttcacgcttc aaagtataaa    180
ccgaacaacc tcaagatctc cgttattgag aagaacacta ggcctggtta caagattggc    240
gagagcactc tacctatctt ttacacctgg tgcaaactcc acggcatctc cgcggcatac    300
ctccttcgac tattcggact caaggatggg ctgtgctttt actttcttga tcgagagaac    360
caggggcagt acacagactt ctgcgcggtt ggggctccag gtttggtatt agccagttta    420
cagattgagc ggccaatgag cgagctgctc tttacaattc ttgcgcaacg aaatggagtc    480
aatgtctatc acggccggga ggtggatttt aaaagcacgg tggtccaagg gggtggccag    540
ggcaacaaga tcgcagtctc ccggggcaaa tatgatagca cacccaagac aatagattca    600
gccctcttcg ttgacgcaac aggccgcttc cgccaatttt gctccaagaa agcccccga    660 caccgattcg atggatggaa ctgcaacgcc ttctggggtt atttcactgc cccaaaggat    720
gagagcaaga ttcccttga tctctatgaa ggtgatcaca caaaccaccct gtgttttccg    780 gaaggttggg tctgggttat tcgtctaccc tcttgggaag ggagcctcat agcgaacttg    840
atggatatgg tgacatacat actcgaatgc gctgacgccg gagtacctgg tgatgaactc    900
```

-continued

```
ccgagttctg aagagcttgc caggatgttt gggctcaagt tcagtgggt gacaagtatt    960
ggctttgccg tgcgcaatga tgtcaagtac ccggaagatc tctcagccta tgggacccgt   1020
gaggcagagc aaaaattcaa ctactttgtt cagaagtatg agctgcttca gcagttcatg   1080
tcaaactttg agcttattga aaatctttat ggccctggga ccacatggtt catccgtaag   1140
acgctggcat accagtctcc agtggtttct ggacctggct ggcttgccat tggtgatgcc   1200
tgtggtttca ccaacccgct ctattctccg gggattaatg ttggcatgtc gacttcaaca   1260
tgggccgcac agctttcgca ccgaattgtg gagattggga aagtgcgcc tgcagatgcg    1320
gcggagtcct ctattcgaaa attactggtc ccatatgacg attattgcaa gtccctagtt   1380
ccggcactcg agcaaatgaa tcgatttaac tacgtctgtt atcgcgatac acgtttaggt   1440
ccccaggtgg catgcctctg cagttttc gctggctctg agcgatattt gtcagatgtt    1500
aacattgaaa ccttcgcaca ttacgcgatt aaatgggttt ggggagccat ggtgcctgaa   1560
tatcaacaag tcgcacagaa atgcattgag catatcgaaa ccgtcccct cgatgagcga    1620
cttcccgatg cgatggttga tgagttgctt gcgttttcga accgaattaa aagtgctgcc   1680
gtggccgcag acgacttcag tctccggtgg gatgcgatcc tgcgctcttt cgatcggtct   1740
ttgaatttcg tcgaagggaa gacaagcagg gacatctata cgacaatg ctcgggttgc     1800
ggggcatggc tccaactccg cccagattgg aaaaagtgcc actcatgcgg tcttctgggc   1860
accgagccgc aaacggccgt tacctttgat ccccgctga ccgcagaaga gaagcgtta    1920
ctttacgctg cctggaatac tgcgcctaaa tacgacccct cgaaggagtt aaagctacca   1980
acccctacca ggccagctgc atag                                         2004
```

<210> SEQ ID NO 8
<211> LENGTH: 667
<212> TYPE: PRT
<213> ORGANISM: Malbranchea aurantiaca
<220> FEATURE:
<221> NAME/KEY: MISC_FEATURE
<223> OTHER INFORMATION: MalA (S129A/I493S) protein
<220> FEATURE:
<221> NAME/KEY: MISC_FEATURE
<222> LOCATION: (129)..(129)
<223> OTHER INFORMATION: MalA (S129A) variant
<220> FEATURE:
<221> NAME/KEY: MISC_FEATURE
<222> LOCATION: (143)..(143)
<223> OTHER INFORMATION: MalA (I493S) variant

<400> SEQUENCE: 8

```
Met Ala Pro Thr Pro Lys Tyr Thr Phe Thr Glu Arg Ala Ala Gly
1               5                   10                  15

Asn Leu Ser Asp Ala Glu Ile Leu Asn Ser Asn Asn Pro Thr Gly Ser
            20                  25                  30

Glu Leu Pro Asp Glu Ser Asp Val Val Gly Gly Ala Gly Ile His
        35                  40                  45

Gly Leu Ile Tyr Ala Leu His Ala Ser Lys Tyr Lys Pro Asn Asn Leu
    50                  55                  60

Lys Ile Ser Val Ile Glu Lys Asn Thr Arg Pro Gly Tyr Lys Ile Gly
65                  70                  75                  80

Glu Ser Thr Leu Pro Ile Phe Tyr Thr Trp Cys Lys Leu His Gly Ile
                85                  90                  95

Ser Ala Ala Tyr Leu Leu Arg Leu Phe Gly Leu Lys Asp Gly Leu Cys
            100                 105                 110
```

```
Phe Tyr Phe Leu Asp Arg Glu Asn Gln Gly Gln Tyr Thr Asp Phe Cys
        115                 120                 125

Ala Val Gly Ala Pro Gly Leu Val Leu Ala Ser Leu Gln Ile Glu Arg
    130                 135                 140

Pro Met Ser Glu Leu Leu Phe Thr Ile Leu Ala Gln Arg Asn Gly Val
145                 150                 155                 160

Asn Val Tyr His Gly Arg Glu Val Asp Phe Lys Ser Thr Val Val Gln
                165                 170                 175

Gly Gly Gly Gln Gly Asn Lys Ile Ala Val Ser Arg Gly Lys Tyr Asp
            180                 185                 190

Ser Thr Pro Lys Thr Ile Asp Ser Ala Leu Phe Val Asp Ala Thr Gly
            195                 200                 205

Arg Phe Arg Gln Phe Cys Ser Lys Lys Ala Pro Arg His Arg Phe Asp
    210                 215                 220

Gly Trp Asn Cys Asn Ala Phe Trp Gly Tyr Phe Thr Ala Pro Lys Asp
225                 230                 235                 240

Glu Ser Lys Ile Pro Phe Asp Leu Tyr Glu Gly Asp His Thr Asn His
                245                 250                 255

Leu Cys Phe Pro Glu Gly Trp Val Trp Val Ile Arg Leu Pro Ser Trp
            260                 265                 270

Glu Gly Ser Leu Ile Ala Asn Leu Met Asp Met Val Thr Tyr Ile Leu
            275                 280                 285

Glu Cys Ala Asp Ala Gly Val Pro Gly Asp Glu Leu Pro Ser Ser Glu
    290                 295                 300

Glu Leu Ala Arg Met Phe Gly Leu Lys Phe Gln Trp Val Thr Ser Ile
305                 310                 315                 320

Gly Phe Ala Val Arg Asn Asp Val Lys Tyr Pro Glu Asp Leu Ser Ala
                325                 330                 335

Tyr Gly Thr Arg Glu Ala Glu Gln Lys Phe Asn Tyr Phe Val Gln Lys
            340                 345                 350

Tyr Glu Leu Leu Gln Gln Phe Met Ser Asn Phe Glu Leu Ile Glu Asn
            355                 360                 365

Leu Tyr Gly Pro Gly Thr Thr Trp Phe Ile Arg Lys Thr Leu Ala Tyr
    370                 375                 380

Gln Ser Pro Val Val Ser Gly Pro Gly Trp Leu Ala Ile Gly Asp Ala
385                 390                 395                 400

Cys Gly Phe Thr Asn Pro Leu Tyr Ser Pro Gly Ile Asn Val Gly Met
                405                 410                 415

Ser Thr Ser Thr Trp Ala Ala Gln Leu Ser His Arg Ile Val Glu Ile
            420                 425                 430

Gly Lys Ser Ala Pro Ala Asp Ala Ala Glu Ser Ser Ile Arg Lys Leu
            435                 440                 445

Leu Val Pro Tyr Asp Asp Tyr Cys Lys Ser Leu Val Pro Ala Leu Glu
    450                 455                 460

Gln Met Asn Arg Phe Asn Tyr Val Cys Tyr Arg Asp Thr Arg Leu Gly
465                 470                 475                 480

Pro Gln Val Ala Cys Leu Trp Gln Phe Phe Ala Gly Ser Glu Arg Tyr
                485                 490                 495

Leu Ser Asp Val Asn Ile Glu Thr Phe Ala His Tyr Ala Ile Lys Trp
            500                 505                 510

Val Trp Gly Ala Met Val Pro Glu Tyr Gln Gln Val Ala Gln Lys Cys
            515                 520                 525
```

| Ile | Glu | His | Ile | Glu | Thr | Val | Pro | Leu | Asp | Glu | Arg | Leu | Pro | Asp | Ala |
|---|---|---|---|---|---|---|---|---|---|---|---|---|---|---|---|
| 530 | | | | 535 | | | | | 540 | | | | | | |

| Met | Val | Asp | Glu | Leu | Leu | Ala | Phe | Ser | Asn | Arg | Ile | Lys | Ser | Ala | Ala |
|---|---|---|---|---|---|---|---|---|---|---|---|---|---|---|---|
| 545 | | | | | 550 | | | | | 555 | | | | | 560 |

| Val | Ala | Ala | Asp | Asp | Phe | Ser | Leu | Arg | Trp | Asp | Ala | Ile | Leu | Arg | Ser |
|---|---|---|---|---|---|---|---|---|---|---|---|---|---|---|---|
| | | | | 565 | | | | | 570 | | | | | 575 | |

| Phe | Asp | Arg | Ser | Leu | Asn | Phe | Val | Glu | Gly | Lys | Thr | Ser | Arg | Asp | Ile |
|---|---|---|---|---|---|---|---|---|---|---|---|---|---|---|---|
| | | | 580 | | | | | 585 | | | | | 590 | | |

| Tyr | Thr | Arg | Gln | Cys | Ser | Gly | Cys | Gly | Ala | Trp | Leu | Gln | Leu | Arg | Pro |
|---|---|---|---|---|---|---|---|---|---|---|---|---|---|---|---|
| | | 595 | | | | | 600 | | | | | 605 | | | |

| Asp | Trp | Lys | Lys | Cys | His | Ser | Cys | Gly | Leu | Leu | Gly | Thr | Glu | Pro | Gln |
|---|---|---|---|---|---|---|---|---|---|---|---|---|---|---|---|
| | 610 | | | | | 615 | | | | | 620 | | | | |

| Thr | Ala | Val | Thr | Phe | Asp | Pro | Pro | Leu | Thr | Ala | Glu | Glu | Glu | Ala | Leu |
|---|---|---|---|---|---|---|---|---|---|---|---|---|---|---|---|
| 625 | | | | | 630 | | | | | 635 | | | | | 640 |

| Leu | Tyr | Ala | Ala | Trp | Asn | Thr | Ala | Pro | Lys | Tyr | Asp | Pro | Ser | Lys | Glu |
|---|---|---|---|---|---|---|---|---|---|---|---|---|---|---|---|
| | | | | 645 | | | | | 650 | | | | | 655 | |

| Leu | Lys | Leu | Pro | Thr | Pro | Thr | Arg | Pro | Ala | Ala |
|---|---|---|---|---|---|---|---|---|---|---|
| | | | 660 | | | | 665 | | | |

```
<210> SEQ ID NO 9
<211> LENGTH: 2004
<212> TYPE: DNA
<213> ORGANISM: Malbranchea graminicola
<220> FEATURE:
<221> NAME/KEY: misc_feature
<223> OTHER INFORMATION: MalA' (S129A/I493S) coding region
<220> FEATURE:
<221> NAME/KEY: misc_feature
<223> OTHER INFORMATION: MalA' (S129A) codon variant
<220> FEATURE:
<221> NAME/KEY: misc_feature
<223> OTHER INFORMATION: MalA' (I493S) codon variant

<400> SEQUENCE: 9
atggcgccga caccaaagta tacgtttacc gagagggctg cggcaggcaa tctcagcgac      60
gctgagattc tcaactccaa taatcctact ggatctgagc tcccagatga atcggatgtg     120
gtggtgggcg gtgctggtat ccatggtctg atctatgccc ttcacgcttc aaagtataaa     180
ccgaacaacc tcaagatctc cgttattgag aagaacacta ggcctggtta caagattggc     240
gagagcactc tacctatctt ttacacctgg tgcaaactcc acggcatctc cgcggcatac     300
ctccttcgac tattcggact caaggatggg ctgtgctttt actttcttga tcgagagaac     360
caggggcagt acacagactt ctgcgcggtt ggggctccag gtttggtatt agccagttta     420
cagattgagc ggccaatgag cgagctgctc tttacaattc ttgcgcaacg aaatggagtc     480
aatgtctatc acggccggga ggtggatttt aaaagcacgg tggtccaagg ggtggccag      540 ggcaacaaga tcgcagtctc ccggggcaaa tatgatagca cacccaagac aatagattca     600
gccctcttcg ttgacgcaac aggccgcttc cgccaatttt gctccaagaa agccccccga     660
caccgattcg atggatggaa ctgcaacgcc ttctggggtt atttcactgc cccaaaggat     720
gagagcaaga ttcccttga tctctatgaa ggtgatcaca caaaccacct gtgttttccg      780
gaaggttggg tctgggttat tcgtctaccc tcttgggaag ggagcccat agcgaacttg      840 atggatatgg tgacatacat actcgaatgc gctgacgccg agtacctgg tgatgaactc      900 ccgagttctg aagagcttgc caggatgttt gggctcaagt ttcagtgggt gacaagtatt     960
ggctttgccg tgcgcaatga tgtcaagtac ccggaagatc tctcagccta tgggacccgt    1020
gaggcagagc aaaaaattca actactttgt tcagaagtatg agctgcttca gcagttcatg    1080
```

```
tcaaactttg agcttattga aaatctttat ggccctggga ccacatggtt catccgtaag    1140
acgctggcat accagtctcc agtggtttct ggacctggct ggcttgccat tggtgatgcc    1200
tgtggtttca ccaacccgct ctattctccg gggattaatg ttggcatgtc gacttcaaca    1260
tgggccgcac agctttcgca cccgattgtg gagattggga aaagtgcgcc tgcagatgcg    1320
gcggagtcct ctattcgaaa attactggtc ccatatgacg attattgcaa gtccctagtt    1380
ccggcactcg agcaaatgaa tcgatttaac tacgtctgtt atcgcgatac acgtttaggt    1440
ccccaggtgg catgcctctg cagttttc gctggctctg agcgatattt gtcagatgtt    1500
aacattgaaa ccttcgcaca ttacgcgatt aaatgggttt ggggagccat ggtgcctgaa    1560
tatcaacaag tcgcacagaa atgcattgag catatcgaaa ccgtccccct cgatgagcga    1620
cttcccgatg cgatggttga tgagttgctt gcgttttcga accgaattaa aagtgctgcc    1680
gtggccgcag acgacttcag tctccggtgg gatgcgatcc tgcgctcttt cgatcggtct    1740
ttgaatttcg tcgaagggaa gacaagcagg gacatctata cgagacaatg ctcgggttgc    1800
ggggcatggc tccaactccg cccagattgg aaaaagtgcc actcatgcgg tcttctgggc    1860
accgagccgc aaacggccgt tacctttgat cccccgctga ccgcagaaga agaagcgtta    1920
ctttacgctg cctggaatac tgcgcctaaa tacgacccct cgaaggagtt aaagctacca    1980
acccctacca ggccagctgc atag                                          2004
```

<210> SEQ ID NO 10
<211> LENGTH: 667
<212> TYPE: PRT
<213> ORGANISM: Malbranchea graminicola
<220> FEATURE:
<221> NAME/KEY: MISC_FEATURE
<223> OTHER INFORMATION: MalA' (S129A/I493S) protein
<220> FEATURE:
<221> NAME/KEY: MISC_FEATURE
<222> LOCATION: (129)..(129)
<223> OTHER INFORMATION: MalA' (S129A) variant
<220> FEATURE:
<221> NAME/KEY: MISC_FEATURE
<222> LOCATION: (493)..(493)
<223> OTHER INFORMATION: MalA' (I493S) variant

<400> SEQUENCE: 10

```
Met Ala Pro Thr Pro Lys Tyr Thr Phe Thr Glu Arg Ala Ala Gly
1               5                   10                  15

Asn Leu Ser Asp Ala Glu Ile Leu Asn Ser Asn Pro Thr Gly Ser
            20                  25                  30

Glu Leu Pro Asp Glu Ser Asp Val Val Gly Gly Ala Gly Ile His
        35                  40                  45

Gly Leu Ile Tyr Ala Leu His Ala Ser Lys Tyr Lys Pro Asn Asn Leu
    50                  55                  60

Lys Ile Ser Val Ile Glu Lys Asn Thr Arg Pro Gly Tyr Lys Ile Gly
65                  70                  75                  80

Glu Ser Thr Leu Pro Ile Phe Tyr Thr Trp Cys Lys Leu His Gly Ile
                85                  90                  95

Ser Ala Ala Tyr Leu Leu Arg Leu Phe Gly Leu Lys Asp Gly Leu Cys
            100                 105                 110

Phe Tyr Phe Leu Asp Arg Glu Asn Gln Gly Gln Tyr Thr Asp Phe Cys
        115                 120                 125

Ala Val Gly Ala Pro Gly Leu Val Leu Ala Ser Leu Gln Ile Glu Arg
    130                 135                 140
```

```
Pro Met Ser Glu Leu Leu Phe Thr Ile Leu Ala Gln Arg Asn Gly Val
145                 150                 155                 160

Asn Val Tyr His Gly Arg Glu Val Asp Phe Lys Ser Thr Val Val Gln
            165                 170                 175

Gly Gly Gly Gln Gly Asn Lys Ile Ala Val Ser Arg Gly Lys Tyr Asp
            180                 185                 190

Ser Thr Pro Lys Thr Ile Asp Ser Ala Leu Phe Val Asp Ala Thr Gly
            195                 200                 205

Arg Phe Arg Gln Phe Cys Ser Lys Lys Ala Pro Arg His Arg Phe Asp
210                 215                 220

Gly Trp Asn Cys Asn Ala Phe Trp Gly Tyr Phe Thr Ala Pro Lys Asp
225                 230                 235                 240

Glu Ser Lys Ile Pro Phe Asp Leu Tyr Glu Gly Asp His Thr Asn His
                245                 250                 255

Leu Cys Phe Pro Glu Gly Trp Val Trp Val Ile Arg Leu Pro Ser Trp
            260                 265                 270

Glu Gly Ser Pro Ile Ala Asn Leu Met Asp Met Val Thr Tyr Ile Leu
            275                 280                 285

Glu Cys Ala Asp Ala Gly Val Pro Gly Asp Glu Leu Pro Ser Ser Glu
290                 295                 300

Glu Leu Ala Arg Met Phe Gly Leu Lys Phe Gln Trp Val Thr Ser Ile
305                 310                 315                 320

Gly Phe Ala Val Arg Asn Asp Val Lys Tyr Pro Glu Asp Leu Ser Ala
                325                 330                 335

Tyr Gly Thr Arg Glu Ala Glu Gln Lys Phe Asn Tyr Phe Val Gln Lys
            340                 345                 350

Tyr Glu Leu Leu Gln Gln Phe Met Ser Asn Phe Glu Leu Ile Glu Asn
            355                 360                 365

Leu Tyr Gly Pro Gly Thr Thr Trp Phe Ile Arg Lys Thr Leu Ala Tyr
            370                 375                 380

Gln Ser Pro Val Val Ser Gly Pro Gly Trp Leu Ala Ile Gly Asp Ala
385                 390                 395                 400

Cys Gly Phe Thr Asn Pro Leu Tyr Ser Pro Gly Ile Asn Val Gly Met
                405                 410                 415

Ser Thr Ser Thr Trp Ala Ala Gln Leu Ser His Pro Ile Val Glu Ile
            420                 425                 430

Gly Lys Ser Ala Pro Ala Asp Ala Ala Glu Ser Ser Ile Arg Lys Leu
            435                 440                 445

Leu Val Pro Tyr Asp Asp Tyr Cys Lys Ser Leu Val Pro Ala Leu Glu
450                 455                 460

Gln Met Asn Arg Phe Asn Tyr Val Cys Tyr Arg Asp Thr Arg Leu Gly
465                 470                 475                 480

Pro Gln Val Ala Cys Leu Trp Gln Phe Ala Gly Ser Glu Arg Tyr
                485                 490                 495

Leu Ser Asp Val Asn Ile Glu Thr Phe Ala His Tyr Ala Ile Lys Trp
            500                 505                 510

Val Trp Gly Ala Met Val Pro Glu Tyr Gln Gln Val Ala Gln Lys Cys
            515                 520                 525

Ile Glu His Ile Glu Thr Val Pro Leu Asp Glu Arg Leu Pro Asp Ala
            530                 535                 540

Met Val Asp Glu Leu Leu Ala Phe Ser Asn Arg Ile Lys Ser Ala Ala
545                 550                 555                 560
```

```
Val Ala Ala Asp Asp Phe Ser Leu Arg Trp Asp Ala Ile Leu Arg Ser
            565                 570                 575

Phe Asp Arg Ser Leu Asn Phe Val Glu Gly Lys Thr Ser Arg Asp Ile
        580                 585                 590

Tyr Thr Arg Gln Cys Ser Gly Cys Gly Ala Trp Leu Gln Leu Arg Pro
            595                 600                 605

Asp Trp Lys Lys Cys His Ser Cys Gly Leu Leu Gly Thr Glu Pro Gln
        610                 615                 620

Thr Ala Val Thr Phe Asp Pro Pro Leu Thr Ala Glu Glu Glu Ala Leu
625                 630                 635                 640

Leu Tyr Ala Ala Trp Asn Thr Ala Pro Lys Tyr Asp Pro Ser Lys Glu
            645                 650                 655

Leu Lys Leu Pro Thr Pro Thr Arg Pro Ala Ala
            660                 665

<210> SEQ ID NO 11
<211> LENGTH: 2004
<212> TYPE: DNA
<213> ORGANISM: Malbranchea aurantiaca
<220> FEATURE:
<221> NAME/KEY: misc_feature
<223> OTHER INFORMATION: MalA (S129A/P85S) coding region
<220> FEATURE:
<221> NAME/KEY: misc_feature
<223> OTHER INFORMATION: MalA (S129A) codon variant
<220> FEATURE:
<221> NAME/KEY: misc_feature
<223> OTHER INFORMATION: MalA (P85S) codon variant

<400> SEQUENCE: 11
atggcgccga caccaaagta tacgtttacc gagagggctg cggcaggcaa tctcagcgac      60
gctgagattc tcaactccaa taatcctact ggatctgagc tcccagatga atcggatgtg     120
gtggtgggcg gtgctggtat ccatggtctg atctatgccc ttcacgcttc aaagtataaa     180
ccgaacaacc tcaagatctc cgttattgag aagaacacta ggcctggtta caagattggc     240
gagagcactc tatctatctt ttacacctgg tgcaaactcc acggcatctc cgcggcatac     300
ctccttcgac tattcggact caaggatggg ctgtgctttt actttcttga tcgagagaac     360
caggggcagt acacagactt ctgcgcggtt ggggctccag gtttggtatt agccagttta     420
cagattgagc ggccaatgag cgagctgctc tttacaattc ttgcgcaacg aaatggagtc     480
aatgtctatc acggccggga ggtggatttt aaaagcacgg tggtccaagg gggtggccag     540
ggcaacaaga tcgcagtctc ccggggcaaa tatgatagca cacccaagac aatagattca     600
gccctcttcg ttgacgcaac aggccgcttc cgccaatttt gctccaagaa agcccccga      660 caccgattcg atggatggaa ctgcaacgcc ttctggggtt atttcactgc cccaaaggat     720
gagagcaaga ttcccttga tctctatgaa ggtgatcaca caaccacct gtgttttccg     780 gaaggttggg tctgggttat tcgtctaccc tcttgggaag ggagcctcat agcgaacttg     840
atggatatgg tgacatacat actcgaatgc gctgacgccg gagtacctgg tgatgaactc     900
ccgagttctg aagagcttgc caggatgttt gggctcaagt ttcagtgggt gacaagtatt     960
ggctttgccg tgcgcaatga tgtcaagtac ccggaagatc tctcagccta gggaccgt    1020 gaggcagagc aaaaattcaa ctactttgtt cagaagtatg agctgcttca gcagttcatg    1080
tcaaactttg agcttattga aaatcttat ggccctggga ccacatggtt catccgtaag    1140
acgctggcat accagtctcc agtggtttct ggacctggct ggcttgccat ggtgatgcc    1200 tgtggtttca ccaacccgct ctattctccg gggattaatg ttggcatgtc gacttcaaca    1260
```

```
tgggccgcac agctttcgca ccgaattgtg gagattggga aaagtgcgcc tgcagatgcg    1320
gcggagtcct ctattcgaaa attactggtc ccatatgacg attattgcaa gtccctagtt    1380
ccggcactcg agcaaatgaa tcgatttaac tacgtctgtt atcgcgatac acgtttaggt    1440
ccccaggtgg catgcctctg gcagtttttc gctggcatag agcgatattt gtcagatgtt    1500
aacattgaaa ccttcgcaca ttacgcgatt aaatgggttt ggggagccat ggtgcctgaa    1560
tatcaacaag tcgcacagaa atgcattgag catatcgaaa ccgtccccct cgatgagcga    1620
cttcccgatg cgatggttga tgagttgctt gcgttttcga accgaattaa aagtgctgcc    1680
gtggccgcag acgacttcag tctccggtgg gatgcgatcc tgcgctcttt cgatcggtct    1740
ttgaatttcg tcgaagggaa gacaagcagg gacatctata cgagacaatg ctcgggttgc    1800
ggggcatggc tccaactccg cccagattgg aaaaagtgcc actcatgcgg tcttctgggc    1860
accgagccgc aaacggccgt tacctttgat ccccgctga ccgcagaaga agaagcgtta    1920
ctttacgctg cctggaatac tgcgcctaaa tacgacccct cgaaggagtt aaagctacca    1980 accccctacca ggccagctgc atag                                          2004
```

<210> SEQ ID NO 12
<211> LENGTH: 667
<212> TYPE: PRT
<213> ORGANISM: Malbranchea aurantiaca
<220> FEATURE:
<221> NAME/KEY: MISC_FEATURE
<223> OTHER INFORMATION: MalA (S129A/P85S) protein
<220> FEATURE:
<221> NAME/KEY: MISC_FEATURE
<222> LOCATION: (85)..(85)
<223> OTHER INFORMATION: MalA (P85S) variant
<220> FEATURE:
<221> NAME/KEY: MISC_FEATURE
<222> LOCATION: (129)..(129)
<223> OTHER INFORMATION: MalA (S129A) variant

<400> SEQUENCE: 12

```
Met Ala Pro Thr Pro Lys Tyr Thr Phe Thr Glu Arg Ala Ala Gly
1               5                   10                  15

Asn Leu Ser Asp Ala Glu Ile Leu Asn Ser Asn Asn Pro Thr Gly Ser
            20                  25                  30

Glu Leu Pro Asp Glu Ser Asp Val Val Gly Gly Ala Gly Ile His
        35                  40                  45

Gly Leu Ile Tyr Ala Leu His Ala Ser Lys Tyr Lys Pro Asn Asn Leu
    50                  55                  60

Lys Ile Ser Val Ile Glu Lys Asn Thr Arg Pro Gly Tyr Lys Ile Gly
65                  70                  75                  80

Glu Ser Thr Leu Ser Ile Phe Tyr Thr Trp Cys Lys Leu His Gly Ile
                85                  90                  95

Ser Ala Ala Tyr Leu Leu Arg Leu Phe Gly Leu Lys Asp Gly Leu Cys
            100                 105                 110

Phe Tyr Phe Leu Asp Arg Glu Asn Gln Gly Gln Tyr Thr Asp Phe Cys
        115                 120                 125

Ala Val Gly Ala Pro Gly Leu Val Leu Ala Ser Leu Gln Ile Glu Arg
    130                 135                 140

Pro Met Ser Glu Leu Leu Phe Thr Ile Leu Ala Gln Arg Asn Gly Val
145                 150                 155                 160

Asn Val Tyr His Gly Arg Glu Val Asp Phe Lys Ser Thr Val Val Gln
                165                 170                 175
```

```
Gly Gly Gly Gln Gly Asn Lys Ile Ala Val Ser Arg Gly Lys Tyr Asp
            180                 185                 190

Ser Thr Pro Lys Thr Ile Asp Ser Ala Leu Phe Val Asp Ala Thr Gly
        195                 200                 205

Arg Phe Arg Gln Phe Cys Ser Lys Lys Ala Pro Arg His Arg Phe Asp
    210                 215                 220

Gly Trp Asn Cys Asn Ala Phe Trp Gly Tyr Phe Thr Ala Pro Lys Asp
225                 230                 235                 240

Glu Ser Lys Ile Pro Phe Asp Leu Tyr Glu Gly Asp His Thr Asn His
                245                 250                 255

Leu Cys Phe Pro Glu Gly Trp Val Trp Val Ile Arg Leu Pro Ser Trp
            260                 265                 270

Glu Gly Ser Leu Ile Ala Asn Leu Met Asp Met Val Thr Tyr Ile Leu
        275                 280                 285

Glu Cys Ala Asp Ala Gly Val Pro Gly Asp Glu Leu Pro Ser Ser Glu
    290                 295                 300

Glu Leu Ala Arg Met Phe Gly Leu Lys Phe Gln Trp Val Thr Ser Ile
305                 310                 315                 320

Gly Phe Ala Val Arg Asn Asp Val Lys Tyr Pro Glu Asp Leu Ser Ala
                325                 330                 335

Tyr Gly Thr Arg Glu Ala Glu Gln Lys Phe Asn Tyr Phe Val Gln Lys
            340                 345                 350

Tyr Glu Leu Leu Gln Gln Phe Met Ser Asn Phe Glu Leu Ile Glu Asn
        355                 360                 365

Leu Tyr Gly Pro Gly Thr Thr Trp Phe Ile Arg Lys Thr Leu Ala Tyr
    370                 375                 380

Gln Ser Pro Val Val Ser Gly Pro Gly Trp Leu Ala Ile Gly Asp Ala
385                 390                 395                 400

Cys Gly Phe Thr Asn Pro Leu Tyr Ser Pro Gly Ile Asn Val Gly Met
                405                 410                 415

Ser Thr Ser Thr Trp Ala Ala Gln Leu Ser His Arg Ile Val Glu Ile
            420                 425                 430

Gly Lys Ser Ala Pro Ala Asp Ala Ala Glu Ser Ser Ile Arg Lys Leu
        435                 440                 445

Leu Val Pro Tyr Asp Asp Tyr Cys Lys Ser Leu Val Pro Ala Leu Glu
    450                 455                 460

Gln Met Asn Arg Phe Asn Tyr Val Cys Tyr Arg Asp Thr Arg Leu Gly
465                 470                 475                 480

Pro Gln Val Ala Cys Leu Trp Gln Phe Phe Ala Gly Ile Glu Arg Tyr
                485                 490                 495

Leu Ser Asp Val Asn Ile Glu Thr Phe Ala His Tyr Ala Ile Lys Trp
            500                 505                 510

Val Trp Gly Ala Met Val Pro Glu Tyr Gln Gln Val Ala Gln Lys Cys
        515                 520                 525

Ile Glu His Ile Glu Thr Val Pro Leu Asp Glu Arg Leu Pro Asp Ala
    530                 535                 540

Met Val Asp Glu Leu Leu Ala Phe Ser Asn Arg Ile Lys Ser Ala Ala
545                 550                 555                 560

Val Ala Ala Asp Asp Phe Ser Leu Arg Trp Asp Ala Ile Leu Arg Ser
                565                 570                 575

Phe Asp Arg Ser Leu Asn Phe Val Glu Gly Lys Thr Ser Arg Asp Ile
            580                 585                 590
```

```
Tyr Thr Arg Gln Cys Ser Gly Cys Gly Ala Trp Leu Gln Leu Arg Pro
            595                 600                 605

Asp Trp Lys Lys Cys His Ser Cys Gly Leu Leu Gly Thr Glu Pro Gln
610                 615                 620

Thr Ala Val Thr Phe Asp Pro Pro Leu Thr Ala Glu Glu Ala Leu
625                 630                 635                 640

Leu Tyr Ala Ala Trp Asn Thr Ala Pro Lys Tyr Asp Pro Ser Lys Glu
                645                 650                 655

Leu Lys Leu Pro Thr Pro Thr Arg Pro Ala Ala
            660                 665

<210> SEQ ID NO 13
<211> LENGTH: 2004
<212> TYPE: DNA
<213> ORGANISM: Malbranchea graminicola
<220> FEATURE:
<221> NAME/KEY: misc_feature
<223> OTHER INFORMATION: MalA' (S129A/P85S) protein
<220> FEATURE:
<221> NAME/KEY: misc_feature
<223> OTHER INFORMATION: MalA' (P85S) codon variant
<220> FEATURE:
<221> NAME/KEY: misc_feature
<223> OTHER INFORMATION: MalA' (S129A) codon variant

<400> SEQUENCE: 13
atggcgccga caccaaagta tacgtttacc gagagggctg cggcaggcaa tctcagcgac      60
gctgagattc tcaactccaa taatcctact ggatctgagc tcccagatga atcggatgtg     120
gtggtgggcg gtgctggtat ccatggtctg atctatgccc tcacgcttc aaagtataaa      180 ccgaacaacc tcaagatctc cgttattgag aagaacacta ggcctggtta caagattggc     240
gagagcactc tatctatctt ttacacctgg tgcaaactcc acggcatctc cgcggcatac     300
ctccttcgac tattcggact caaggatggg ctgtgctttt actttcttga tcgagagaac     360
caggggcagt acacagactt ctgcgcggtt ggggctccag gtttggtatt agccagttta     420
cagattgagc ggccaatgag cgagctgctc tttacaattc ttgcgcaacg aaatggagtc     480
aatgtctatc acggccggga ggtggatttt aaaagcacgg tggtccaagg gggtggccag     540
ggcaacaaga tcgcagtctc ccggggcaaa tatgatagca cacccaagac aatagattca     600
gccctcttcg ttgacgcaac aggccgcttc cgccaatttt gctccaagaa agcccccga      660 caccgattcg atggatggaa ctgcaacgcc ttctggggtt atttcactgc ccaaaggat      720 gagagcaaga ttccctttga tctctatgaa ggtgatcaca caaaccacct gtgttttccg     780
gaaggttggg tctgggttat tcgtctaccc tcttgggaag ggagccccat agcgaacttg     840
atggatatgg tgcatacat actcgaatgc gctgacgccg gagtacctgg tgatgaactc      900
ccgagttctg aagagcttgc aggatgtttt gggctcaagt ttcagtgggt gacaagtatt     960
ggctttgccg tgcgcaatga tgtcaagtac ccggaagatc tctcagccta tgggaccgt    1020 gaggcagagc aaaaattcaa ctactttgtt cagaagtatg agctgcttca gcagttcatg    1080
tcaaactttg agcttattga aaatctttat ggccctggga ccacatggtt catccgtaag    1140
acgctggcat accagtctcc agtggtttct ggacctggct ggcttgccat tggtgatgcc    1200
tgtggtttca ccaacccgct ctattctccg gggattaatg ttggcatgtc gacttcaaca    1260
tgggccgcac agctttcgca cccgattgtg gagattggga aagtgcgcc tgcagatgcg     1320 gcggagtcct ctattcgaaa attactggtc ccatatgacg attattgcaa gtccctagtt    1380
ccggcactcg agcaaatgaa tcgatttaac tacgtctgtt atcgcgatac acgtttaggt    1440
```

-continued

```
cccagg tgg catgcctctg gcagttttc gctggcatag agcgatattt gtcagatgtt    1500
aacattgaaa ccttcgcaca ttacgcgatt aaatgggttt ggggagccat ggtgcctgaa    1560
tatcaacaag tcgcacagaa atgcattgag catatcgaaa ccgtccccct cgatgagcga    1620
cttcccgatg cgatggttga tgagttgctt gcgttttcga accgaattaa aagtgctgcc    1680
gtggccgcag acgacttcag tctccggtgg gatgcgatcc tgcgctcttt cgatcggtct    1740
ttgaatttcg tcgagggaa gacaagcagg gacatctata cgagacaatg ctcgggttgc    1800
ggggcatggc tccaactccg cccagattgg aaaaagtgcc actcatgcgg tcttctgggc    1860
accgagccgc aaacggccgt tacctttgat cccccgctga ccgcagaaga agaagcgtta    1920
ctttacgctg cctggaatac tgcgcctaaa tacgacccct cgaaggagtt aaagctacca    1980 accctacca ggccagctgc atag                                             2004
```

<210> SEQ ID NO 14
<211> LENGTH: 667
<212> TYPE: PRT
<213> ORGANISM: Malbranchea graminicola
<220> FEATURE:
<221> NAME/KEY: MISC_FEATURE
<223> OTHER INFORMATION: MalA' (S129A/P85S) protein
<220> FEATURE:
<221> NAME/KEY: MISC_FEATURE
<222> LOCATION: (85)..(85)
<223> OTHER INFORMATION: MalA' (P85S) variant
<220> FEATURE:
<221> NAME/KEY: MISC_FEATURE
<222> LOCATION: (129)..(129)
<223> OTHER INFORMATION: MalA' (S129A) variant

<400> SEQUENCE: 14

```
Met Ala Pro Thr Pro Lys Tyr Thr Phe Thr Glu Arg Ala Ala Gly
1               5                   10                  15

Asn Leu Ser Asp Ala Glu Ile Leu Asn Ser Asn Asn Pro Thr Gly Ser
            20                  25                  30

Glu Leu Pro Asp Glu Ser Asp Val Val Gly Gly Ala Gly Ile His
        35                  40                  45

Gly Leu Ile Tyr Ala Leu His Ala Ser Lys Tyr Lys Pro Asn Asn Leu
 50                  55                  60

Lys Ile Ser Val Ile Glu Lys Asn Thr Arg Pro Gly Tyr Lys Ile Gly
65                  70                  75                  80

Glu Ser Thr Leu Ser Ile Phe Tyr Thr Trp Cys Lys Leu His Gly Ile
                85                  90                  95

Ser Ala Ala Tyr Leu Leu Arg Leu Phe Gly Leu Lys Asp Gly Leu Cys
            100                 105                 110

Phe Tyr Phe Leu Asp Arg Glu Asn Gln Gly Gln Tyr Thr Asp Phe Cys
        115                 120                 125

Ala Val Gly Ala Pro Gly Leu Val Leu Ala Ser Leu Gln Ile Glu Arg
    130                 135                 140

Pro Met Ser Glu Leu Leu Phe Thr Ile Leu Ala Gln Arg Asn Gly Val
145                 150                 155                 160

Asn Val Tyr His Gly Arg Glu Val Asp Phe Lys Ser Thr Val Val Gln
                165                 170                 175

Gly Gly Gly Gln Gly Asn Lys Ile Ala Val Ser Arg Gly Lys Tyr Asp
            180                 185                 190

Ser Thr Pro Lys Thr Ile Asp Ser Ala Leu Phe Val Asp Ala Thr Gly
        195                 200                 205
```

```
Arg Phe Arg Gln Phe Cys Ser Lys Lys Ala Pro His Arg Phe Asp
    210                 215                 220
Gly Trp Asn Cys Asn Ala Phe Trp Gly Tyr Phe Thr Ala Pro Lys Asp
225                 230                 235                 240
Glu Ser Lys Ile Pro Phe Asp Leu Tyr Glu Gly Asp His Thr Asn His
                245                 250                 255
Leu Cys Phe Pro Glu Gly Trp Val Trp Val Ile Arg Leu Pro Ser Trp
                260                 265                 270
Glu Gly Ser Pro Ile Ala Asn Leu Met Asp Met Val Thr Tyr Ile Leu
            275                 280                 285
Glu Cys Ala Asp Ala Gly Val Pro Gly Asp Glu Leu Pro Ser Ser Glu
290                 295                 300
Glu Leu Ala Arg Met Phe Gly Leu Lys Phe Gln Trp Val Thr Ser Ile
305                 310                 315                 320
Gly Phe Ala Val Arg Asn Asp Val Lys Tyr Pro Glu Asp Leu Ser Ala
                325                 330                 335
Tyr Gly Thr Arg Glu Ala Glu Gln Lys Phe Asn Tyr Phe Val Gln Lys
            340                 345                 350
Tyr Glu Leu Leu Gln Gln Phe Met Ser Asn Phe Glu Leu Ile Glu Asn
            355                 360                 365
Leu Tyr Gly Pro Gly Thr Thr Trp Phe Ile Arg Lys Thr Leu Ala Tyr
            370                 375                 380
Gln Ser Pro Val Val Ser Gly Pro Gly Trp Leu Ala Ile Gly Asp Ala
385                 390                 395                 400
Cys Gly Phe Thr Asn Pro Leu Tyr Ser Pro Gly Ile Asn Val Gly Met
                405                 410                 415
Ser Thr Ser Thr Trp Ala Ala Gln Leu Ser His Pro Ile Val Glu Ile
                420                 425                 430
Gly Lys Ser Ala Pro Ala Asp Ala Ala Glu Ser Ser Ile Arg Lys Leu
            435                 440                 445
Leu Val Pro Tyr Asp Asp Tyr Cys Lys Ser Leu Val Pro Ala Leu Glu
            450                 455                 460
Gln Met Asn Arg Phe Asn Tyr Val Cys Tyr Arg Asp Thr Arg Leu Gly
465                 470                 475                 480
Pro Gln Val Ala Cys Leu Trp Gln Phe Phe Ala Gly Ile Glu Arg Tyr
                485                 490                 495
Leu Ser Asp Val Asn Ile Glu Thr Phe Ala His Tyr Ala Ile Lys Trp
            500                 505                 510
Val Trp Gly Ala Met Val Pro Glu Tyr Gln Gln Val Ala Gln Lys Cys
            515                 520                 525
Ile Glu His Ile Glu Thr Val Pro Leu Asp Glu Arg Leu Pro Asp Ala
            530                 535                 540
Met Val Asp Glu Leu Leu Ala Phe Ser Asn Arg Ile Lys Ser Ala Ala
545                 550                 555                 560
Val Ala Ala Asp Asp Phe Ser Leu Arg Trp Asp Ala Ile Leu Arg Ser
                565                 570                 575
Phe Asp Arg Ser Leu Asn Phe Val Glu Gly Lys Thr Ser Arg Asp Ile
                580                 585                 590
Tyr Thr Arg Gln Cys Ser Gly Cys Gly Ala Trp Leu Gln Leu Arg Pro
            595                 600                 605
Asp Trp Lys Lys Cys His Ser Cys Gly Leu Leu Gly Thr Glu Pro Gln
610                 615                 620
```

```
Thr Ala Val Thr Phe Asp Pro Pro Leu Thr Ala Glu Glu Glu Ala Leu
625                 630                 635                 640

Leu Tyr Ala Ala Trp Asn Thr Ala Pro Lys Tyr Asp Pro Ser Lys Glu
                645                 650                 655

Leu Lys Leu Pro Thr Pro Thr Arg Pro Ala Ala
            660                 665

<210> SEQ ID NO 15
<211> LENGTH: 2004
<212> TYPE: DNA
<213> ORGANISM: Malbranchea aurantiaca
<220> FEATURE:
<221> NAME/KEY: misc_feature
<223> OTHER INFORMATION: MalA (G131S) coding region
<220> FEATURE:
<221> NAME/KEY: misc_feature
<223> OTHER INFORMATION: MalA (G131S) codon variant

<400> SEQUENCE: 15
```

| | | |
|---|---|---|
| atggcgccga caccaaagta tacgtttacc gagagggctg cggcaggcaa tctcagcgac | 60 |
| gctgagattc tcaactccaa taatcctact ggatctgagc tcccagatga atcggatgtg | 120 |
| gtggtgggcg gtgctggtat ccatggtctg atctatgccc ttcacgcttc aaagtataaa | 180 |
| ccgaacaacc tcaagatctc cgttattgag aagaacacta ggcctggtta caagattggc | 240 |
| gagagcactc tacctatctt ttacacctgg tgcaaactcc acggcatctc cgcggcatac | 300 |
| ctccttcgac tattcggact caaggatggg ctgtgctttt actttcttga tcgagagaac | 360 |
| caggggcagt acacagactt ctgcagtgtt tctgctccag gtttggtatt agccagttta | 420 |
| cagattgagc ggccaatgag cgagctgctc tttacaattc ttgcgcaacg aaatggagtc | 480 |
| aatgtctatc acggccggga ggtggatttt aaaagcacgg tggtccaagg gggtggccag | 540 |
| ggcaacaaga tcgcagtctc ccggggcaaa tatgatagca cacccaagac aatagattca | 600 |
| gccctcttcg ttgacgcaac aggccgcttc cgccaatttt gctccaagaa agccccccga | 660 |
| caccgattcg atggatggaa ctgcaacgcc ttctggggtt atttcactgc cccaaaggat | 720 |
| gagagcaaga ttcccttttga tctctatgaa ggtgatcaca caaaccacct gtgttttccg | 780 |
| gaaggttggg tctgggttat tcgtctaccc tcttgggaag ggagcctcat agcgaacttg | 840 |
| atggatatgg tgacatacat actcgaatgc gctgacgccg agtacctggt gatgaactc | 900 |
| ccgagttctg aagagcttgc caggatgttt gggctcaagt ttcagtgggt gacaagtatt | 960 |
| ggctttgccg tgcgcaatga tgtcaagtac ccggaagatc tctcagccta tgggacccgt | 1020 |
| gaggcagagc aaaaattcaa ctactttgtt cagaagtatg agctgcttca gcagttcatg | 1080 |
| tcaaactttg agcttattga aaatctttat ggccctggga ccacatggtt catccgtaag | 1140 |
| acgctggcat accagtctcc agtggtttct ggacctggct ggcttgccat tggtgatgcc | 1200 |
| tgtggtttca ccaacccgct ctattctccg gggattaatg ttggcatgtc gacttcaaca | 1260 |
| tgggccgcac agctttcgca ccgaattgtg agattggga aaagtgcgcc tgcagatgcg | 1320 |
| gcggagtcct ctattcgaaa attactggtc ccatatgacg attattgcaa gtccctagtt | 1380 |
| ccggcactcg agcaaatgaa tcgatttaac tacgtctgtt atcgcgatac acgtttaggt | 1440 |
| ccccaggtgg catgcctctg gcagtttttc gctggcatag agcgatattt gtcagatgtt | 1500 |
| aacattgaaa ccttcgcaca ttacgcgatt aaatgggttt ggggagccat ggtgcctgaa | 1560 |
| tatcaacaag tcgcacagaa atgcattgag catatcgaaa ccgtccccct cgatgagcga | 1620 |
| cttcccgatg cgatggttga tgagttgctt gcgttttcga accgaattaa aagtgctgcc | 1680 |

-continued

```
gtggccgcag acgacttcag tctccggtgg gatgcgatcc tgcgctcttt cgatcggtct    1740
ttgaatttcg tcgaagggaa gacaagcagg gacatctata cgagacaatg ctcgggttgc    1800
ggggcatggc tccaactccg cccagattgg aaaaagtgcc actcatgcgg tcttctgggc    1860
accgagccgc aaacggccgt tacctttgat cccccgctga ccgcagaaga gaaagcgtta    1920
ctttacgctg cctggaatac tgcgcctaaa tacgaccccc tcgaaggagt taaagctacca   1980 accccctacca ggccagctgc atag                                           2004
```

<210> SEQ ID NO 16
<211> LENGTH: 667
<212> TYPE: PRT
<213> ORGANISM: Malbranchea aurantiaca
<220> FEATURE:
<221> NAME/KEY: MISC_FEATURE
<223> OTHER INFORMATION: MalA (G131S) protein
<220> FEATURE:
<221> NAME/KEY: MISC_FEATURE
<222> LOCATION: (131)..(131)
<223> OTHER INFORMATION: MalA (G131S) variant

<400> SEQUENCE: 16

```
Met Ala Pro Thr Pro Lys Tyr Thr Phe Thr Glu Arg Ala Ala Gly
1               5                   10                  15

Asn Leu Ser Asp Ala Glu Ile Leu Asn Ser Asn Asn Pro Thr Gly Ser
            20                  25                  30

Glu Leu Pro Asp Glu Ser Asp Val Val Val Gly Gly Ala Gly Ile His
        35                  40                  45

Gly Leu Ile Tyr Ala Leu His Ala Ser Lys Tyr Lys Pro Asn Asn Leu
    50                  55                  60

Lys Ile Ser Val Ile Glu Lys Asn Thr Arg Pro Gly Tyr Lys Ile Gly
65                  70                  75                  80

Glu Ser Thr Leu Pro Ile Phe Tyr Thr Trp Cys Lys Leu His Gly Ile
                85                  90                  95

Ser Ala Ala Tyr Leu Leu Arg Leu Phe Gly Leu Lys Asp Gly Leu Cys
            100                 105                 110

Phe Tyr Phe Leu Asp Arg Glu Asn Gln Gly Gln Tyr Thr Asp Phe Cys
        115                 120                 125

Ser Val Ser Ala Pro Gly Leu Val Leu Ala Ser Leu Gln Ile Glu Arg
    130                 135                 140

Pro Met Ser Glu Leu Leu Phe Thr Ile Leu Ala Gln Arg Asn Gly Val
145                 150                 155                 160

Asn Val Tyr His Gly Arg Glu Val Asp Phe Lys Ser Thr Val Val Gln
                165                 170                 175

Gly Gly Gly Gln Gly Asn Lys Ile Ala Val Ser Arg Gly Lys Tyr Asp
            180                 185                 190

Ser Thr Pro Lys Thr Ile Asp Ser Ala Leu Phe Val Asp Ala Thr Gly
        195                 200                 205

Arg Phe Arg Gln Phe Cys Ser Lys Lys Ala Pro Arg His Arg Phe Asp
    210                 215                 220

Gly Trp Asn Cys Asn Ala Phe Trp Gly Tyr Phe Thr Ala Pro Lys Asp
225                 230                 235                 240

Glu Ser Lys Ile Pro Phe Asp Leu Tyr Glu Gly Asp His Thr Asn His
                245                 250                 255

Leu Cys Phe Pro Glu Gly Trp Val Trp Val Ile Arg Leu Pro Ser Trp
            260                 265                 270
```

```
Glu Gly Ser Leu Ile Ala Asn Leu Met Asp Met Val Thr Tyr Ile Leu
            275                 280                 285

Glu Cys Ala Asp Ala Gly Val Pro Gly Asp Glu Leu Pro Ser Ser Glu
        290                 295                 300

Glu Leu Ala Arg Met Phe Gly Leu Lys Phe Gln Trp Val Thr Ser Ile
305                 310                 315                 320

Gly Phe Ala Val Arg Asn Asp Val Lys Tyr Pro Glu Asp Leu Ser Ala
                325                 330                 335

Tyr Gly Thr Arg Glu Ala Glu Gln Lys Phe Asn Tyr Phe Val Gln Lys
            340                 345                 350

Tyr Glu Leu Leu Gln Gln Phe Met Ser Asn Phe Glu Leu Ile Glu Asn
        355                 360                 365

Leu Tyr Gly Pro Gly Thr Thr Trp Phe Ile Arg Lys Thr Leu Ala Tyr
    370                 375                 380

Gln Ser Pro Val Val Ser Gly Pro Gly Trp Leu Ala Ile Gly Asp Ala
385                 390                 395                 400

Cys Gly Phe Thr Asn Pro Leu Tyr Ser Pro Gly Ile Asn Val Gly Met
                405                 410                 415

Ser Thr Ser Thr Trp Ala Ala Gln Leu Ser His Arg Ile Val Glu Ile
            420                 425                 430

Gly Lys Ser Ala Pro Ala Asp Ala Ala Glu Ser Ser Ile Arg Lys Leu
        435                 440                 445

Leu Val Pro Tyr Asp Asp Tyr Cys Lys Ser Leu Val Pro Ala Leu Glu
    450                 455                 460

Gln Met Asn Arg Phe Asn Tyr Val Cys Tyr Arg Asp Thr Arg Leu Gly
465                 470                 475                 480

Pro Gln Val Ala Cys Leu Trp Gln Phe Phe Ala Gly Ile Glu Arg Tyr
                485                 490                 495

Leu Ser Asp Val Asn Ile Glu Thr Phe Ala His Tyr Ala Ile Lys Trp
            500                 505                 510

Val Trp Gly Ala Met Val Pro Glu Tyr Gln Gln Val Ala Gln Lys Cys
        515                 520                 525

Ile Glu His Ile Glu Thr Val Pro Leu Asp Glu Arg Leu Pro Asp Ala
    530                 535                 540

Met Val Asp Glu Leu Leu Ala Phe Ser Asn Arg Ile Lys Ser Ala Ala
545                 550                 555                 560

Val Ala Ala Asp Asp Phe Ser Leu Arg Trp Asp Ala Ile Leu Arg Ser
                565                 570                 575

Phe Asp Arg Ser Leu Asn Phe Val Glu Gly Lys Thr Ser Arg Asp Ile
            580                 585                 590

Tyr Thr Arg Gln Cys Ser Gly Cys Gly Ala Trp Leu Gln Leu Arg Pro
        595                 600                 605

Asp Trp Lys Lys Cys His Ser Cys Gly Leu Leu Gly Thr Glu Pro Gln
    610                 615                 620

Thr Ala Val Thr Phe Asp Pro Pro Leu Thr Ala Glu Glu Ala Leu
625                 630                 635                 640

Leu Tyr Ala Ala Trp Asn Thr Ala Pro Lys Tyr Asp Pro Ser Lys Glu
                645                 650                 655

Leu Lys Leu Pro Thr Pro Thr Arg Pro Ala Ala
            660                 665
```

```
<210> SEQ ID NO 17
<211> LENGTH: 2004
<212> TYPE: DNA
<213> ORGANISM: Malbranchea graminicola
<220> FEATURE:
<221> NAME/KEY: misc_feature
<223> OTHER INFORMATION: MalA' (G131S) coding region
<220> FEATURE:
<221> NAME/KEY: misc_feature
<223> OTHER INFORMATION: G131S codon variant

<400> SEQUENCE: 17
```

| | |
|---|---|
| atggcgccga caccaaagta tacgtttacc gagagggctg cggcaggcaa tctcagcgac | 60 |
| gctgagattc tcaactccaa taatcctact ggatctgagc tcccagatga atcggatgtg | 120 |
| gtggtgggcg gtgctggtat ccatggtctg atctatgccc ttcacgcttc aaagtataaa | 180 |
| ccgaacaacc tcaagatctc cgttattgag aagaacacta ggcctggtta caagattggc | 240 |
| gagagcactc tacctatctt ttacacctgg tgcaaactcc acggcatctc cgcggcatac | 300 |
| ctccttcgac tattcggact caaggatggg ctgtgctttt actttcttga tcgagagaac | 360 |
| cagggcagt acacagactt ctgcagtgtt tctgctccag gtttggtatt agccagttta | 420 |
| cagattgagc ggccaatgag cgagctgctc tttacaattc ttgcgcaacg aaatggagtc | 480 |
| aatgtctatc acggccggga ggtggatttt aaaagcacgg tggtccaagg gggtggccag | 540 |
| ggcaacaaga tcgcagtctc ccggggcaaa tatgatagca cacccaagac aatagattca | 600 |
| gccctcttcg ttgacgcaac aggccgcttc cgccaatttt gctccaagaa agccccccga | 660 |
| caccgattcg atggatggaa ctgcaacgcc ttctgggggtt atttcactgc cccaaaggat | 720 |
| gagagcaaga ttcccttga tctctatgaa ggtgatcaca caaaccacct gtgttttccg | 780 |
| gaaggttggg tctgggttat tcgtctaccc tcttgggaag ggagccccat agcgaacttg | 840 |
| atggatatgg tgacatacat actcgaatgc gctgacgccg agtacctggt gatgaactc | 900 |
| ccgagttctg aagagcttgc caggatgttt gggctcaagt ttcagtgggt gacaagtatt | 960 |
| ggctttgccg tgcgcaatga tgtcaagtac ccggaagatc tctcagccta tgggacccgt | 1020 |
| gaggcagagc aaaaattcaa ctactttgtt cagaagtatg agctgcttca gcagttcatg | 1080 |
| tcaaactttg agcttattga aaatctttat ggccctggga ccacatggtt catccgtaag | 1140 |
| acgctggcat accagtctcc agtggtttct ggacctggct ggcttgccat ggtgatgcc | 1200 |
| tgtggtttca ccaacccgct ctattctccg gggattaatg ttggcatgtc gacttcaaca | 1260 |
| tgggccgcac agcttttcgca cccgattgtg gagattggga aagtgcgcc tgcagatgcg | 1320 |
| gcggagtcct ctattcgaaa attactggtc ccatatgacg attattgcaa gtccctagtt | 1380 |
| ccggcactcg agcaaatgaa tcgatttaac tacgtctgtt atcgcgatac acgtttaggt | 1440 |
| ccccaggtgg catgcctctg gcagtttttc gctggcatag agcgatattt gtcagatgtt | 1500 |
| aacattgaaa ccttcgcaca ttacgcgatt aaatgggttt ggggagccat ggtgcctgaa | 1560 |
| tatcaacaag tcgcacagaa atgcattgag catatcgaaa ccgtcccct cgatgagcga | 1620 |
| cttcccgatg cgatggttga tgagttgctt gcgttttcga accgaattaa aagtgctgcc | 1680 |
| gtggccgcag acgacttcag tctccggtgg gatgcgatcc tgcgctcttt cgatcggtct | 1740 |
| ttgaatttcg tcgaagggaa gacaagcagg gacatctata cgagacaatg ctcgggttgc | 1800 |
| ggggcatggc tccaactccg cccagattgg aaaaagtgcc actcatgcgg tcttctgggc | 1860 |
| accgagccgc aaacggccgt taccttttgat cccccgctga ccgcagaaga agaagcgtta | 1920 |

```
ctttacgctg cctggaatac tgcgcctaaa tacgacccct cgaaggagtt aaagctacca    1980
acccctacca ggccagctgc atag                                           2004
```

<210> SEQ ID NO 18
<211> LENGTH: 667
<212> TYPE: PRT
<213> ORGANISM: Malbranchea graminicola
<220> FEATURE:
<221> NAME/KEY: MISC_FEATURE
<223> OTHER INFORMATION: MalA' (G131S) protein
<220> FEATURE:
<221> NAME/KEY: MISC_FEATURE
<222> LOCATION: (131)..(131)
<223> OTHER INFORMATION: MalA' (G131S) variant

<400> SEQUENCE: 18

```
Met Ala Pro Thr Pro Lys Tyr Thr Phe Thr Glu Arg Ala Ala Gly
1               5                   10                  15

Asn Leu Ser Asp Ala Glu Ile Leu Asn Ser Asn Asn Pro Thr Gly Ser
            20                  25                  30

Glu Leu Pro Asp Glu Ser Asp Val Val Gly Gly Ala Gly Ile His
        35                  40                  45

Gly Leu Ile Tyr Ala Leu His Ala Ser Lys Tyr Lys Pro Asn Asn Leu
 50                  55                  60

Lys Ile Ser Val Ile Glu Lys Asn Thr Arg Pro Gly Tyr Lys Ile Gly
65                  70                  75                  80

Glu Ser Thr Leu Pro Ile Phe Tyr Thr Trp Cys Lys Leu His Gly Ile
                85                  90                  95

Ser Ala Ala Tyr Leu Leu Arg Leu Phe Gly Leu Lys Asp Gly Leu Cys
            100                 105                 110

Phe Tyr Phe Leu Asp Arg Glu Asn Gln Gly Gln Tyr Thr Asp Phe Cys
        115                 120                 125

Ser Val Ser Ala Pro Gly Leu Val Leu Ala Ser Leu Gln Ile Glu Arg
    130                 135                 140

Pro Met Ser Glu Leu Leu Phe Thr Ile Leu Ala Gln Arg Asn Gly Val
145                 150                 155                 160

Asn Val Tyr His Gly Arg Glu Val Asp Phe Lys Ser Thr Val Val Gln
                165                 170                 175

Gly Gly Gly Gln Gly Asn Lys Ile Ala Val Ser Arg Gly Lys Tyr Asp
            180                 185                 190

Ser Thr Pro Lys Thr Ile Asp Ser Ala Leu Phe Val Asp Ala Thr Gly
        195                 200                 205

Arg Phe Arg Gln Phe Cys Ser Lys Lys Ala Pro Arg His Arg Phe Asp
    210                 215                 220

Gly Trp Asn Cys Asn Ala Phe Trp Gly Tyr Phe Thr Ala Pro Lys Asp
225                 230                 235                 240

Glu Ser Lys Ile Pro Phe Asp Leu Tyr Glu Gly Asp His Thr Asn His
                245                 250                 255

Leu Cys Phe Pro Glu Gly Trp Val Trp Val Ile Arg Leu Pro Ser Trp
            260                 265                 270

Glu Gly Ser Pro Ile Ala Asn Leu Met Asp Met Val Thr Tyr Ile Leu
        275                 280                 285

Glu Cys Ala Asp Ala Gly Val Pro Gly Asp Glu Leu Pro Ser Ser Glu
    290                 295                 300

Glu Leu Ala Arg Met Phe Gly Leu Lys Phe Gln Trp Val Thr Ser Ile
305                 310                 315                 320
```

```
Gly Phe Ala Val Arg Asn Asp Val Lys Tyr Pro Glu Asp Leu Ser Ala
            325                 330                 335

Tyr Gly Thr Arg Glu Ala Glu Gln Lys Phe Asn Tyr Phe Val Gln Lys
        340                 345                 350

Tyr Glu Leu Leu Gln Gln Phe Met Ser Asn Phe Glu Leu Ile Glu Asn
    355                 360                 365

Leu Tyr Gly Pro Gly Thr Thr Trp Phe Ile Arg Lys Thr Leu Ala Tyr
370                 375                 380

Gln Ser Pro Val Val Ser Gly Pro Gly Trp Leu Ala Ile Gly Asp Ala
385                 390                 395                 400

Cys Gly Phe Thr Asn Pro Leu Tyr Ser Pro Gly Ile Asn Val Gly Met
            405                 410                 415

Ser Thr Ser Thr Trp Ala Ala Gln Leu Ser His Pro Ile Val Glu Ile
        420                 425                 430

Gly Lys Ser Ala Pro Ala Asp Ala Ala Glu Ser Ser Ile Arg Lys Leu
    435                 440                 445

Leu Val Pro Tyr Asp Asp Tyr Cys Lys Ser Leu Val Pro Ala Leu Glu
450                 455                 460

Gln Met Asn Arg Phe Asn Tyr Val Cys Tyr Arg Asp Thr Arg Leu Gly
465                 470                 475                 480

Pro Gln Val Ala Cys Leu Trp Gln Phe Phe Ala Gly Ile Glu Arg Tyr
            485                 490                 495

Leu Ser Asp Val Asn Ile Glu Thr Phe Ala His Tyr Ala Ile Lys Trp
        500                 505                 510

Val Trp Gly Ala Met Val Pro Glu Tyr Gln Gln Val Ala Gln Lys Cys
    515                 520                 525

Ile Glu His Ile Glu Thr Val Pro Leu Asp Glu Arg Leu Pro Asp Ala
530                 535                 540

Met Val Asp Glu Leu Leu Ala Phe Ser Asn Arg Ile Lys Ser Ala Ala
545                 550                 555                 560

Val Ala Ala Asp Asp Phe Ser Leu Arg Trp Asp Ala Ile Leu Arg Ser
            565                 570                 575

Phe Asp Arg Ser Leu Asn Phe Val Glu Gly Lys Thr Ser Arg Asp Ile
        580                 585                 590

Tyr Thr Arg Gln Cys Ser Gly Cys Gly Ala Trp Leu Gln Leu Arg Pro
    595                 600                 605

Asp Trp Lys Lys Cys His Ser Cys Gly Leu Leu Gly Thr Glu Pro Gln
610                 615                 620

Thr Ala Val Thr Phe Asp Pro Pro Leu Thr Ala Glu Glu Ala Leu
625                 630                 635                 640

Leu Tyr Ala Ala Trp Asn Thr Ala Pro Lys Tyr Asp Pro Ser Lys Glu
            645                 650                 655

Leu Lys Leu Pro Thr Pro Thr Arg Pro Ala Ala
        660                 665

<210> SEQ ID NO 19
<211> LENGTH: 35
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Malbranchea aurantiaca malA forward primer
      (malA-F)
```

<400> SEQUENCE: 19
gagagctagc atggcgccga caccaaagta tacgt         35

<210> SEQ ID NO 20
<211> LENGTH: 35
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Malbranchea aurantiaca malA reverse primer
      (malA-R)

<400> SEQUENCE: 20
cattaagctt ctatgcagct ggcctggtag gggtt         35

<210> SEQ ID NO 21
<211> LENGTH: 33
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: R428P Forward

<400> SEQUENCE: 21
gcacagcttt cgcacccaat tgtggagatt ggg           33

<210> SEQ ID NO 22
<211> LENGTH: 33
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: R428P Reverse

<400> SEQUENCE: 22
cccaatctcc acaattgggt gcgaaagctg tgc           33

<210> SEQ ID NO 23
<211> LENGTH: 49
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: L276P

<400> SEQUENCE: 23
cgtctaccct cttgggaagg gagccccata gcgaacttga tggatatgg   49

<210> SEQ ID NO 24
<211> LENGTH: 40
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: MalA K108A Synthetic Primer

<400> SEQUENCE: 24
gtaaaagcac agcccatccg cgagtccgaa tagtcgaagg    40

```
<210> SEQ ID NO 25
<211> LENGTH: 41
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: S409A primer

<400> SEQUENCE: 25
ggtttcacca acccgctcta tgccccgggg attaatgttg g                             41

<210> SEQ ID NO 26
<211> LENGTH: 48
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: S82A primer

<400> SEQUENCE: 26
cctggttaca agattggcga ggcgactcta cctatctttt acacctgg                      48

<210> SEQ ID NO 27
<211> LENGTH: 53
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: E494A primer

<400> SEQUENCE: 27
ggcagttttt cgctggcata gcgcgatatt tgtcagatgt taacattgaa acc                53

<210> SEQ ID NO 28
<211> LENGTH: 53
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: E494Q primer

<400> SEQUENCE: 28
ggcagttttt cgctggcata cagcgatatt tgtcagatgt taacattgaa acc                53

<210> SEQ ID NO 29
<211> LENGTH: 53
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: W263A primer

<400> SEQUENCE: 29
ccacctgtgt tttccggaag gtgctgtctg ggttattcgt ctaccctctt ggg                53

<210> SEQ ID NO 30
<211> LENGTH: 53
<212> TYPE: DNA
<213> ORGANISM: Artificial Sequence
```

```
<220> FEATURE:
<223> OTHER INFORMATION: Synthetic Primer
<220> FEATURE:
<221> NAME/KEY: misc_feature
<223> OTHER INFORMATION: W265A primer

<400> SEQUENCE: 30
ccacctgtgt tttccggaag gttgggtcgc ggttattcgt ctaccctctt ggg          53

<210> SEQ ID NO 31
<211> LENGTH: 47
<212> TYPE: DNA
<213> ORGANISM: Artificial Sequence
<220> FEATURE:
<223> OTHER INFORMATION: Sythetic Primer
<220> FEATURE:
<221> NAME/KEY: misc_feature
<223> OTHER INFORMATION: H253A primer

<400> SEQUENCE: 31
ccctttgatc tctatgaagg tgatgcgaca aaccacctgt gttttcc              47

<210> SEQ ID NO 32
<211> LENGTH: 44
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: F489H primer

<400> SEQUENCE: 32
ccccaggtgg catgcctctg gcagcatttc gctggcatag agcg                  44

<210> SEQ ID NO 33
<211> LENGTH: 47
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: C613S/C616S primer

<400> SEQUENCE: 33
ccgcccagat tggaaaaagt ctcactcatc tggtcttctg ggcaccg               47

<210> SEQ ID NO 34
<211> LENGTH: 46
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: C112S primer

<400> SEQUENCE: 34
ggactcaagg atgggctgtc tttttacttt cttgatcgag agaacc                46

<210> SEQ ID NO 35
<211> LENGTH: 44
<212> TYPE: DNA
<213> ORGANISM: Artificial Sequence
<220> FEATURE:
<223> OTHER INFORMATION: Synthetic Primer
```

-continued

```
<220> FEATURE:
<221> NAME/KEY: misc_feature
<223> OTHER INFORMATION: C128S primer

<400> SEQUENCE: 35
ggggcagtac acagacttct ctagtgttgg ggctccaggt ttgg            44

<210> SEQ ID NO 36
<211> LENGTH: 53
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: E494D primer

<400> SEQUENCE: 36
ggcagttttt cgctggcata gatcgatatt tgtcagatgt taacattgaa acc            53

<210> SEQ ID NO 37
<211> LENGTH: 47
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: H253F primer

<400> SEQUENCE: 37
ccctttgatc tctatgaagg tgattttaca aaccacctgt gttttcc            47

<210> SEQ ID NO 38
<211> LENGTH: 44
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: S129A primer

<400> SEQUENCE: 38
ggggcagtac acagacttct gcgcggttgg ggctccaggt ttgg            44

<210> SEQ ID NO 39
<211> LENGTH: 51
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: D129A primer

<400> SEQUENCE: 39
ccttcgacta ttcggactca aggcggggct gtgcttttac tttcttgatc g            51
```

US 11,008,553 B2

HALOGENATION OF COMPLEX ORGANIC COMPOUNDS

CROSS-REFERENCE TO RELATED APPLICATIONS

This application claims the priority benefit under 35 U.S.C. § 119(e) of U.S. Provisional Application No. 62/700,152, filed Jul. 18, 2018, the disclosure of which is incorporated herein by reference in its entirety.

STATEMENT OF GOVERNMENT SUPPORT

This invention was made with government support under CA070375 awarded by the National Institutes of Health and CHE1205646 awarded by the National Science Foundation. The government has certain rights in the invention.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "53295A_Seqlisting.txt", which was created on Jul. 18, 2019 and is 84,638 bytes in size. The subject matter of the Sequence Listing is incorporated herein in its entirety by reference.

FIELD

The disclosure relates generally to the field of complex chemistry and more particularly to biocatalysis of compound halogenation.

BACKGROUND

The prevalence of halogenated natural products has led to significant advances in understanding various classes of halogenases involved in secondary metabolism. Most halogenases characterized thus far can be placed into three classes: haloperoxidases (heme-containing and vanadium-containing), non-heme Fe(II)α-ketoglutarate-dependent, and flavin-dependent enzymes. Haloperoxidases are generally nonselective and perform halogenation through a mechanism utilizing freely diffusing hypohalous acid. By contrast, Fe(II)α-ketoglutarate-dependent halogenases proceed through a radical mechanism, typically halogenating aliphatic, unactivated carbons.[1] Flavin-dependent halogenases (FDHs) also proceed through a hypohalous acid intermediate, with the reactive reagent captured by a lysine residue that appears to control the regioselectivity of halogenation on aromatic substrates.[2,3] The FDH-derived hypohalous acid is generated through a reaction between the flavin C4a-peroxide adduct and the bound chloride ion. FDHs are thought to proceed through an electrophilic aromatic substitution (EAS) where the catalytic lysine residue provides the chloramine halogenating agent and a catalytic glutamate facilitates the reaction by deprotonating the positively charged intermediate generated during catalysis.[2]

The majority of previously characterized FDHs are of bacterial origin, with relatively few reported from eukaryotes,[4-12] and fewer still characterized biochemically.[4-6,10-12] The bacterial FDHs have been found to catalyze reactions on both free,[2,13-15] and carrier-protein-bound substrates,[16,17] including precursor amino acids in natural product biosynthesis. The well-characterized eukaryotic FDHs Rdc24 and ChlA6 catalyze late-stage C—H functionalization reactions in the biosynthesis of halogenated metabolites. However, structural data for these two enzymes have not been reported, and it has remained unclear how they control site-selective halogenation on large, structurally complex substrates.

Malbrancheamide (compound 1) is a complex halogenated indole alkaloid produced by the terrestrial fungus *Malbranchea aurantiaca* RRC181318 and the marine sponge-derived fungus *Malbranchea graminicola* 086937A.[19] The discovery of malbrancheamide was enabled by a search for calmodulin antagonists, and several studies have characterized its significant vasorelaxant effect.[20,21] Along with malbrancheamide, a close structural relative, spiromalbramide, was isolated from *M. graminicola*.[19] The two strains are highly related, with 99% sequence identity overall, and their biosynthetic pathways for malbrancheamide are proposed to be identical (Scheme 1). Malbrancheamide (compound 1) belongs to a family of prenylated indole alkaloids formed through peptide coupling by a nonribosomal peptide synthetase (NRPS), addition of an isoprene unit by a prenyltransferase, and a proposed [4+2] Diels-Alder cycloaddition to form the characteristic bicyclo[2.2.2]diazaoctane ring of premalbrancheamide (compound 2) (Scheme 1).[22-26] Premalbrancheamide is then proposed to be dichlorinated through an iterative mechanism, but whether this halogenation is performed by one or two halogenases remained to be determined.[25] The chlorination of the indole ring differentiates this molecule from the rest of its class and significantly contributes to its biological activity.[21]

In earlier efforts to elucidate the malbrancheamide biosynthetic pathway, precursor incorporation studies were performed in *M. aurantiaca*. This led to the conclusion that premalbrancheamide (compound 2) is indeed incorporated into the monochlorinated malbrancheamide B (compound 3) and that both compounds are natural metabolites of *M. aurantiaca*.[25] Previously, it had been proposed that there is a site-selective chlorination of the C9 position prior to functionalization of C8 for production of malbrancheamide (compound 1).[25] The isolation of both C8 (isomalbrancheamide B (compound 4)) and C9 (malbrancheamide B (compound 3)) monohalogenated metabolites from *M. aurantiaca*[20] and from *M. graminicola*[19], however, conflicted with the proposed C9 selectivity hypothesis.

The ability to selectively halogenate C—H bonds in highly complex molecules through synthetic methods has posed a formidable challenge due to the abundance of chemically equivalent C—H bonds, and the inability to overcome inherent steric or electronic bias for reactivity.[31,32] The large number of biologically active natural products that undergo late-stage functionalization by tailoring enzymes provides a unique opportunity to leverage the power of halogenating enzymes to perform difficult chemical transformations.

In view of the foregoing observations, a need continues to exist in the art for catalysts that modify complex compounds, for example the controlled halogenation of complex compounds such as indole alkaloids.

SUMMARY

The disclosure provides flavin-dependent halogenases (FDHs) that are amino acid variants of fungal MalA or MalA' halogenases useful in specifically halogenating complex compounds such as indole alkaloids. These enzymes are useful in producing a variety of halogenated compounds in the fungal malbrancheamide pathway that have physiological effects in mammals such as inhibiting calmodulin and, thereby, modulating calcium ion signaling pathways involved in a diverse set of physiological pathways and, hence, a variety of diseases or disorders. Exemplary methods comprising administration of effective amounts of the compounds disclosed herein include inhibiting the contraction of smooth muscle in a mammal.

In one aspect, the disclosure provides a flavin-dependent halogenase (FDH) variant comprising one or two amino acid substitutions compared to the amino acid sequence set forth in SEQ ID NO:2 or SEQ ID NO:4, wherein the FDH variant is capable of catalyzing the halogenation of a complex organic compound. In some embodiments, the complex organic compound is an aromatic heterocyclic organic compound. In some embodiments, the aromatic heterocyclic organic compound comprises a bicyclo[2.2.2]diazaoctane ring. In some embodiments, the aromatic heterocyclic organic compound comprises indole. In some embodiments, the compound is an indole alkaloid. In some embodiments, the indole alkaloid is a prenylated indole alkaloid. In some embodiments, the FDH variant is derived from a fungal FDH. In some embodiments, the FDH variant is derived from a bacterial FDH. In some embodiments, the FDH variant is not derived from a fungal FDH or a bacterial FDH.

In some embodiments, the FDH variant is a MalA halogenase variant. In some embodiments, the FDH variant comprises an amino acid substitution variant of the sequence set forth in SEQ ID NO:2, wherein the substitution is S129Z, H253Z, S129Z/H253Z, D109Z, F489Z, S409Z, W265Z, W263Z, S82Z, S129Z/G131Z, G131Z, S129Z/I493Z, I493Z, S129Z/P85Z, or P85Z, wherein Z is no amino acid or any conventional amino acid except the wild-type amino acid at the indicated position. In the context of the disclosure, a substitution mutation or variation at the amino acid level is expressly defined as including the substitution of any naturally occurring conventional amino acid for a non-identical amino acid, or the substitution of no amino acid for a given amino acid, i.e., a single amino acid deletion. In some embodiments, the FDH variant comprises an amino acid substitution variant of the sequence set forth in SEQ ID NO:2, wherein the substitution is S129A, H253F, S129A/H253F, H253A, D109A, F489H, S409A, W265A, W263A, S82A, S129A/G131S, G131S, S129A/I4935, I493S, S129A/P85S, or P85S. In some embodiments, the MalA halogenase comprises the sequence set forth in SEQ ID NO:6, 8, 12, or 16. In some embodiments, the FDH variant is a MalA' halogenase variant. In some embodiments, the FDH variant comprises an amino acid substitution variant of the sequence set forth in SEQ ID NO:4, wherein the substitution is E494Z or H253Z, wherein Z is no amino acid or any conventional amino acid except the wild-type amino acid at the indicated position. In some embodiments, the FDH variant comprises an amino acid substitution variant of the sequence set forth in SEQ ID NO:4, wherein the substitution is E494D, H253F, S129A, S129A/I493S, I493S, S129A/P85S, P85S, S129A/G131S, or G131S. In some embodiments, the MalA' halogenase comprises the sequence set forth in SEQ ID NO:10, 14, or 18.

Another aspect of the disclosure is drawn to a polynucleotide encoding a FDH variant disclosed herein. In some embodiments, the encoded FDH variant is a MalA halogenase variant or a MalA' halogenase variant. In some embodiments, the encoded FDH variant comprises a sequence set forth in SEQ ID NO:6, 8, 10, 12, 14, 16, or 18.

Yet another aspect of the disclosure is directed to a vector comprising the polynucleotide disclosed herein. A related aspect of the disclosure is a host cell comprising the polynucleotide disclosed herein or the vector disclosed herein.

Another aspect of the disclosure is a malbrancheamide D compound comprising formula I:

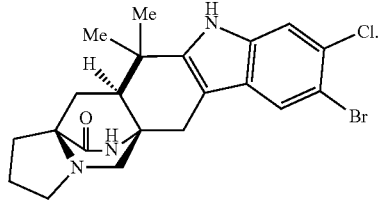

I

A related aspect of the disclosure is an isomalbrancheamide D compound comprising formula II:

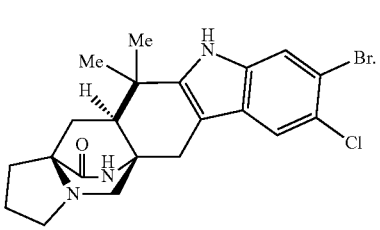

II

A related aspect of the disclosure is a malbrancheamide E compound comprising formula III:

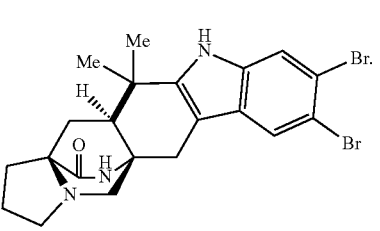

III

Still another aspect of the disclosure is a method of halogenating a complex organic compound comprising contacting a complex organic compound with a FDH halogenase variant disclosed herein and a halogen under conditions suitable for enzyme-catalyzed halogenation of the complex organic compound. In some embodiments, the complex organic compound is an aromatic heterocyclic organic compound. In some embodiments, the aromatic heterocyclic organic compound comprises a bicyclo[2.2.2]diazaoctane ring. In some embodiments, the aromatic heterocyclic organic compound comprises indole. In some embodiments, the compound is an indole alkaloid. In some embodiments, the indole alkaloid is a prenylated indole alkaloid. In some embodiments, the prenylated indole alkaloid is derived from a *Malbranchea* species. In some embodiments, the *Malbranchea* species is *Malbranchea aurantiaca* or *Malbranchea graminicola*. In some embodiments of the method, the prenylated indole alkaloid is premalbrancheamide, malbrancheamide B, isomalbrancheamide B, malbrancheamide C, or isomalbrancheamide C. In some embodiments, the halogenation step is a chlorination step. In some embodiments, the halogenation step is a bromination step.

Another aspect of the disclosure is drawn to a method of modulating a $Ca^{2+}$ signaling pathway in a cell of a mammal or a cell in vitro comprising administering an effective amount of a halogenated complex organic compound to the mammal, the cell in vitro, or to the isolated enzyme or enzymes in vitro. Some embodiments implement a method of modulating a $Ca^{2+}$ signaling pathway in a cell of a mammal comprising administering an effective amount of a halogenated complex organic compound to the mammal. In some embodiments, the $Ca^{2+}$ signaling pathway is a $Ca^{2+}$-calmodulin dependent pathway. In some embodiments, modulating the $Ca^{2+}$ signaling pathway inhibits smooth muscle contraction. In some embodiments, the halogenated complex organic compound is malbrancheamide, malbrancheamide B, isomalbrancheamide B, malbrancheamide C, isomalbrancheamide C, malbrancheamide D, isomalbrancheamide D, or malbrancheamide E.

Some embodiments implement a method of modulating a $Ca^{2+}$ signaling pathway in a cell, such as a mammalian cell, in vitro or in an isolated enzyme or enzymes in vitro comprising administering an effective amount of a halogenated complex organic compound to the cell in vitro or to the isolated enzyme or enzymes in vitro. Some embodiments provide a method of modulating a $Ca^{2+}$ signaling pathway in a cell in vitro comprising administering an effective amount of a halogenated complex organic compound to the cell in vitro. In some embodiments, the $Ca^{2+}$ signaling pathway is a $Ca^{2+}$-calmodulin dependent pathway. In some embodiments, the $Ca^{2+}$ signaling pathway being modulated in vitro participates in smooth muscle contraction in vivo. In some embodiments, the halogenated complex organic compound is malbrancheamide, malbrancheamide B, isomalbrancheamide B, malbrancheamide C, isomalbrancheamide C, malbrancheamide D, isomalbrancheamide D, or malbrancheamide E. Some embodiments implement a method of modulating a $Ca^{2+}$ signaling pathway comprising administering an effective amount of a halogenated complex organic compound to an isolated enzyme or enzymes. In some embodiments, the $Ca^{2+}$ signaling pathway is a $Ca^{2+}$-calmodulin dependent pathway. In some embodiments, the $Ca^{2+}$ signaling pathway being modulated in vitro participates in smooth muscle contraction in vivo. In some embodiments, the halogenated complex organic compound is malbrancheamide, malbrancheamide B, isomalbrancheamide B, malbrancheamide C, isomalbrancheamide C, malbrancheamide D, isomalbrancheamide D, or malbrancheamide E.

Other features and advantages of the disclosure will be better understood by reference to the following detailed description, including the drawing and the examples.

DETAILED DESCRIPTION

The fungal genus *Malbranchea* includes species such as *M aurantiaca* and *M. graminicola* that contain biosynthetic pathways for the production of complex halogenated compounds such a halogenated indole alkaloids that have useful physiological effects such as being useful in modulating Calcium ion signaling pathways in mammalian cells involved in many physiological functions and implicated in a variety of diseases and disorders. The disclosure provides variants of fungal halogenases such as the MalA halogenase of *M. aurantiaca* and the MalA' halogenase of *M. graminicola* that catalyze the synthesis of complex halogenated compounds useful, e.g., in inhibiting smooth muscle contraction. The data provide a comprehensive characterization of the fungal halogenase variants and provide extensive characterizations of the structure and properties of the compounds used as substrates or produced by the halogenase variants, which generally fall into the malbrancheamide synthetic pathways of the *Malbranchea* fungal species.

Figure 1:
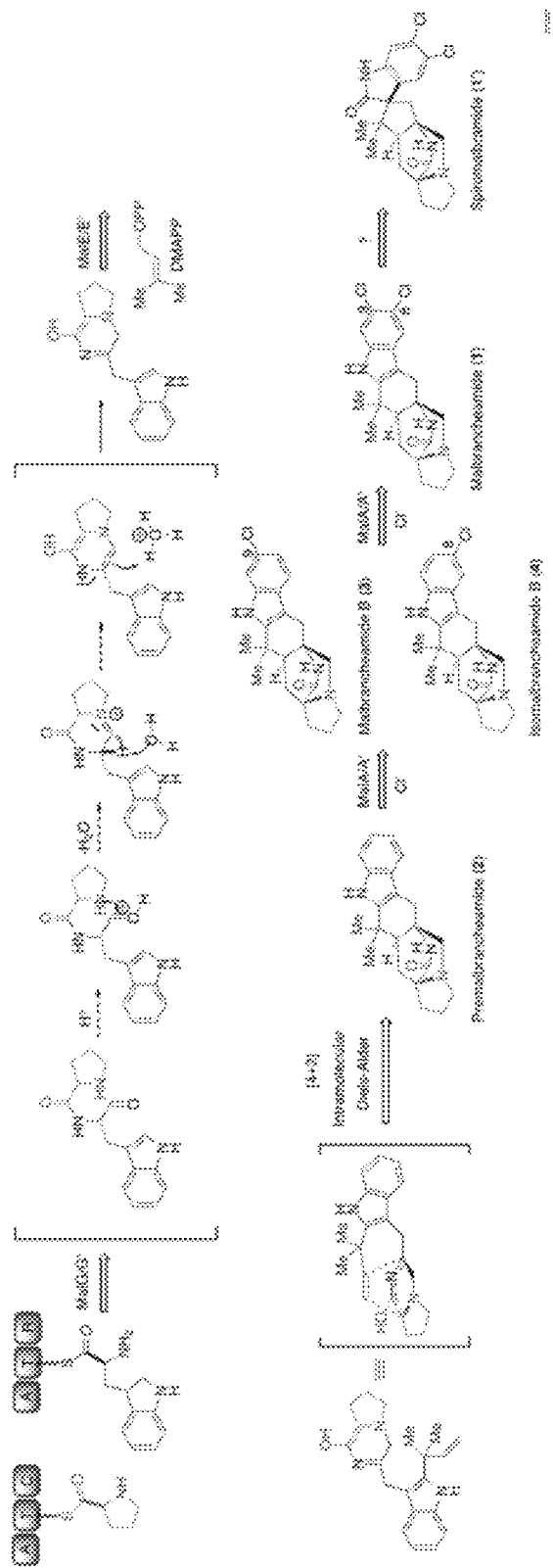
FIG. 1. Scheme 1. Malbrancheamide biosynthetic pathway in *M. aurantiaca* and *M. graminicola*, where spiromalbramide is produced only in the latter.
Figure 3:
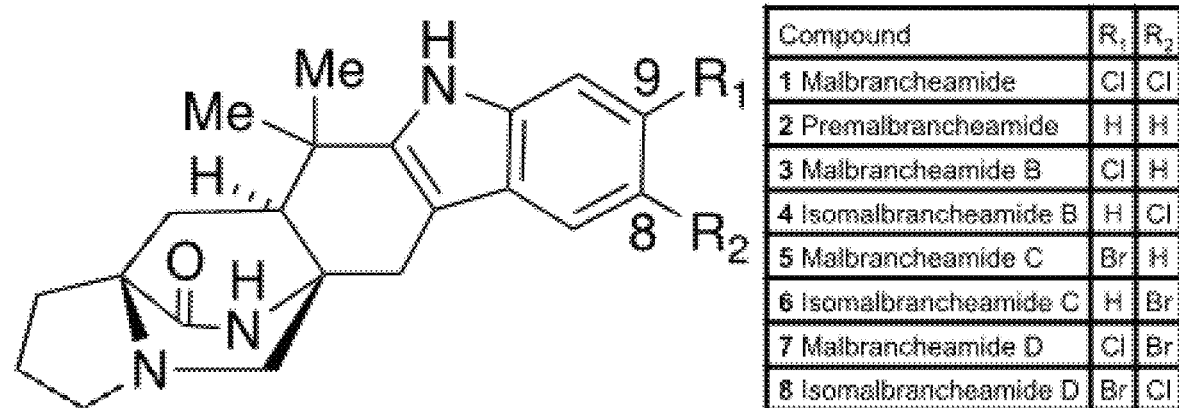
FIG. 3. Malbrancheamide and related metabolites. *M. aurantiaca* isolates included compounds 1, 2, 3, and 4, while *M. graminicola* also produced compounds 5 and 6. Compounds 7 and 8 had not been previously described from either organism. See FIG. 1 for compound identities.

The experiments disclosed herein were designed to identify and characterize the versatile halogenases involved in malbrancheamide biosynthesis and to demonstrate their potential as biocatalysts for halogenation of complex organic compounds, including various compounds found in the malbrancheamide pathway, such as premalbrancheamide (compound 2) and both mono- and di-halogenated malbrancheamide pathway compounds including malbrancheamide B (compound 3), isomalbrandheamide B (compound 4), malbrancheamide C, isomalbrancheamide C, malbrancheamide D, and isomalbrancheamide D (see FIGS. 1 and 3). The experiments probe the mechanism of the iterative late-stage halogenation of premalbrancheamide at two adjacent positions on the indole ring system. The isolation of both C8 (isomalbrancheamide B (compound 4)) and C9 (malbrancheamide B (compound 3)) monohalogenated metabolites from *M. aurantiaca*[20] and from *M. graminicola*[19] conflicted with the proposed C9 selectivity hypothesis, providing further motivation to investigate the malbrancheamide halogenation process.

Figure 2:
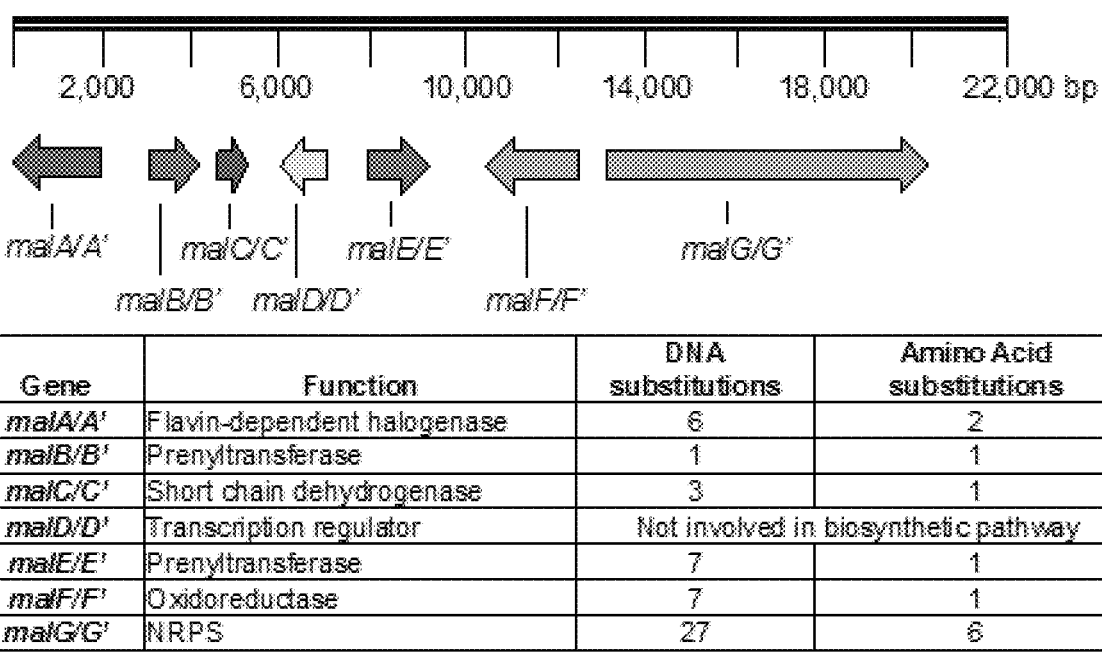
FIG. 2. Malbrancheamide biosynthetic gene clusters in *M. aurantiaca* and *M. graminicola*.

Genome sequencing and bioinformatic analyses of *M. aurantiaca* and *M. graminicola* led to the identification of MalA and MalA', respectively. These two FDHs are 99% identical, differing by only two amino acids, and are proposed to catalyze dihalogenation as the last step in the malbrancheamide biosynthetic pathways of each organism (FIG. 2).[26] The late-stage halogenation of free substrate by a flavin-dependent halogenase from an NRPS-containing gene cluster is unusual. Halogenation typically occurs as the first step prior to activation of an amino acid in bacterial non-ribosomal peptide biosynthesis.[1] Of the previously characterized flavin-dependent halogenases, most act on subunit substrates such as single amino acids,[2,13-15,27] or carrier protein-tethered small molecules.[16,17,28,29] In terms of late-stage activity on a complex polycyclic substrate, the closest comparison to MalA is the cyanobacterial-derived WelO5 non-heme Fe(II)α-ketoglutarate-dependent halogenase, which acts on fischerindole and hapalindole alkaloids.[30] In addition to substrate scope analyses, halogen selectivity has also been explored in flavin-dependent halogenases, and the majority were found to catalyze both chlorination and bromination reactions. In precursor incorporation studies using high bromide salt concentrations in the marine fungal strain *M. graminicola*, bromination of premalbrancheamide (compound 2) led to the production of malbrancheamide C (5) and isomalbrancheamide C (compound 6) (FIG. 3).[19]

Malbrancheamide is a dichlorinated fungal indole alkaloid isolated from both *Malbranchea aurantiaca* and *Malbranchea graminicola* that belongs to a family of natural products containing a characteristic bicyclo[2.2.2]diazaoctane core. The introduction of chlorine atoms on the indole ring of malbrancheamide differentiates it from other members of this family and contributes significantly to its biological activity. The two flavin-dependent halogenases involved in the late-stage halogenation of malbrancheamide in two different fungal strains have been characterized. MalA and MalA' catalyze the iterative dichlorination and monobromination of the free substrate premalbrancheamide as the final steps in the malbrancheamide biosynthetic pathway. Two unnatural bromo-chloro-malbrancheamide analogs were generated through MalA-mediated chemoenzymatic synthesis. Structural analysis and computational studies of MalA' in complex with three substrates revealed that the enzyme represents a new class of zinc-binding flavin-dependent halogenases, and provides new insights into a reaction mechanism that is expected to be unique.

Figure 13:
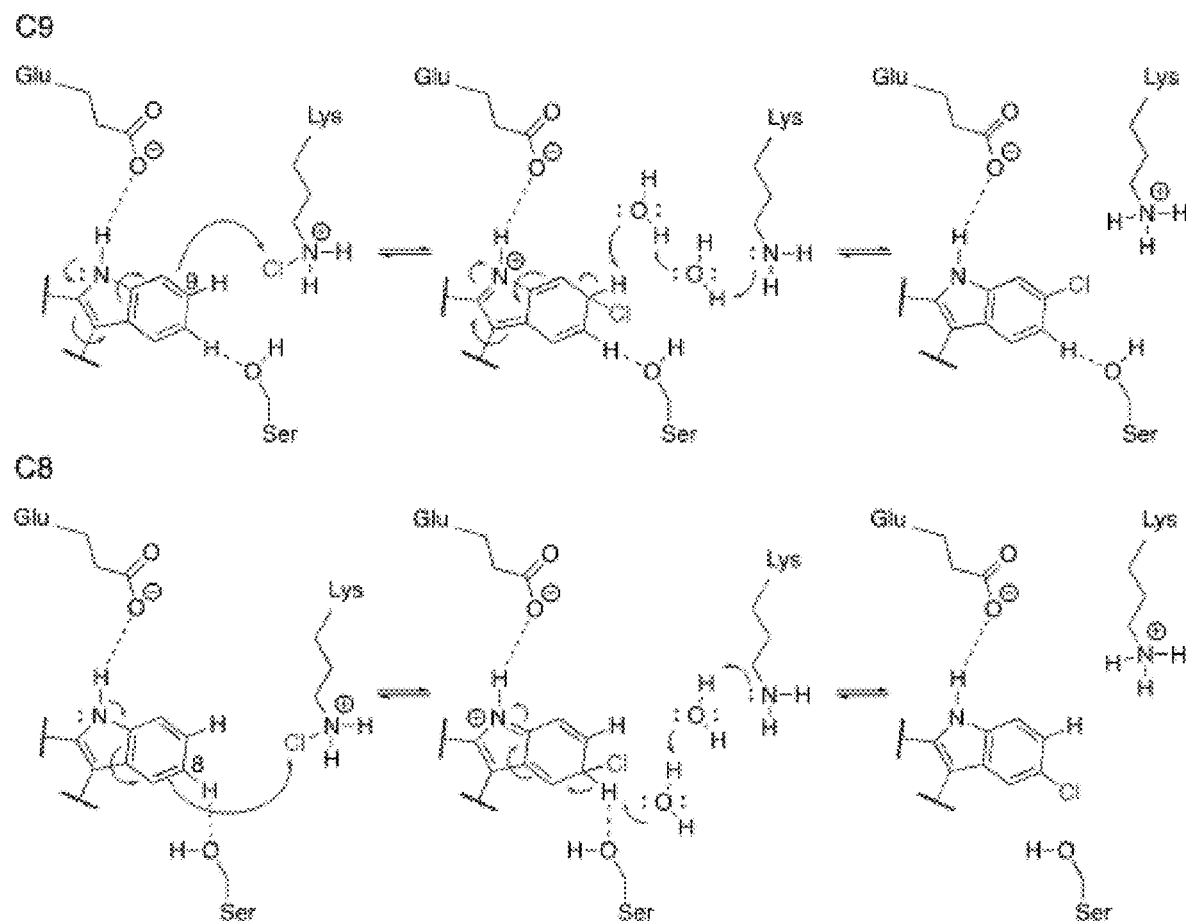
FIG. 13. Scheme 2. Proposed mechanism for MalA catalysis.
Figure 14:
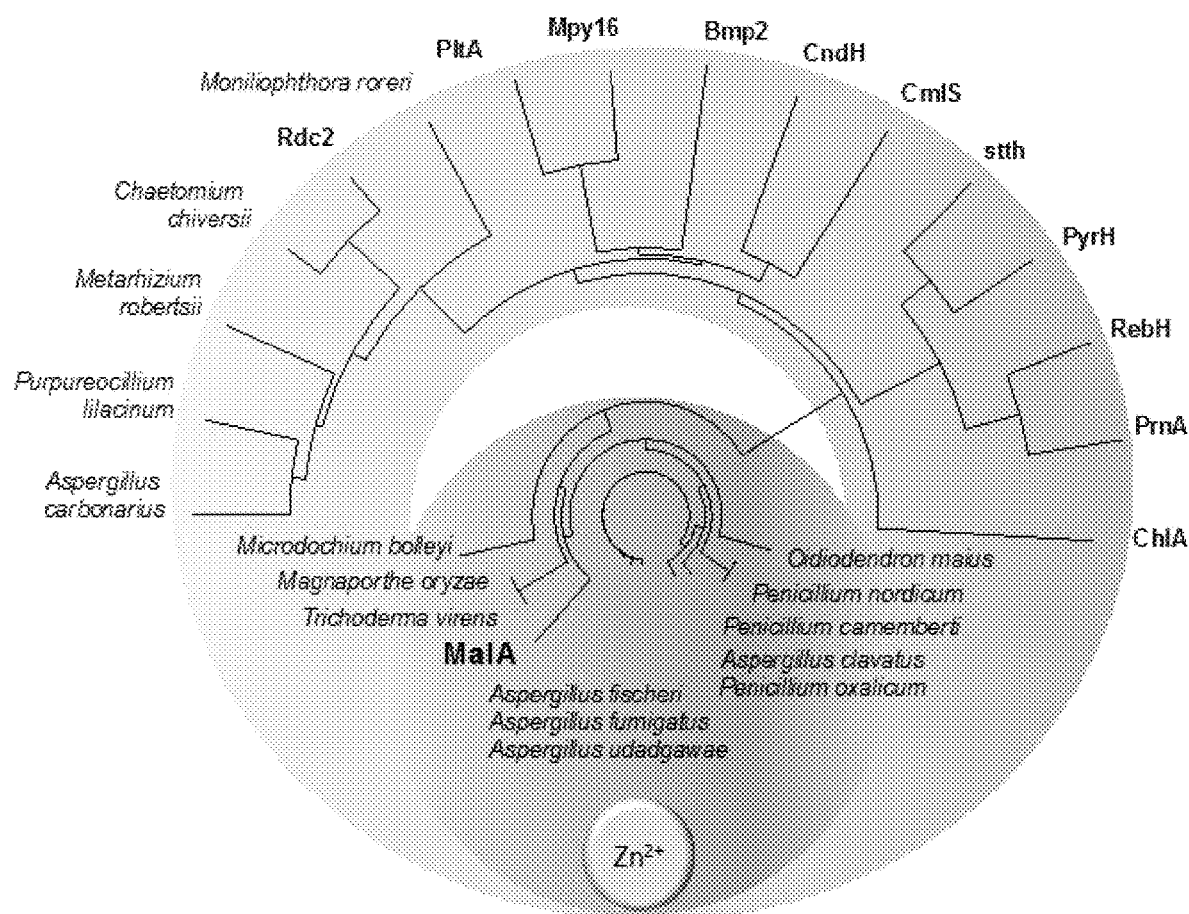
FIG. 14. Phylogenetic tree of characterized and uncharacterized (labeled with producing organism) FDHs. Putative fungal FDHs with high amino acid identity (greater than 50%) to the MalA cluster in the blue region are expected to contain the $Zn^{2+}$-binding motif based on sequence alignments. The green region contains previously characterized bacterial FDHs (the exception is the eukaryotic ChlA) and the yellow region denotes a new subclass of putative FDHs from fungi. Phylogenetic tree prepared using Lasergene MegAlignPro (DNASTAR).[40]

The experimental results disclosed herein provide an example of a unique subclass of flavin-dependent halogenases that performs iterative late-stage halogenation of complex substrates independent of a carrier protein. MalA is encoded in a gene cluster containing a Non-Ribosomal Peptide Synthetase (NRPS), but the evidence provided herein demonstrates that this protein catalyzes effective late-stage functionalization on free substrates. The data lead to the expectation of a new mechanism, involving Ser129, for deprotonation of the positively charged Wheland intermediate in MalA/MalA' halogenation (Scheme 2 as shown in FIG. 13). The hydrogen bond between Glu494 and the indole nitrogen is expected to increase the nucleophilicity of the aromatic ring. This facilitates the electrophilic aromatic substitution (EAS) reaction, producing the positively charged intermediate. A water molecule or serine side chain can then deprotonate the Wheland intermediate, leading to re-aromatization of the indole ring system (Scheme 2, FIG. 13).

As revealed in the following examples, two critical residues in the active site significantly contributed to substrate binding, Glu494 and Phe489. Glu494 hydrogen bonds with the indole nitrogen and Phe489 facilitates a favorable hydrophobic interaction with the aromatic ring of the indole. The activity of MalA F489H was significantly decreased relative to the wild-type MalA, especially for the second chlorination reaction. It is expected that the phenylalanine residue in the back of the active site aids in substrate binding, and maintains interactions with the monochlorinated products to facilitate a second halogenation reaction.

The Michaelis-Menten model kinetics displayed equal rates of monochlorination at both the C9 and C8 sites of compound 2, and equal rates for chlorination of compounds 3 and 4, leading to the conclusion that MalA is equally selective for both sites of the indole ring. Interestingly, the catalytic efficiency ($k_{cat}/K_m$) values for the second chlorination chlorination were twice those observed for the first chlorination, thus the initial chlorination is expected to prime the substrate for the second halogenation. This effect can be correlated with the structural data where the chlorine atom on the indole substrates interacts favorably with Phe489, potentially facilitating a better mode of binding. Additionally, the dichlorinated malbrancheamide (compound 1) did not bind in crystals, suggesting a faster dissociation rate for the dichlorinated than either of the monochlorinated products, which bound readily in MalA' crystals.

In efforts elucidate the mechanism of selectivity in MalA, a histidine residue near the catalytic lysine was used to probe the active site region. MalA H253A displayed selectivity for chlorination at the C9 position of compound 2, while MalA H253F was selective for the C8 position of compound 2. MD simulations and DFT calculations demonstrated how key interactions between polar amino acid side chains (Ser129) or water molecules in the active site with the different C—H positions of the indole can control the selectivity of the chlorination reaction. This is accomplished by enhancing the nucleophilicity of the carbon atom during the EAS, but also by pre-organizing a base to carry out the final deprotonation step. An alanine substitution at His253 prevented the interaction of Ser129 and H-C8, leading to an overall apolar active site environment, favoring chlorination at C9. On the other hand, the C8 selectivity observed in MalA H253F can be explained by a more effective Ser129 interaction with H-C8. When investigating these mutants in the site-selectivity of the bromination reaction, the wild-type product profile was observed. Compared to HOCl, HOBr is a milder halogenating reagent, thus favoring the inherently more reactive C9 site of compound 2. These findings demonstrate that even small modulations to the active site region can lead to significant changes in the site-selectivity of the halogenation reaction.

The designation of MalA into a new class of flavin-dependent halogenases is exemplified not only by its reactivity but also by its unique structural motifs: a $Zn^{2+}$-binding C-terminus and an expansive active site, able to accommodate complex substrates. The discovery of this $Zn^{2+}$-binding motif provides a fingerprint for use in mining sequence data for MalA homologs in pursuit of biocatalysts for late-stage halogenation (FIG. 13). Investigation of MalA/MalA' has provided new insights into the biocatalytic mechanism for iterative late-stage halogenation of complex substrates.

The following examples are presented by way of illustration and are not intended to limit the scope of the subject matter disclosed herein.

EXAMPLES

Example 1

Materials and Methods

*M. graminicola* Genomic DNA Extraction and Sequencing

The filamentous fungal strain *Malbranchea graminicola* was cultivated on a static 100 mL potato dextrose broth (PBD) medium for 10 days at 26° C. The genomic DNA (gDNA) extraction and sequencing protocols are the same for that used in Li, et al.[1] and Solexa sequencing was used to determine genome sequences.

*M. aurantiaca* cDNA Preparation

*Malbranchea aurantiaca* was cultured for 15 days in PDB shaking at 160 rpm at 28° C. The Invitrogen Purelink RNA Mini Kit was used with the Plant and Fungal Tissue Processing protocol from the associated RNeasy Mini Handbook (2010) to isolate the RNA prior to treatment with DNase. Invitrogen Superscript first strand synthesis was used with the Protoscript M-MuLV First Strand cDNA Synthesis Kit and protocol to generate the cDNA. The malA coding region was amplified from the cDNA template by PCR using the primers below and the following PCR cycle: (1) 94° C. for 2 minutes, (2) 98° C. for 10 seconds, (3) 66.3° C. for 30 seconds, (4) 68° C. for 2 minutes, repeating steps 2-4 40 times.

Primers

```
                                       (SEQ ID NO: 19)
5'-GAGAGCTAGCATGGCGCCGACACCAAAGTATACGT-3'

(SEQ ID NO: 20)
5'-CATTAAGCTTCTATGCAGCTGGCCTGGTAGGGGTT-3'
```

Cloning of malA-pMCSG7 and malA'-pMCSG7

The malA PCR product was inserted into the pMCSG7 vector by ligation independent cloning (LIC).[2] *Escherichia coli* XL1Blue cells were transformed with malA-pMCSG7 for screening and plasmid maintenance. malA'-pMCSG7 was prepared though site-directed mutagenesis as described below. The HpaC flavin reductase (phaC plasmid) has been described.[3]

*M. aurantiaca* Growth and Extraction of Malbrancheamides

The isolation and purification procedure was adapted from Martinez-Luis, et al.[4] Individual flasks of 75 mL potato dextrose broth were inoculated with 100 µL spore stock of *M. aurantiaca* and grown for three weeks, or until a white fungal mat was produced. Prior to the noticeably orange sporulation, the cultures were pulverized and extracted with dichloromethane. The crude extract was acid-base purified first with 1 M HCl, then neutralized with 2 M ammonium hydroxide to pH 9, and back extracted with dichloromethane. The extract was then purified by chiral HPLC on a Phenomenex Lux 5 µm Cellulose-3 250×10 mm column. The following HPLC time program was used for separation and purification of the malbrancheamide compounds: 50% acetonitrile for 18 minutes, gradient to 55% acetonitrile over 2 minutes, 55% acetonitrile for 2 minutes, gradient to 40% acetonitrile over 2 minutes, 40% acetonitrile for 5 minutes, at a flow rate of 4 mL/minute. The mobile phase consisted of water and acetonitrile. From a 1.5 L growth of *M. aurantiaca*, the following yields of the naturally occurring malbrancheamides were obtained: 1.6 mg/L premalbrancheamide (compound 2) ($^1$H-NMR, 400 MHz, CD$_3$OD, ∂ 1.24 (s, 3H), 1.34 (s, 3H), 1.42 (m, 1H), 1.85 (m, 3H), 1.94 (d, J=11.3 Hz, 1H), 1.99 (d, J=12.8 Hz, 1H), 2.14 (m, 2H), 2.21 (d, J=10.2 Hz, 1H), 2.78 (d, J=15.2 Hz, 1H), 2.89 (d, J=15.3 Hz, 1H), 3.01 (m, 1H), 3.42 (d, J=10.4 Hz, 1H), 7.02 (t, J=7.5 Hz, 1H), 7.07 (t, J=7.6 Hz, 1H), 7.25 (d, J=8.1 Hz, 1H), 7.35 (d, J=7.7 Hz, 1H), 2.6 mg/L isomalbrancheamide B (compound 4), 4.4 mg/L malbrancheamide B (compound 3), and 5.8 mg/L malbrancheamide (compound 1). The structures of the compounds disclosed herein were unequivocally established by NMR and MS studies in comparison to the previous isolation of these molecules. These materials enabled subsequent biochemical and structural studies of MalA and MalA' as well as mutants or variants thereof, as disclosed herein.

MalA Expression and Purification

Expression of malA, malA', and malA/A' mutants. E. coli strain BL21 (DE3) was transformed with malA-pMCSG7 and the pGro7 chaperone plasmid set (GroEL/GroES) from Takara. Ampicillin (0.1 mg/mL), chloramphenicol (35 µg/mL), and L-arabinose (0.5 mg/mL) were added to 1 L of Terrific Broth (TB) media, which was then inoculated with the transformed E. coli cells. The 1 L cultures were grown at 37° C. until an OD$_{600}$ of 0.8-1.0 was reached, cooled at 20° C. for one hour, induced with 0.1 mM isopropyl β-D-1-thiogalactopyranoside (IPTG), and expressed for 18 hours at 20° C.

Expression of malA' for Selenomethionyl MalA'.

450 mL selenomethionine medium (AthenaES) was supplemented with 25 mL TB media, and 150 µg/mL seleno-DL-methionine. Ampicillin (0.1 mg/mL), chloramphenicol (35 µg/mL), and L-arabinose (0.5 mg/mL) were added to the medium, which was then inoculated with the transformed E. coli cells. The cell cultures were grown at 37° C. until an OD$_{600}$ of 0.6 was reached, cooled at 20° C. for one hour, induced with 0.1 mM IPTG, and expressed for 18 hours at 20° C.

Protein Purification for Chlorination Assays and Large-Scale Reactions.

The cell pellet from a 500 mL culture was re-suspended in 30 mL lysis buffer$_{NaCl}$ (10% (v/v) glycerol, 500 mM NaCl, 20 mM imidazole pH 7, 20 mM HEPES pH 7). The cell suspension was supplemented with 50 µM flavin adenine dinucleotide (FAD) and cells were lysed with 5 mg lysozyme, 2 mg DNase, and 3 mM MgSO$_4$. Cell lysis was completed through sonication and cell waste was cleared through centrifugation under standard cell debris pelleting conditions (e.g., 39,200 rcf for 25 minutes). The supernatant was filtered and MalA was purified through metal affinity chromatography on a 5 mL His-trap column (GE Healthcare) with a 10-column volume gradient of elution buffer$_{NaCl}$ (10% glycerol, 500 mM NaCl, 30-560 mM imidazole pH 7, 20 mM HEPES pH 7). The protein was incubated on ice with 2 mM ATP and 50 µM FAD and further purified by size-exclusion chromatography on a Superdex S200 16/60 HiLoad column with storage buffer$_{NaCl}$ (10% glycerol, 300 mM NaCl, 20 mM HEPES pH 7) to remove the chaperone proteins. 20 mg purified MalA were obtained per 1 L of cell culture.

Protein Purification for Bromination Assays and Large-Scale Reactions.

A cell pellet from a 500 mL expression culture was re-suspended in 30 mL lysis buffer$_{NaBr}$ (50 mM NaH$_2$PO$_4$, 10 mM imidazole pH 7, 300 mM NaBr, 10% glycerol) and supplemented with 50 µM FAD. Cell lysis was accomplished through addition of 5 mg lysozyme, 2 mg DNase, and 3 mM MgSO$_4$ and sonication. Cell waste was cleared through centrifugation under standard cell debris pelleting conditions (e.g., 39,200 rcf for 25 minutes), and the protein was purified through batch binding with 10 mL Ni-NTA Superflow resin (Qiagen). The resin-bound protein was washed with wash buffer$_{NaBr}$ (50 mM NaH$_2$PO$_4$, 20 mM imidazole pH 7, 300 mM NaBr, 10% glycerol) and the protein was eluted with elution buffer$_{NaBr}$ (50 mM NaH$_2$PO$_4$, 250 mM imidazole pH 7, 100 mM NaBr, 10% glycerol, 0.2 mM TCEP). Bromide-bound MalA was exchanged into storage buffer$_{NaBr}$ (50 mM NaH$_2$PO$_4$, 1 mM EDTA, 0.2 mM DTT, 10% glycerol, pH 7.3) on a PD-10 column (GE Healthcare).

Protein Purification for Crystallography.

The initial steps of the purification were identical to those for the purification of MalA for chlorination assays. The His-tag was cleaved by TEV protease (1 mg protease/50 mg MalA) in an overnight dialysis with storage buffer$_{NaCl}$, supplemented with 50 µM FAD and 2 mM DTT. Tag-free MalA was separated from TEV protease and any remaining His$_6$-MalA by metal affinity chromatography, and purified by size exclusion chromatography with storage buffer$_{NaCl}$. 10 mg of pure MalA were obtained per 1 L of cell culture.

MalA Biochemical Activity Assays

Biochemical activity assays were performed in a 100 µl volume with the following components: 18 µM MalA, 54 µM HpaC flavin reductase,[3] 100 µM FAD, 50 mM NaCl, 250 µM substrate, 5 mM NADH, and brought to total volume with reaction buffer (same as storage buffer$_{NaBr}$). The chlorination reactions proceeded for 20 minutes and the bromination reactions proceeded overnight. The reactions were extracted with ethyl acetate (200 µL, in triplicate) and dried down under nitrogen gas. The dried extract was resuspended in LC/MS grade methanol to a concentration of around 10 µM for LC/MS analysis. High resolution mass spectrometry was performed using electrospray ionization on an Agilent quadrupole time-of-flight spectrometer (Q-TOF 6500 series). Biochemical activity was monitored via the following HPLC method using acetonitrile and water: 65% acetonitrile for 5 minutes, gradient over 10 minutes to 95% acetonitrile, 95% acetonitrile for 5 minutes, gradient over 2 minutes to 65% acetonitrile, 65% acetonitrile for 11 minutes to re-equilibrate with a flow rate of 0.3 mL/minute, monitoring at 240 nm on a Phenomenex Lux cellulose-3, cellulose Tris (4-methylbenzoate) 250×4.6 mm column.

Co-Crystal Structures of MalA'

Crystallization Conditions.

MalA from M. aurantiaca was recalcitrant to crystallization, but MalA' from M. graminicola (generated by site-directed mutagenesis of malA: L276P/R428P) proved optimal for crystallization. The purified MalA' was dialyzed overnight into a 20 mM HEPES pH 7 buffer with 200 mM NaCl or 300 mM NaCl to remove glycerol, and then supplemented with an equimolar quantity of FAD. Pre-incubation of MalA' with an equimolar concentration of isomalbrancheamide B (compound 4) resulted in crystals with compound 4 bound in a lattice contact and not in the active site. For active site complexes with compounds 2, 3, and 4, MalA' was pre-incubated with a four-fold molar excess of substrate. Crystals were grown by vapor diffusion from 1:2 mixtures of 5 mg/mL MalA' pre-incubated with compound 2, 3 or 4 and a well solution containing 2 M (NH$_4$)$_2$SO$_4$, 0.2 M Li$_2$SO$_4$, 5 mM CdCl$_2$, and 0.1 M Bis-Tris pH 5.5. Crystals were cryoprotected in well solution augmented with 10% glycerol and flash-cooled in liquid nitrogen.

Data Collection.

Data were collected at GM/CA beamline 23ID-B at the Advanced Photon Source (APS) at Argonne National Laboratory. For the SeMet-MalA' crystal, 180° of diffraction data were collected in inverse-beam geometry using 30° wedges. All data were processed using XDS.[5] The SeMet MalA' halogenase structure was solved by single-wavelength anomalous diffraction (SAD) using AutoSol in the Phenix suite to locate the Se sites, determine initial phases and perform density modification (figure of merit=0.236).[6] AutoBuild in the Phenix suite was used to build an 82% complete starting model. The SeMet MalA model was used as a template in molecular replacement to solve the native MalA structure using Phaser in the Phenix suite. A progression of model building and refinement were carried out to complete the models using Coot and Phenix Refine with seven translation/libation/screw groups.[7]

Site-Directed Mutagenesis

MalA' (MalA L276P/R428P).

The site-directed mutagenesis (SDM) to prepare the L276P/R428P double substitution was performed sequentially starting with R428P. The reaction included 100 ng malA-pMCSG7 template, 100 ng each primer (forward$_{L276P}$ and reverse$_{L276P}$) 5 µL 10× Pfu buffer, 0.5 µL dNTPs (250 µM each), and 1 µL PfuTurbo from Agilent in a total of 50 µL. The PCR cycle was (1) 95° C. for 30 seconds, (2) 95° C. for 30 seconds, (3) 55° C. for 1 minute, (4) 68° C. for 8 minutes; steps 2-4 were repeated for 16 cycles. DpnI digestion contained 0.5 µL 2 U/µL DpnI and 25 µL PCR reaction solution for 2 hours at 37° C. and was performed prior to plasmid isolation by alkaline lysis (Purelink Quick Plasmid Miniprep Kit from Invitrogen) and sequencing to verify the presence of the mutant. The L276P substitution was prepared using single primer SDM with 100 ng malA R428P template, 0.2 µM primer, 250 µM dNTPs, 5 µL 10×Pfu buffer, 1 µL Pfu fusion polymerase in a total volume of 50 µL. The PCR time program was as follows: (1) 95° C. for 3 minutes, (2) 95° C. for 35 seconds, (3) 52° C. for 50 seconds, (4) 65° C. for 13 minutes, (5) 65° C. for 15 minutes; steps 2-4 were repeated for 30 cycles. DpnI digestion and sequence analysis were performed in the same manner as described above.

Primers

```
                                          (SEQ ID NO: 21)
R428P_forward  5'-GCACAGCTTTCGCACCCAATTGTGGAGATTGGG-3'

(SEQ ID NO: 22)
R428P_reverse  5'-CCCAATCTCCACAATTGGGTGCGAAAGCTGTGC-3'

L276P
                                          (SEQ ID NO: 23)
5'-CGTCTACCCTCTTGGGAAGGGAGCCCCATAGCGAACTTGATGGATA
TGG-3'
```

MalA K108A.

The malA K108A mutant was prepared using the Quikchange Lightning Site-Directed Mutagenesis Kit and protocol. The PCR time program used was (1) 95° C. for 2 minutes, (2) 95° C. for 20 seconds, (3) 55° C. for 30 seconds, (4) 65° C. for 6 minutes, (5) 65° C. for 5 minutes; steps 2-4 were repeated for 30 cycles. The QCL DpnI digest and transformation protocol were used with XL10-Gold Ultra-competent cells.

Primer

```
                                          (SEQ ID NO: 24)
5'-GTAAAAGCACAGCCCATCCGCGAGTCCGAATAGTCGAAGG-3'
```

All Other malA/malA' Mutants.

The mutants were prepared using single primer SDM with 100 ng malA or malA' template, 0.2 µM primer, 250 µM dNTPs, 5 µL 10×Pfu buffer, 1 µL Pfu fusion polymerase in a total volume of 50 µL. The PCR time program was as follows: (1) 95° C. for 3 minutes, (2) 95° C. for 35 seconds, (3) X° C. (see below) for 50 seconds, (4) 65° C. for 13 minutes, (5) 65° C. for 15 minutes; steps 2-4 were repeated for 30 cycles. DpnI digestion and sequence analysis were performed in the same manner as described above.

Primers

| Mutant | Primer | X (° C.) |
|---|---|---|
| S409A | 5'-GGTTTCACCAACCCGCTCTATGCCCCGGGG ATTAATGTTGG-3' (SEQ ID NO: 25) | 50.0 |
| S82A | 5'-CCTGGTTACAAGATTGGCGAGGCGACTCTA CCTATCTTTTACACCTGG-3' (SEQ ID NO: 26) | 50.8 |
| E494A | 5'-GGCAGTTTTTCGCTGGCATAGCGCGATATT TGTCAGATGTTAACATTGAAACC-3' (SEQ ID NO: 27) | 49.0 |
| E494Q | 5'-GGCAGTTTTTCGCTGGCATACAGCGATATT TGTCAGATGTTAACATTGAAACC-3' (SEQ ID NO: 28) | 49.0 |
| W263A | 5'-CCACCTGTGTTTTCCGGAAGGTGCTGTCTG GGTTATTCGTCTACCCTCTTGGG-3' (SEQ ID NO: 29) | 55.0 |
| W265A | 5'-CCACCTGTGTTTTCCGGAAGGTTGGGTCGC GGTTATTCGTCTACCCTCTTGGG-3' (SEQ ID NO: 30) | 55.0 |
| H253A | 5'-CCCTTTGATCTCTATGAAGGTGATGCGACA AACCACCTGTGTTTTCC-3' (SEQ ID NO: 31) | 48.0 |
| F489H | 5'-CCCCAGGTGGCATGCCTCTGGCAGCATTTC GCTGGCATAGAGCG-3' (SEQ ID NO: 32) | 55.0 |
| C613S/ C616S | 5'-CCGCCCAGATTGGAAAAAGTCTCACTCATC TGGTCTTCTGGGCACCG-3' (SEQ ID NO: 33) | 49.0 |
| C112S | 5'-GGACTCAAGGATGGGCTGTCTTTTTACTTT CTTGATCGAGAGAACC-3' (SEQ ID NO: 34) | 49.6 |
| C128S | 5'-GGGGCAGTACACAGACTTCTCTAGTGTTGG GGCTCCAGGTTTGG-3' (SEQ ID NO: 35) | 53.7 |
| E494D | 5'-GGCAGTTTTTCGCTGGCATAGATCGATATT TGTCAGATGTTAACATTGAAACC-3' (SEQ ID NO: 36) | 50.0 |
| H253F | 5'-CCCTTTGATCTCTATGAAGGTGATTTTACA AACCACCTGTGTTTTCC-3' (SEQ ID NO: 37) | 48.0 |
| S129A | 5'-GGGGCAGTACACAGACTTCTGCGCGGTTGG GGCTCCAGGTTTGG-3' (SEQ ID NO: 38) | 55.0 |
| D129A | 5'-CCTTCGACTATTCGGACTCAAGGCGGGGCT GTGCTTTTACTTTCTTGATCG-3' (SEQ ID NO: 39) | 50.0 |

MalA Large-Scale Reactions and Isolation of Products
   Chlorination Reaction Conditions and Extraction.
   Reactions were run in 1 mL aliquots with 90 μM MalA, 54 μM HpaC flavin reductase, 250 μM compound 2, 100 μM FAD, 50 mM NaCl, 5 mM NADH, and brought to total volume with reaction buffer (same as storage buffer$_{NaBr}$). Reactions were extracted after 20 minutes with 2 mL ethyl acetate in triplicate, dried under nitrogen gas, and re-suspended in methanol for HPLC purification. In a 5.1 mg reaction, 1.7 mg malbrancheamide B (compound 3), 1.3 mg isomalbrancheamide B (compound 4), and 1.2 mg malbrancheamide (compound 1) were isolated.
   Bromination Reaction Conditions and Extraction.
   Reactions were run in 1 mL aliquots with 40 μM MalA, 54 μM HpaC flavin reductase, 250 μM compound 2, 100 μM FAD, 50 mM NaBr, 5 mM NADH, and brought to total volume with reaction buffer (same as storage buffer$_{NaBr}$). Reactions were extracted after 12 hours with 2 mL ethyl acetate in triplicate, dried under nitrogen gas, and resuspended in methanol for HPLC purification. In a 3.7 mg reaction with substrate (compound) 2, 0.9 mg malbrancheamide C (compound 5) and 0.7 mg isomalbrancheamide C (compound 6) were isolated. In a 2 mg reaction with compound 3, 480 μg compound 7 and 300 μg compound 1 were isolated. In a 2.3 mg reaction with compound 4, 1.8 mg compound 8 were isolated.
   HPLC Purification.
   The malbrancheamide B (compound 3), isomalbrancheamide B (compound 4), and malbrancheamide (compound 1) products were purified using the same chiral HPLC method as for purification of the fungal extract. The malbrancheamide C (compound 5), isomalbrancheamide C (compound 6), malbrancheamide D (compound 7), and isomalbrancheamide D (compound 8) products were isolated using chiral HPLC with the previously mentioned semi-preparative cellulose column with the following HPLC time program: 70% acetonitrile for 14 minutes, gradient to 60% acetonitrile over 2 minutes at a flowrate of 4 mL/minute.

Michaelis-Menten Model Kinetics
   Substrates Malbrancheamide B (Compound 3) and Isomalbrancheamide B (Compound 4) to Product Malbrancheamide (Compound 1).
   Reactions were set up in a total volume of 250 μL with the following components: 1.1 μM MalA, 44 μM HpaC flavin reductase, 100 μM FAD, 50 mM NaCl, 3.6 mM NADH, and a variety of substrate concentrations ranging from 1 μM to 60 μM. Reactions were quenched with methanol by removing 50 μL at each time point (2, 5, 10, 15 minutes). Reactions were analyzed on a Schimadzu HPLC with the following LC time program: 40% acetonitrile for 1 minute, gradient over 6 minutes from 40-85% acetonitrile, 85% acetonitrile for 1 minute, gradient over 1 minute to 40% acetonitrile, re-equilibration to 40% for 3 minutes. The absorbance was measured at 240 nm and the mobile phase consisted of water and acetonitrile. A Phenomenex Lux cellulose-3, cellulose Tris (4-methylbenzoate) 250×4.6 mm column was used for separation. GraphPad Prism (Version 6.01) software was used to plot the initial velocities against the substrate concentration and to determine the kinetic constants $k_{cat}$ and $K_m$.
   Substrate Premalbrancheamide (Compound 2) to Products Isomalbrancheamide B (Compound 4) and Malbrancheamide B (Compound 3).
   Reactions were set up in a total volume of 250 μL with the following components: 1.8 μM MalA, 44 μM HpaC, 100 μM FAD, 50 mM NaCl, 3.6 mM NADH, and a variety of substrate concentrations ranging from 5 μM to 80 μM. Reactions were quenched with 100 μL methanol by removing 50 μL at each time point (2, 5, 7, 10 minutes). Reactions were analyzed on a Schimadzu HPLC with the following LC time program: 34% acetonitrile for 1 minute, gradient over 11 minutes to 62% acetonitrile, 62% acetonitrile for 30 seconds, gradient over 30 seconds to 34% acetonitrile, re-equilibration to 34% for 3 minutes. The absorbance was measured at 240 nm and the mobile phase consisted of water and acetonitrile. A Phenomenex Lux cellulose-3 Tris (4-methylbenzoate) 250×4.6 mm column was used for separation.

Computational Methods
   DFT Calculations.
   DFT calculations were performed using Gaussian 09 (Revision D.01).[8] All geometries were optimized using M06-2X,[9] within the CPCM polarizable conductor model (diethylether, ε=4),[10,11] and the 6-31G(d) basis set. Single-point energies were calculated using the same DFT functional and solvation model, and the 6-311++G(d,p) basis set. The resulting energies were used to correct the gas-phase energies obtained from the M06-2X/6-31G(d) optimizations.[12] Enthalpies and entropies were calculated for 1 atm and 298.15 K. All stationary points were verified as minima or first-order saddle points by a vibrational frequency analysis. The use of a dielectric constant ε=4 has been proven to be a good and general model to account for electronic polarization and small backbone fluctuations in enzyme active sites and to have an estimation of the dielectric permittivity in the enzyme active site.[13,14] Computed structures are illustrated with CYLView.[15]
   Molecular Dynamics Simulations.
   Molecular dynamics (MD) simulations were performed using the GPU code (pmemd)[16] of the AMBER 16 package.[17] Parameters for intermediate Cl-K and substrates were generated within the antechamber module using the general AMBER force field (gaff),[18] with partial charges set to fit the electrostatic potential generated at the HF/6-31G(d) level by the RESP model.[19] The charges were calculated according to the Merz-Singh-Kollman scheme[20,21] using the Gaussian 09 package.[8] Each protein was immersed in a pre-equilibrated truncated cuboid box with a 10 Å buffer of TIP3P[22] water molecules using the leap module, resulting in the addition of around 15,000 solvent molecules. The systems were neutralized by addition of explicit counter ions ($Na^+$ and $Cl^-$). All subsequent calculations were done using the widely tested Stony Brook modification of the Amber99 force field (ff99sb).[23] A two-stage geometry optimization approach was performed. The first stage minimizes the positions of solvent molecules and ions imposing positional restraints on the solute by a harmonic potential with a force constant of 500 kcal·mol$^{-1}$·Å$^{-2}$ and the second stage minimizes all the atoms in the simulation cell except those involved in the harmonic distance restraint. The systems were gently heated using six 50 ps steps, incrementing the temperature by 50 K for each step (0-300 K) under constant-volume and periodic-boundary conditions. Water molecules were treated with the SHAKE algorithm such that the angle between the hydrogen atoms was kept fixed. Long-range electrostatic effects were modeled using the particle-mesh-Ewald method.[24] An 8 Å cutoff was applied to Lennard-Jones and electrostatic interactions. Harmonic restraints of 30 kcal·mol$^{-1}$ were applied to the solute and the Andersen equilibration scheme was used to control and equalize the temperature. The time step was kept at 1 fs during the heating stages, allowing potential inhomogeneities to self-adjust. Each system was then equilibrated for 2 ns with a 2 fs time step at a constant volume.

Production trajectories were then run for an additional 500 ns under the same simulation conditions.

References for Example 1 Only (1) Li, S.; Anand, K.; Tran, H.; Yu, F.; Finefield, J. M.; Sunderhaus, J. D.; McAfoos, T. J.; Tsukamoto, S.; Williams, R. M.; Sherman, D. H. Med. Chem. Commun. 2012, 3, 987-996.
(2) Martinez-Luis, S.; Rodriguez, R.; Acevedo, L.; Gonzalez, M. C.; Lira-Rocha, A.; Mata, R. Tetrahedron. 2006, 62, 1817-1822.
(3) Chakraborty, S.; Ortiz-Maldonado, M.; Entsch, B.; Ballou, D. P. Biochemistry. 2010, 49(2), 372-385.
(4) Stols, L.; Gu, M.; Diekman, L.; Raffen, R.; Collart, F. R.; Donnelly, M. I. Protein Expression and Purification. 2002, 25, 8-15.
(5) Kabsch, W.; Acta. Crystallogr. D. Biol. Crystallogr. 2010, 66, 125-132.
(6) Adams, P. D.; Afonine, P. V.; Bunkoczi, G.; Chen, V. B.; Davis, I. W.; Echols, N.; Headd, J. J.; Hung, L. W.; Kapral, G. J.; Grosse-Kunstleve, R. W.; McCoy, A. J.; Moriarty, N. W.; Oeffner, R.; Read, R. J.; Richardson, D. C.; Richardson, J. S.; Terwilliger, T. C.; Zwart, P. H. Acta. Crystallogr. D. Biol. Crystallogr. 2010, 66, 213-221.
(7) Emsley, P.; Cowtan, K. Acta. Crystallogr. D. Biol. Crystallogr. 2004, 60, 2126-2132.
(8) Gaussian 09, Revision D.01, Wallingford Conn. 2013. Frisch, M. J.; Trucks, G. W.; Schlegel, H. B.; Scuseria, G. E.; Robb, M. A.; Cheeseman, J. R.; Scalmani, G.; Barone, V.; Mennucci, B.; Petersson, G. A.; Nakatsuji, H.; Caricato, M.; Li, X.; Hratchian, H. P.; lzmaylov, A. F.; Bloino, J.; Zheng, G.; Sonnenberg, J. L.; Hada, M.; Ehara, M.; Toyota, K.; Fukuda, R.; Hasegawa, J.; Ishida, M.; Nakajima, T.; Honda, Y.; Kitao, O.; Nakai, H.; Vreven, T.; Montgomery, J. A., Jr.; Peralta, J. E.; Ogliaro, F.; Bearpark, M.; Heyd, J. J.; Brothers, E.; Kudin, K. N.; Staroverov, V. N.; Kobayashi, R.; Normand, J.; Raghavachari, K.; Rendell, A.; Burant, J. C.; lyengar, S. S.; Tomasi, J.; Cossi, M.; Rega, N.; Millam, M. J.; Klene, M.; Knox, J. E.; Cross, J. B.; Bakken, V.; Adamo, C.; Jaramillo, J.; Gomperts, R.; Stratmann, R. E.; Yazyev, O.; Austin, A. J.; Cammi, R.; Pomelli, C.; Ochterski, J. W.; Martin, R. L.; Morokuma, K.; Zakrzewski, V. G.; Voth, G. A.; Salvador, P.; Dannenberg, J. J.; Dapprich, S.; Daniels, A. D.; Farkas, Ö.; Foresman, J. B.; Ortiz, J. V.; Cioslowski, J.; Fox, D. J. Gaussian, Inc., Wallingford Conn., 2013.
(9) Zhao, Y.; Truhlar, D. G. Theor. Chem. Acc. 2008, 120, 215.
(10) Barone, V.; Cossi, M. J. Phys. Chem. A. 1998, 102, 1995.
(11) Cossi, M.; Rega, N.; Scalmani, G.; Barone, V. J. Comp. Chem. 2003, 24, 669.
(12) Simon, L.; Goodman, J. M. Org. Biomol. Chem. 2011, 9, 689.
(13) Schutz, C. N.; Warshel, A. Proteins: Struct. Funct. Bioinf. 2001, 44, 400.
(14) Li, L.; Li, C.; Zhang, Z.; Alexov, E. J. Chem. Theory Comp. 2013, 9, 2126.
(15) Legault, C. Université de Sherbrooke, Sherbrooke, Quebec, Canada 2009.
(16) Salomon-Ferrer, R.; Gotz, A. W.; Poole, D.; Le Grand, S.; Walker, R. C. J. Chem. Theory Comput. 2013, 9, 3878-3888.
(17) Case, D. S.; Cheatham, III, C. D. A. T. E.; Darden, T. A.; Duke, R. E.; Giese, T. J.; Gohlke, H.; Goetz, A. W.; Greene, D. Homeyer, N.; Izadi, S.; Kovalenko, A.; Lee, T. S.; LeGrand, S.; Li, P.; Lin, C.; Liu, J.; Luchko, T.; Luo, R.; Mermelstein, D.; Merz, K. M.; Monard, G.; Nguyen, H.; Omelyan, I.; Onufriev, A.; Pan, F.; Qi, R.; Roe, D. R.; Roitberg, A.; Sagui, C.; Simmerling, C. L.; Botello-Smith, W. M.; Swails, J.; Walker, R. C.; Wang, J.; Wolf, R. M.; Wu, X.; Xiao, L.; York D. M.; Kollman, P. A. 2017, AMBER 2017, University of California, San Francisco.
(18) Wang, J.; Wolf, R. M.; Caldwell, J. W.; Kollman, P. A.; Case, D. A. J. Comput. Chem. 2004, 25, 1157-1174.
(19) Bayly, C. I.; Cieplak, P.; Cornell, W.; Kollman, P. A. J. Phys. Chem. 1993, 97, 10269-10280.
(20) Besler, B. H.; Merz, K. M.; Kollman, P. A. J. Comput. Chem. 1990, 11, 431-439.
(21) Singh, U. C.; Kollman, P. A. J. Comput. Chem. 1984, 5, 129-145.
(22) Jorgensen, W. L.; Chandrasekhar, J.; Madura, J. D.; Impey, R. W.; Klein, M. L. J. Chem. Phys. 1983, 79, 926-935.
(23) Wang, J., Cieplak, P.; Kollman, P. A. J. Comput. Chem. 2000, 21, 1049-1074.
(24) Darden, T.; York, D.; Pedersen, L. J. Chem. Phys. 1993, 98, 10089-10092.
(25) Sondergaard, C. R.; Olsson, M. H. M.; Rostkowski, M.; Jensen., J. H. J. Chem. Theory Cornput. 2011, 7(7) 2284-2295.
(26) Olsson, M. H. M.; Sondergaard, C. R.; Rostkowski, M.; Jensen, J. H. "PROPKA3: consistent treatment of internal and surface residues in empirical pKa predictions." J. Chem. Theory Comput. 2011, 7(2), 525-537).

Example 2

Biochemical Activity of MalA

Figure 4:
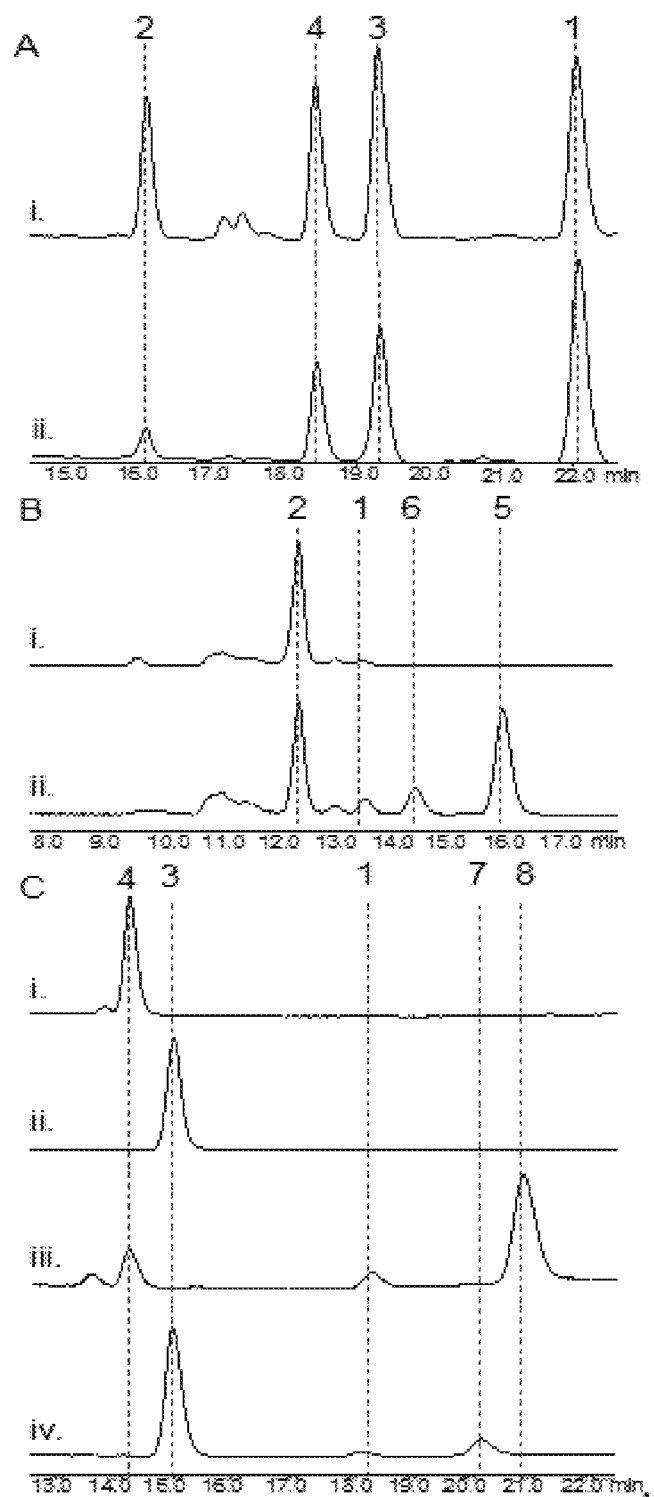
FIG. 4. HPLC traces (240 nm) for the MalA in vitro reactions (A) chlorination of compound 2 (see FIG. 1) (ii) compared to standards from the fungal extract (i), (B) bromination of compound 2 (ii) compared to no enzyme control (NEC) (i), and (C) bromination of compound 4 (iii) compared to NEC (i) and bromination of compound 3 (iv) compared to NEC (ii). See FIG. 1 for compound identities.

Purification of MalA by Ni-affinity chromatography and gel filtration provided pure protein for in vitro assays, and MalA was found to catalyze the iterative chlorination and bromination of the natural precursor premalbrancheamide (compound 2). In reactions with the monochlorinated compounds 3 and 4, MalA was also able to chlorinate and brominate these compounds to generate compounds 1, 7, 8, and 9 of which the latter three are novel indole alkaloids. The chlorination reaction of MalA was confirmed by co-elution with standards isolated from M. aurantiaca (FIG. 4). $^1$H-NMR analysis confirmed the halogenation site on the indole ring and the high-resolution mass spectrometry data for all compounds were consistent with the expected masses and isotope peak patterns for the halogenated products.

Figure 5:
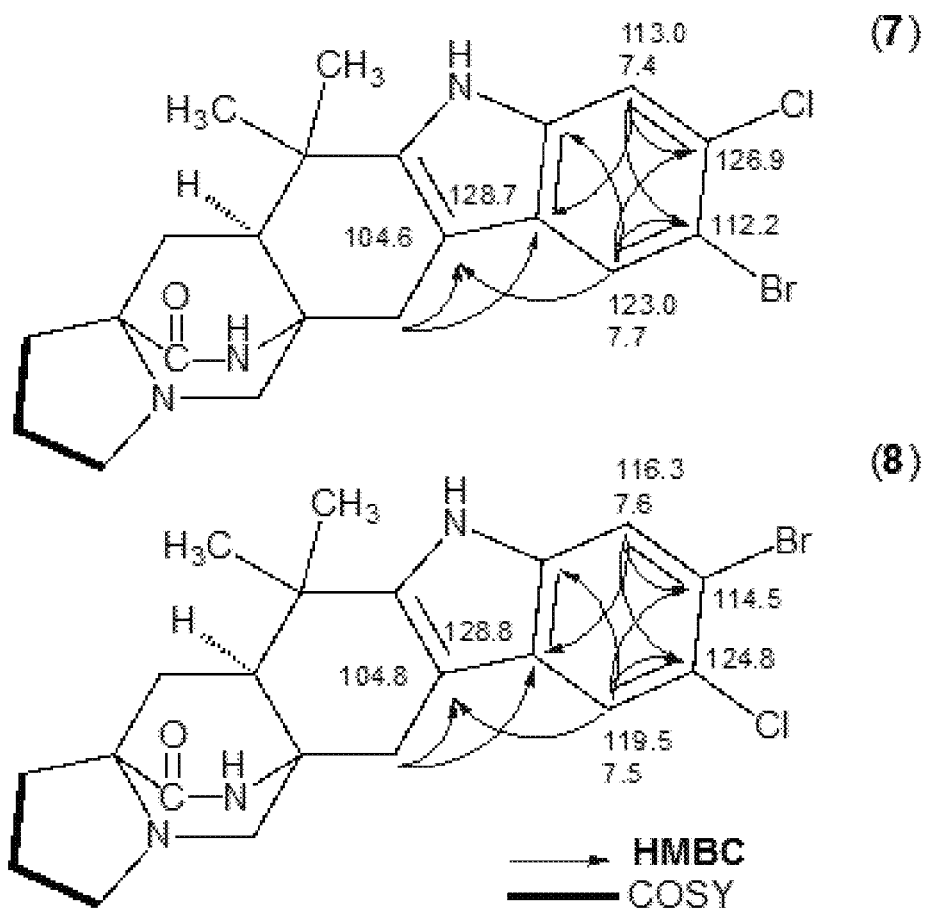
FIG. 5. gHMBCAD and gCOSY NMR correlations for the indole region used to determine the sites of halogenation of new malbrancheamide analogs.

The percent conversions of the halogenation reactions were determined by isolated yields. The chlorination of compound 2 to produce compounds 3, 4, and 1 in a 5 mg in vitro reaction showed 34%, 26%, and 24% conversion, respectively. The bromination of compound 2 in a 4 mg reaction generated 23% compound 5 and 18% compound 6 by isolated yield, but the calculated conversions based on standard curves displayed a C9 selectivity with an 8:1 ratio of 5 to 6. The methodology for separation of these monohalogenated intermediates by HPLC is well resolved compared to previous reports, thus the NMR data for the individual molecules significantly adds to the literature of these brominated indole alkaloids. MalA was also used as a biocatalyst for the generation of two novel malbrancheamide analogs, i.e., compounds 7 and 8 (FIGS. 4 and 5). The bromination of compound 3 in a 2 mg reaction produced 24% compound 7 and 15% compound 1 as a side product. The bromination of compound 4 in a 2.3 mg reaction produced 78% compound 8. The structural assignments of compounds 7, 8, and 9 were confirmed through extensive 1D and 2D NMR analyses. The structures were confirmed using key gHMBCAD correlations (FIG. 5) where a significant downfield shift was observed for the chlorinated carbon as opposed to the brominated carbon. The positions of the halogens on the indole ring were confirmed by the two singlet peaks observed in the $^1$H-NMR aromatic region of each spectrum. Moreover, compounds 5 and 6 can also be chlorinated to produce compounds 8 and 7, respectively.

Example 3

Kinetic Characterization of MalA

Michaelis-Menten kinetic parameters were determined for the natural chlorination reactions of MalA. They revealed that the enzyme has similar $k_{cat}$ and $K_m$ values for both the initial and second chlorination reactions. The $k_{cat}$ from compound 2 to compound 3, compound 2 to compound 4, compound 3 to compound 1, and compound 4 to compound 1 were 0.08, 0.09, 0.12, and 0.12 min$^{-1}$, respectively, which are comparable values to those of FDH PrnA (0.10 min$^{-1}$).[2] The $K_m$ values for compound 2 to compound 3, compound 2 to compound 4, compound 3 to compound 1, and compound 4 to compound 1 were 7.0, 7.5, 4.4, and 4.0 μM. The catalytic efficiencies were calculated for each of the four reactions resulting in the $k_{cat}/K_m$ values of 11.5, 12.0, 27.3, and 29.7 min-1 mM-1, respectively. These catalytic efficiencies are fairly high compared to those of the eukaryotic FDH Rdc2, which are 2.93 min-1 mM-1 for the initial chlorination reaction and 0.11 min-1 mM-1 for the second chlorination reaction.[4]

Example 4

Structural Characterization of the Substrate Complexes of MalA'

Figure 6:
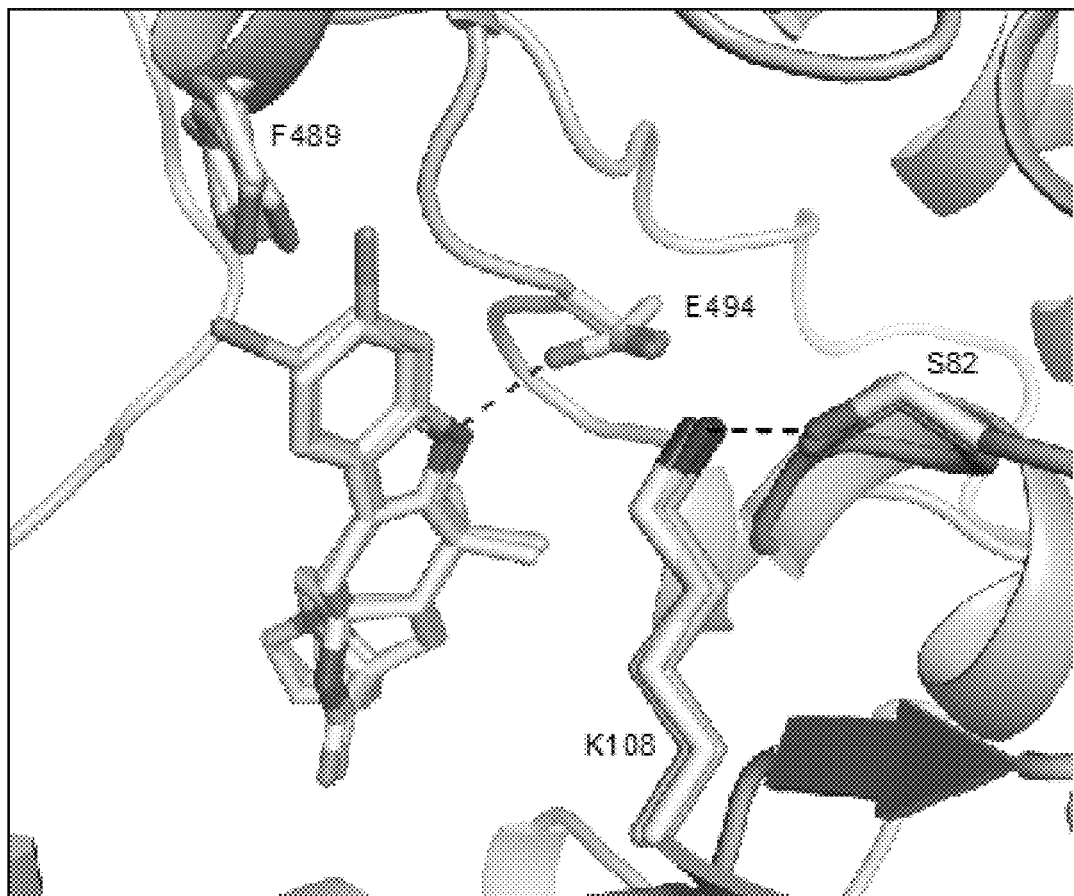
FIG. 6. MalA' active site overlay of complexes with substrates 2 (yellow), 3 (pink), and 4 (cyan). See FIG. 1 for the identities of substrates, or compounds, 2, 3, and 4.
Figure 8:
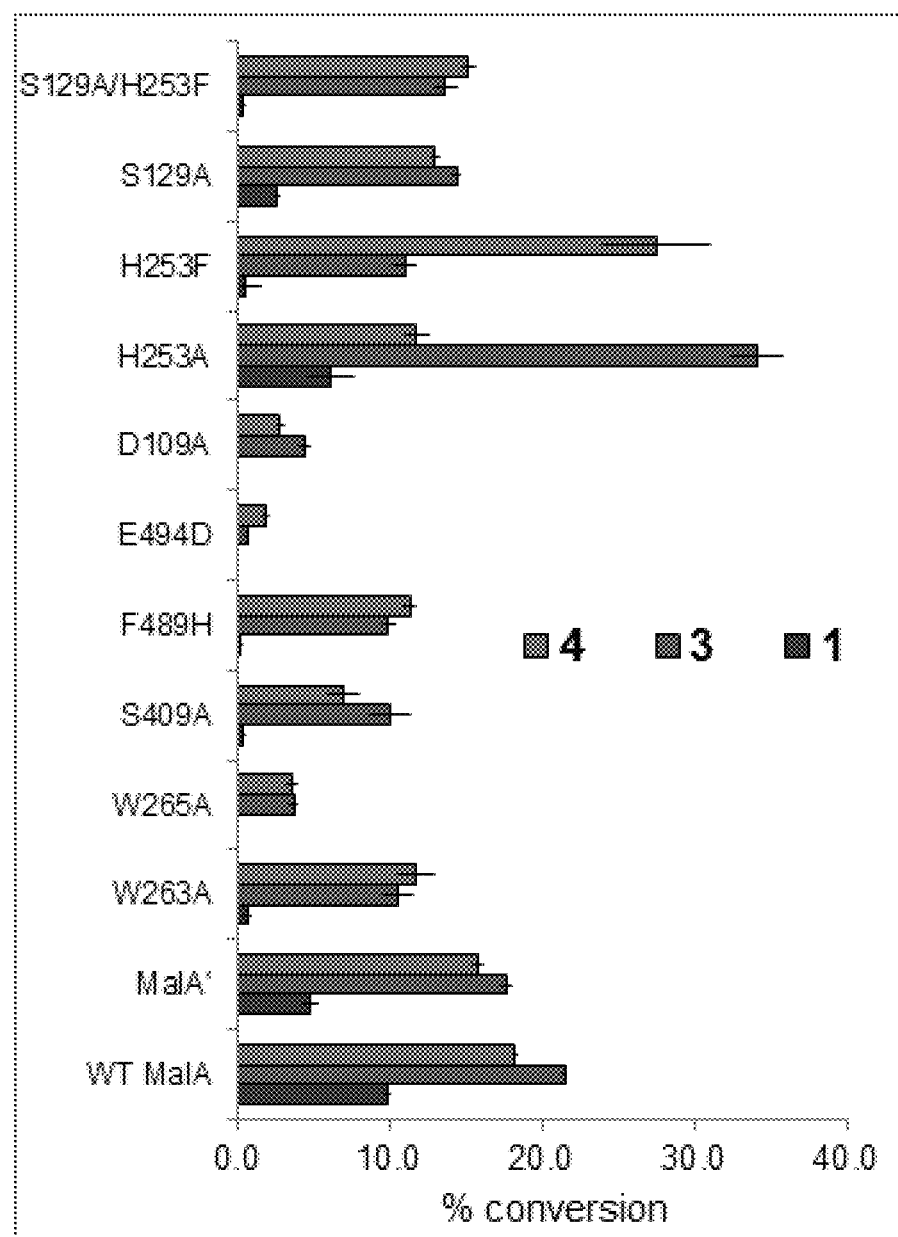
FIG. 8. Percent conversion with mutants versus wild-type MalA in reactions with compound 2 to produce compounds 4 (green), 3 (blue), and 1 (red). MalA K108A and E494A/Q were inactive and MalA S82A was insoluble, and was not functionally analyzed. See FIG. 1 for compound identities.
Figure 9:
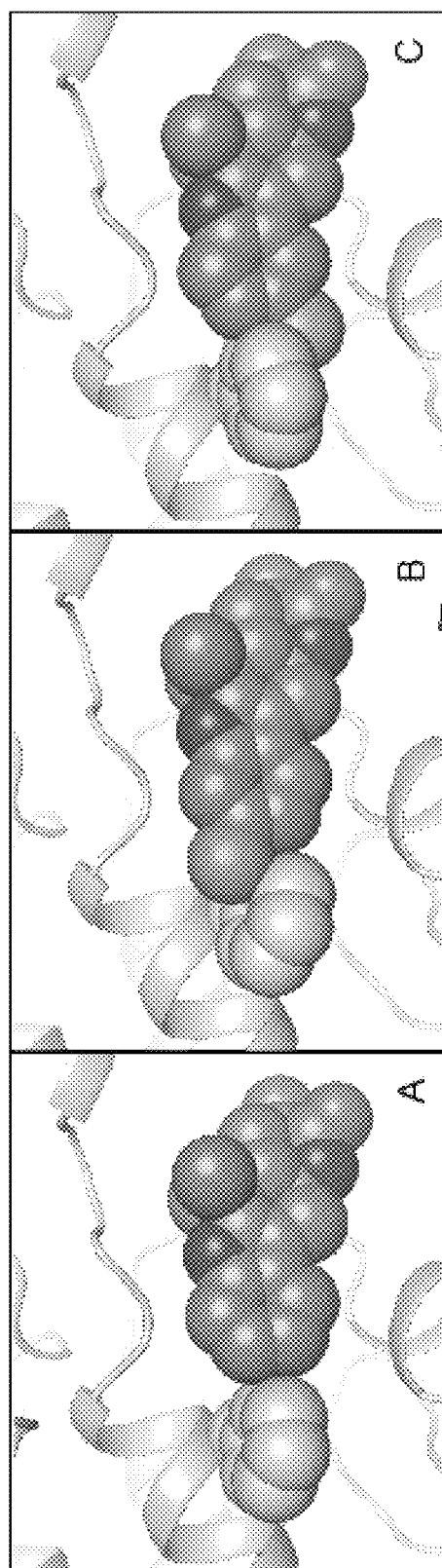
FIG. 9. Interactions between MalA' Phe489 (orange) and substrates (A) premalbrancheamide (compound 2), (B) malbrancheamide B (compound 3), and (C) isomalbrancheamide B (compound 4). See FIG. 1 for compound identities.

To further elucidate the unique functionality of MalA/MalA' reactivity at two sites, the co-crystal structures of a MalA' in complex with premalbrancheamide (compound 2), malbrancheamide B (compound 3), and isomalbrancheamide B (compound 4) were determined. MalA and MalA' are 99% identical, differing at only two amino acid positions (Leu276 and Arg428 in MalA; Pro276 and Pro428 in MalA'), and have comparable catalytic activities, but only MalA' was amenable to crystallization. To verify that MalA' was a viable substitute for MalA, the activities of the two were compared, and it was determined that MalA' was essentially identical to MalA under the reaction conditions tested. The structures of the ternary complexes with FAD, chloride ion, and each of the three substrates (compounds 2, 3, and 4) were determined at 2.36 Å, 2.09 Å, and 2.04 Å, respectively. MalA' has a similar overall structure to bacterial FDHs, with the addition of a few unique motifs including a $Zn^{2+}$-binding C-terminus and a large active site capable of accommodating the structurally complex substrates. The natural substrates, compounds 2, 3, and 4, have a similar binding mode in the MalA' active site (FIG. 6). Specific interactions include a hydrogen bond of the indole nitrogen to Glu494 and a Cl-π interaction of compounds 3 and 4 with Phe489 (FIGS. 6 and 9). The roles of amino acids in the active site were analyzed through site-directed mutagenesis (FIGS. 7 and 8), and Lys108 was determined to be necessary for catalytic activity.

Figure 7:
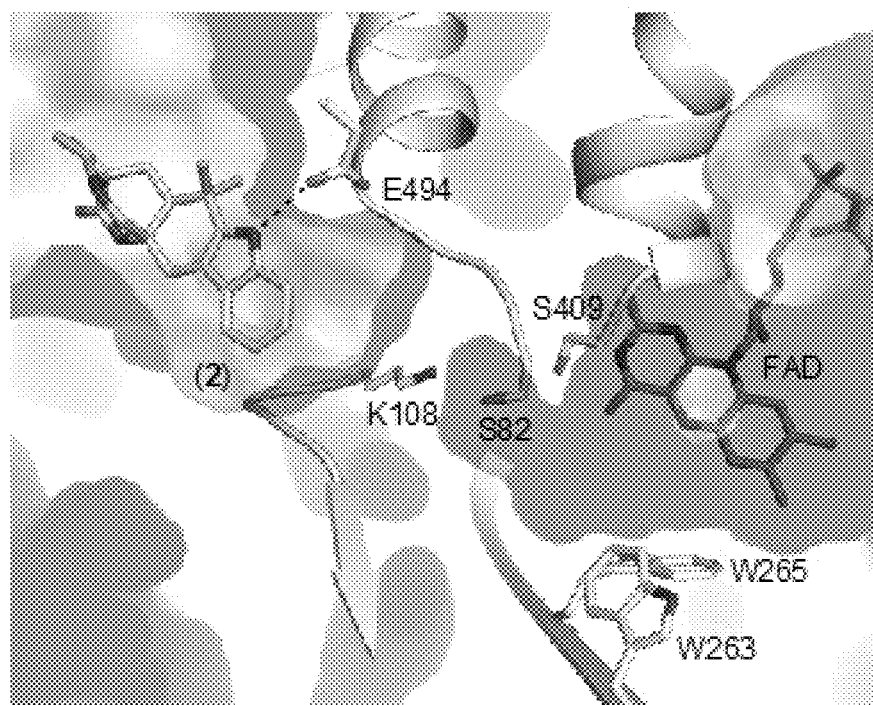
FIG. 7. Active site of MalA', revealing clear separation between the substrate and FAD binding pockets.

Trp263 and Trp265 form a characteristic flavin-binding motif proposed to aid in cofactor binding (FIG. 7). While MalA W265A showed a drastic decrease in activity, MalA W263A showed a more modest decrease in product formation (60% production of compound 4, 50% production of compound 3, and 5% production of compound 1) relative to wild-type MalA. A residue key to binding the substrate (Phe489) was substituted with histidine to ascertain its significance in the activity of MalA and was found to decrease the activity as well. Phe489 is analogous to the phenylalanine whose mutagenesis altered the site-selectivity in the FDH PrnA.[33]

Figure 10:
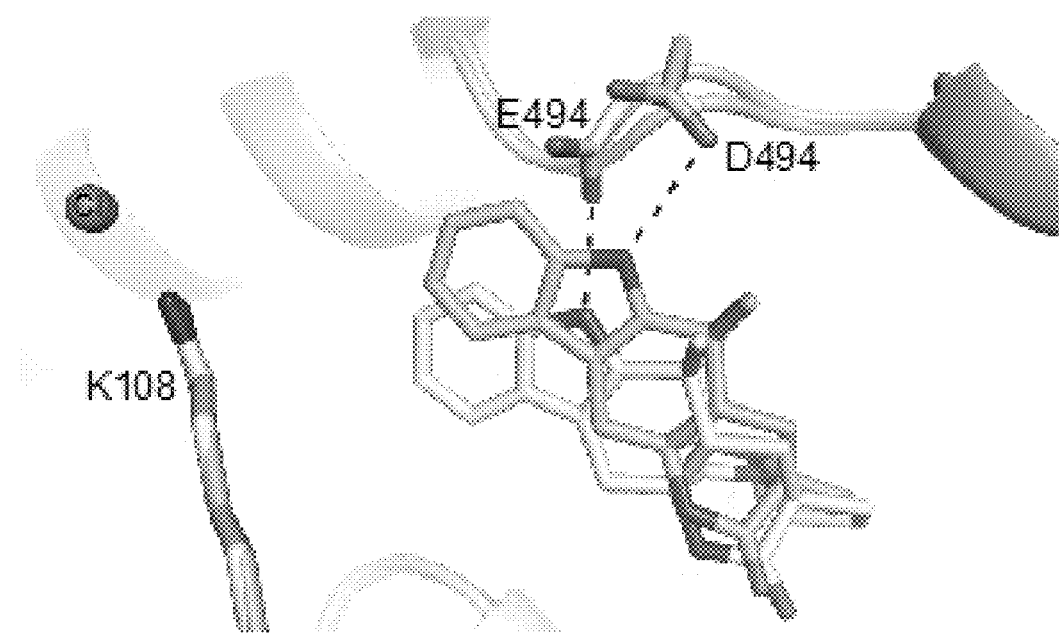
FIG. 10. Comparison of wild-type MalA' (yellow) and MalA' E494D (cyan) co-crystallized with compound 2. See FIG. 1 for compound identities.

In an effort to probe the mechanism of MalA, Glu494 was substituted with a variety of other residues including alanine, glutamine, and aspartate. While E494A and E494Q inactivated MalA, E494D maintained slight activity. Glu494 forms a hydrogen bond with the proton of the indole nitrogen, facilitating binding of the substrate. The substitution of aspartate at this position shifted the substrate away from the catalytic lysine, thus decreasing the activity (FIGS. 8 and 10).

Figure 11:
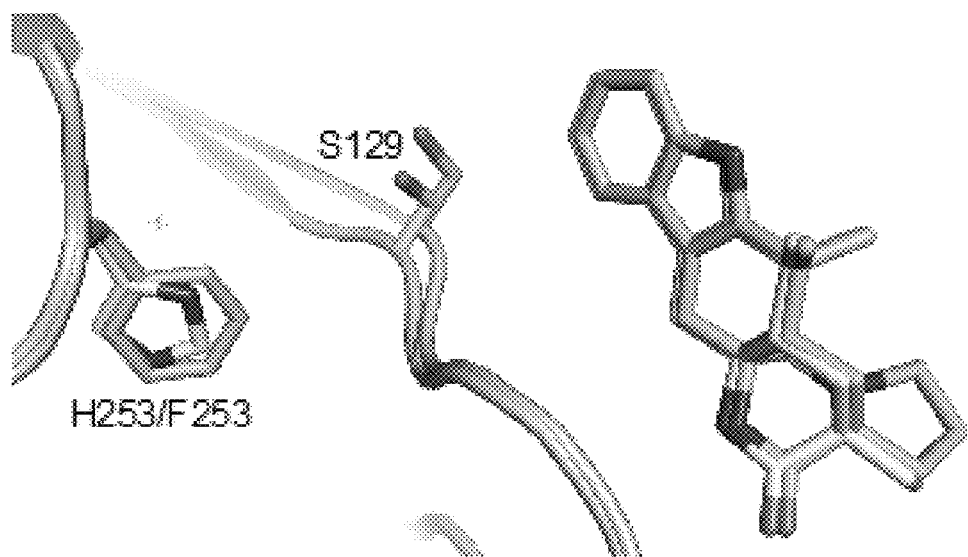
FIG. 11. Comparison of wild-type MalA' (yellow) and MalA' H253F (cyan) co-crystallized with compound 2. See FIG. 1 for compound identities.
Figure 20:
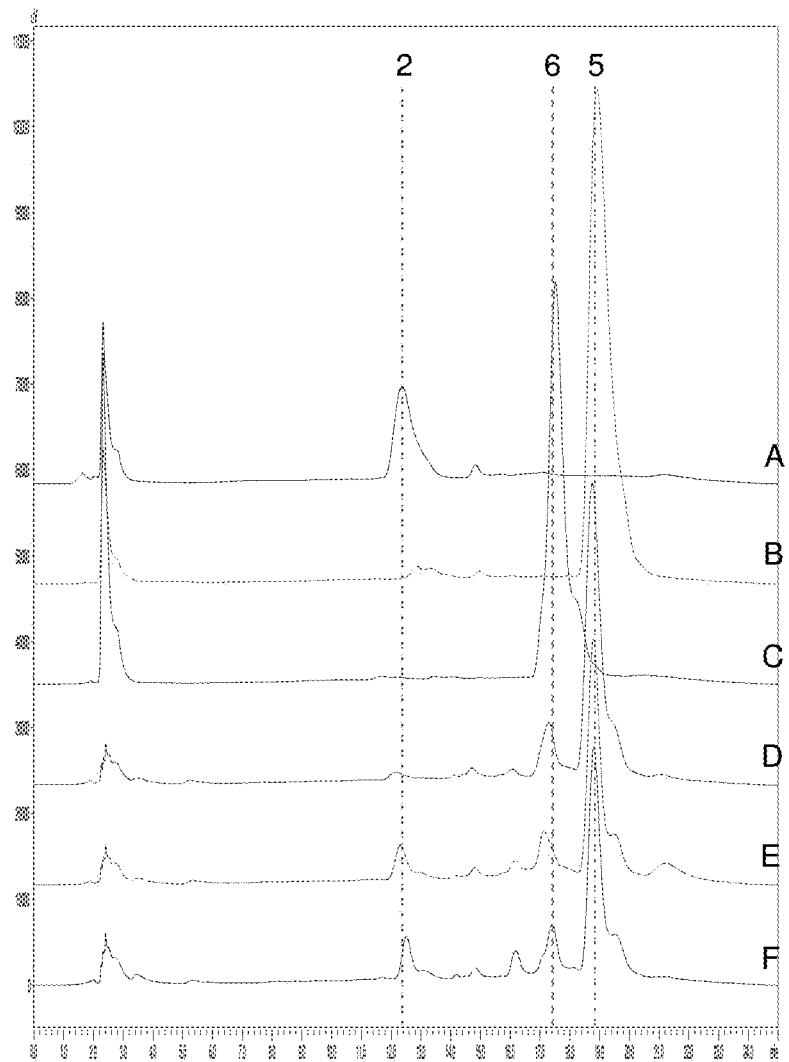
FIG. 20. Bromination of compound 2 with MalA H253A and MalA H253F compared to wild-type MalA. (A) standard compound 2, (B) standard compound 5, (C) standard compound 6, (D) WT MalA bromination reaction with compound 2, (E) MalA H253A bromination reaction with compound 2, and (F) MalA H253A bromination reaction with compound 2.
Figure 21:
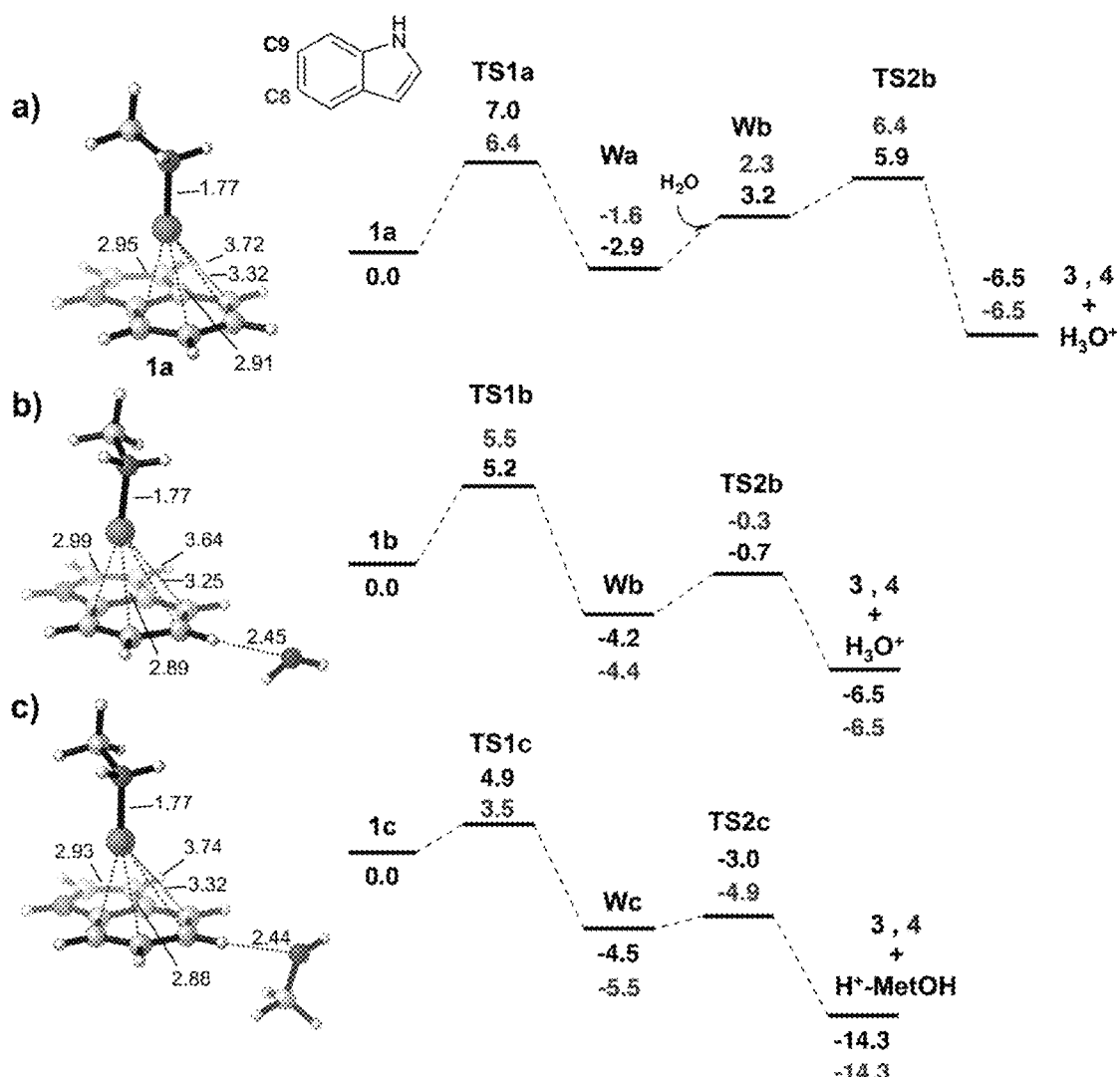
FIG. 21. DFT optimized reaction pathways for the C8 and C9 chlorination using three computational models: a) an indole ring and methyl chloramine; b) an indole ring, methyl chloramine and a water molecule closer to C8- or C9-H respectively; c) an indole ring, methyl chloramine and a methanol molecule as a Ser129 model. Relative Gibbs free energies (ΔG, in kcal/mol) are computed at the M06-2x/6-311+G(d,p)/CPCM(Diethylether)//M06-2x/6-31G(d)/CPCM(Diethylether) level. Bond lengths are in Å.

Initial efforts to probe the mechanism of site-selectivity in MalA included substitution of His253 with alanine, phenylalanine, and other amino acids. MalA H253A was selective for producing the C9-chlorinated compound 3, while MalA H253F displayed selectivity for producing the C8-chlorinated compound 4. Co-crystal structures of MalA' H253A in complex with compounds 2 and 3 revealed no evident changes in the protein that would lead to the observed site-selectivity. On the other hand, the co-crystal structure of MalA' H253F in complex with compound 2 revealed a shift in S129, a residue near the indole ring of the substrate (FIG. 11). When S129 was substituted with alanine, the C8 selectivity of MalA H253F was abolished, leading to the conclusion that Ser129 is involved in the selectivity induced by the Phe substitution at position 253 (FIG. 8). Interestingly, the MalA H253A and MalA H253F mutants did not display the same site-selectivity profile for the bromination reaction. Instead, the same product profile as the wild-type MalA was found (see FIG. 20).

The structures of MalA' also revealed a unique zinc site with coordination by four cysteine residues (Cys597, Cys600, Cys613, Cys616) near the C-terminus. The $Zn^{2+}$ ion was identified using anomalous scattering experiments with diffraction data recorded at X-ray energies bracketing the zinc K-edge (9.6586 keV). Anomalous difference density was present only in the map using data from the energy above the edge. A double mutant MalA C613S/C616S was prepared and the protein was insoluble, thus no biochemical activity assays were performed in the absence of $Zn^{2+}$.

Example 5

Molecular Dynamics Simulations and QM Models

Molecular dynamics (MD) simulations were performed to gain further insight into the structure and activity of the protein, starting from the MalA' crystal structures in their apo and substrate bound forms. In the latter case, the Lys108 chloramine intermediate has been considered integral to the mechanism discussed below.

The analysis of the MD trajectories revealed the structural role played by the $Zn^{2+}$ counterion in the protein structure. Residues within the $Zn^{2+}$ binding region (597-616) exhibited a low root-mean-square fluctuation (RMSF) compared to the very flexible adjacent region (621-646). These simulations indicate that the flexible region acts as a substrate channel lid, having two main open/closed conformations that were explored during the 500 ns MD simulations in both the apo and substrate-bound states.

From the apo state trajectories, the $pK_a$ of the Lys108 and Glu494 side chains was estimated. Glu494 has a relatively high $pK_a$ of about 6.0-7.5, while Lys108 has an estimated $pK_a$ of 7.2-8.3.

The analysis of possible polar interactions between the substrate and the enzyme active site showed that, although the backbone carbonyls of Gly131 and Ala132 could potentially interact with the substrate amide nitrogen, these interactions are not as important as the Glu494-H(N-indole) hydrogen bond. The latter corresponds to the main and stronger interaction between the substrate and protein active site residues, and it is observed with all bound substrates (compounds 2, 3 and 4) during the entirety of the MD trajectory simulations. The basicity of Glu494 can thus enhance the hydrogen bonding between the carboxyl side chain and the indole ring of the substrate, positioning it to effectively interact with the catalytic Lys108 residue.

MD simulations including the proposed active chloramine Cl-Lys108 species showed that when substrate 2 (compound 2) is bound into the active site and the channel lid is closed, the Cl atom is placed very close to the C8/C9 positions of the substrate, due in part to the positioning of the substrate by the Glu494 residue (see FIG. 12a). When the lid is in its open conformation, the substrate binding is slightly displaced, although still H-bonding with Glu494, but then the Cl-Lys108 side chain conformation changes to place the Cl atom closer to the FAD cofactor. This indicates that the protein conformational change between the substrate bound open/closed states also controls the positioning of Cl-Lys108 active species, which can explore two main conformations to bring the Cl atom from the flavin cofactor to the substrate. This observation supports the expectation that Cl-Lys108 is the actual chlorinating species. When Cl-Lys108 is in this catalytically competent pose, the distances (Cl—C) and angles (Cl—C—H) measured for both C8 and C9 positions are very similar, indicating that Cl-Lys108 is preorganized to chlorinate both positions.

MD simulations also revealed a key interaction between Cl-Lys108 and the backbone carbonyl of the neighboring Asp109 residue, effectively positioning Cl-Lys108 towards a catalytically competent arrangement (FIG. 12a). The Cl atom from Lys108 chloramine active species can only be placed close to the C8/C9 positions when this H-bond is present. The essential role of the Asp109 was further explored by mutagenesis experiments, and the D109A mutant had very low activity (FIG. 8). MD simulations on this particular mutant showed that the Ala109 backbone carbonyl is pointing towards a different position than in the original Asp109, thus eliminating a key hydrogen bond interaction. This is caused by the different conformation of the amino acid side chain, which is pointing outside the protein cavity and exposed to the solvent in Asp109, while in Ala109 it is displaced. Indeed, in the 500 ns simulations for the D109A mutant, Cl-Lys108 never explores any conformation in which the Cl atom approaches the C8/C9 positions to perform chlorination.

MD simulations on MalA' Cl-Lys108 with bound substrate 2 (compound 2) highlighted the arrangement of the Ser129 side chain with respect to H-C8 in compound 2. The distance between Ser129 $O_\gamma$ and H-C8 is particularly short (between 2.5-3.5 Å) when the substrate is in an appropriate orientation for the electrophilic aromatic substitution. This interaction was not observed along the MD trajectory of MalA' H253A, but was prominent in the MalA' H253F trajectory. This interaction is quite important since Ser129 is one of the few polar residues in a very hydrophobic region of the active site pocket. Along the MD trajectories, the solvation shell estimated for the C8 and C9 positions of compound 2 showed a more apolar environment for wild-type MalA' and MalA' H253A (i.e., fewer surrounding water molecules) than for MalA' H253F.

Figure 12:
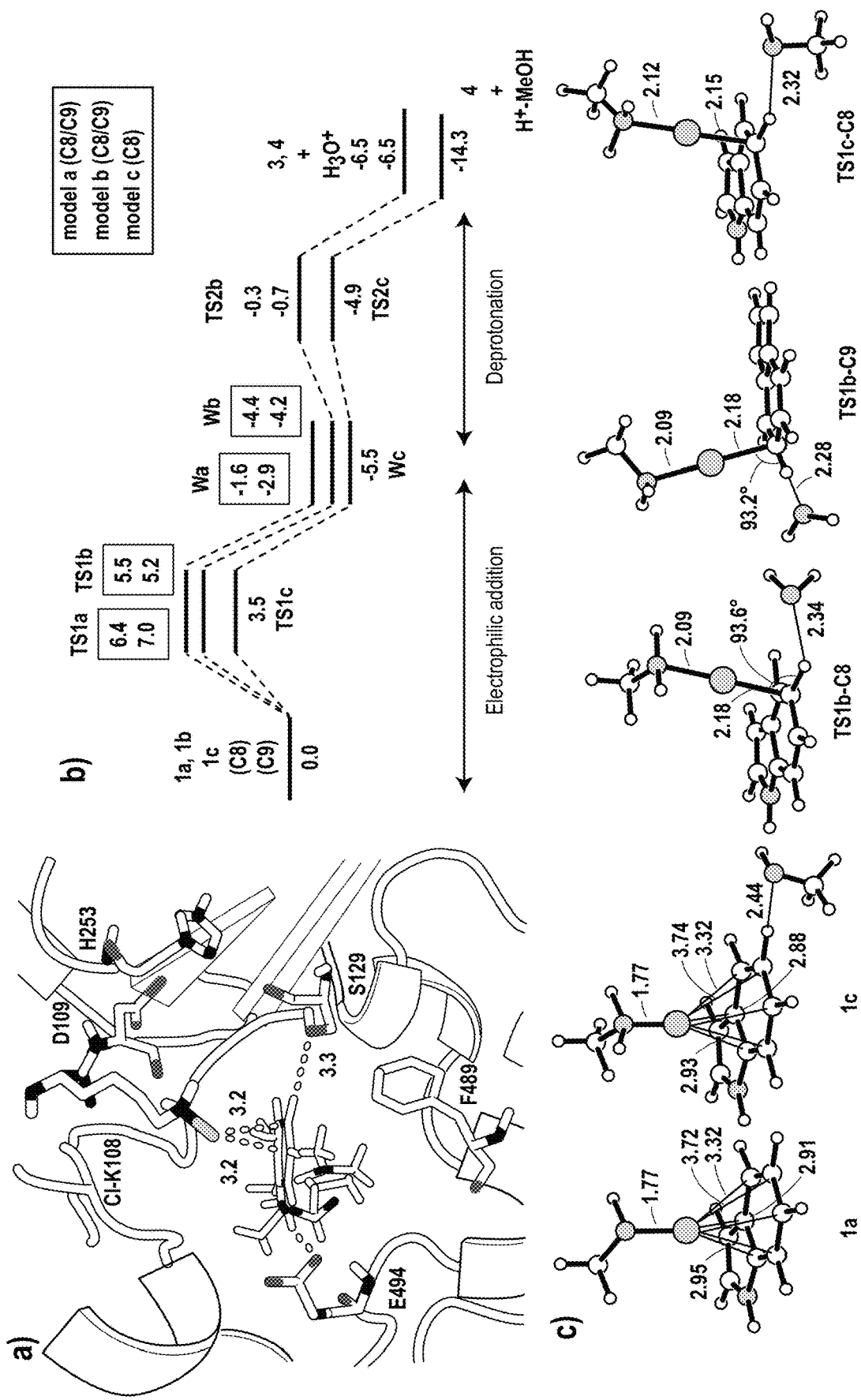
FIG. 12. a) Representative snapshot (at 40 ns) taken from the 500 ns MD simulation of MalA' and substrate 2-bound complex, including the chloramine adduct at Lys108. b) Computed DFT reaction pathways for the three models: 1a—indole and methyl chloramine; 1b—indole, methyl chloramine and a water molecule coordinating at the C8 or C9 positions, respectively; 1c—indole, methyl chloramine, and MeOH coordinating to H-C8. c) DFT optimized geometries of some representative structures. Gibbs energies are given in kcal/mol, and distances in Å.

Based on the experimental evidence and computational modeling of the enzyme active site, a mechanism for the MalA halogenase was developed (FIG. 12, Scheme 2) involving the formation of a Lys108-chloramine intermediate active species, which then interacts with C8 or C9 to carry out an electrophilic aromatic substitution (EAS), with generation of a Wheland intermediate (W) before a final deprotonation step (Scheme 2). This deprotonation can be effected by a water molecule acting as a base, or in the case of C8 by the well-positioned Ser129. To gain insight into the proposed reaction mechanism, density functional theory (DFT) calculations were conducted, using three different computational models (see Example 1 for computational details). The first model considers only an indole ring and a protonated methyl chloramine as the active species (1a); the second adds a water molecule close to H-C8 or H-C9 positions (1b); and the third model includes a methanol molecule near H-C8 position to mimic Ser129 (1c). Calculations show that the intrinsic rate-limiting step of the reaction is the initial chlorination, while the deprotonation step occurs slightly faster. A water molecule or methanol interacting with the C8/C9 protons accelerates the chlorination steps because hydrogen bonding enhances the nucleophilicity of these carbons. The computed reaction barrier for C8-chlorination (TS1a-C8) was decreased from 6.4 to 5.5 kcal/mol by a coordinating $H_2O$ (TS1b-C8), and further decreased to 3.5 kcal/mol when methanol coordinates to the H-C8 (TS1c-C8). On the other hand, the computed barrier for C9 chlorination (TS1a-C9) decreased from 7.0 to 5.2 kcal/mol by a coordinating $H_2O$ molecule at H-C9 (TS1b-C9), and to 4.9 kcal/mol when methanol interacted with H-C8 (TS1c-C9), as shown in FIG. 12. This highlights the role of Ser129 in directing the selectivity towards the formation of the C8 chlorinated product.

The Wa-C9 Wheland intermediate is 1.3 kcal/mol more stable than Wa-C8, but they become almost isoenergetic when coordinating water molecules are considered (Wb-C8 and Wb-C9). An apolar environment favors the formation of the C9 chlorinated product 3 (compound 3). Finally, once the Wheland intermediates are formed, re-aromatization by deprotonation occurs rapidly. The computed deprotonation barriers for the two positions are 4.1 and 3.5 kcal/mol for C8 (TS2b-C8) and C9 (TS2b-C9), respectively, when a water molecule acts as the base, and 0.6 kcal/mol for C8 when methanol acts as a base (TS2c-C8).

The DFT optimized structures for the reactant complexes and transition states are highly similar. The catalytically competent arrangement of Cl-Lys108 near C8 and C9 was found in the MD simulations (represented in FIGS. 12a, 12c). Taking together the QM models, MD simulations, and the pre-organization of the Cl-Lys108 versus the substrate previously described, the reaction mechanism is expected to involve a Cl-Lys108 intermediate, which is the most plausible mechanism for the MalA flavin-dependent halogenase.

Example 6

Figure 15:
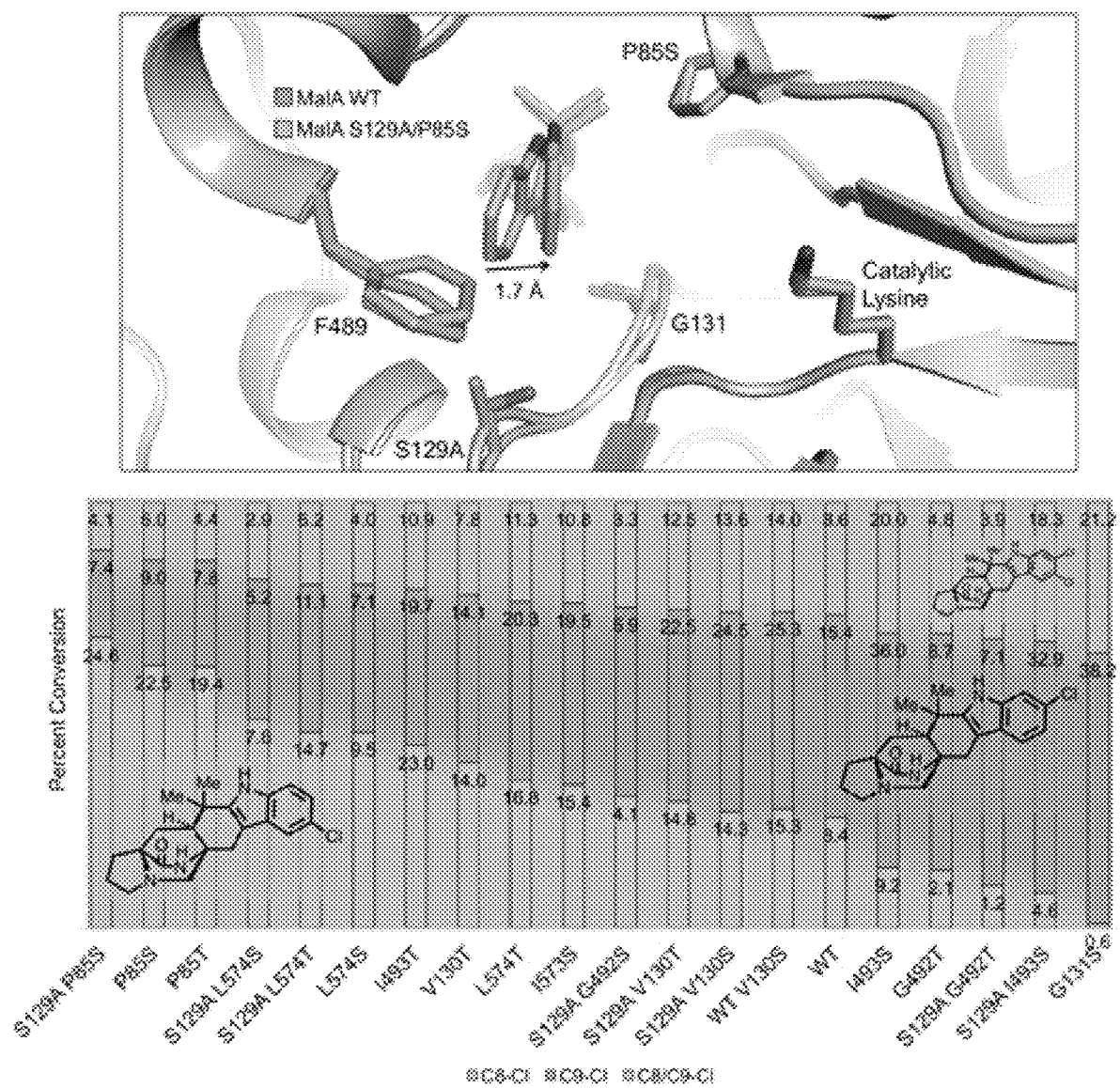
FIG. 15. MalA variants display a range of site-selectivity on the natural substrate premalbrancheamide. The substrate position can be shifted to achieve site-selectivity.
Figure 16:
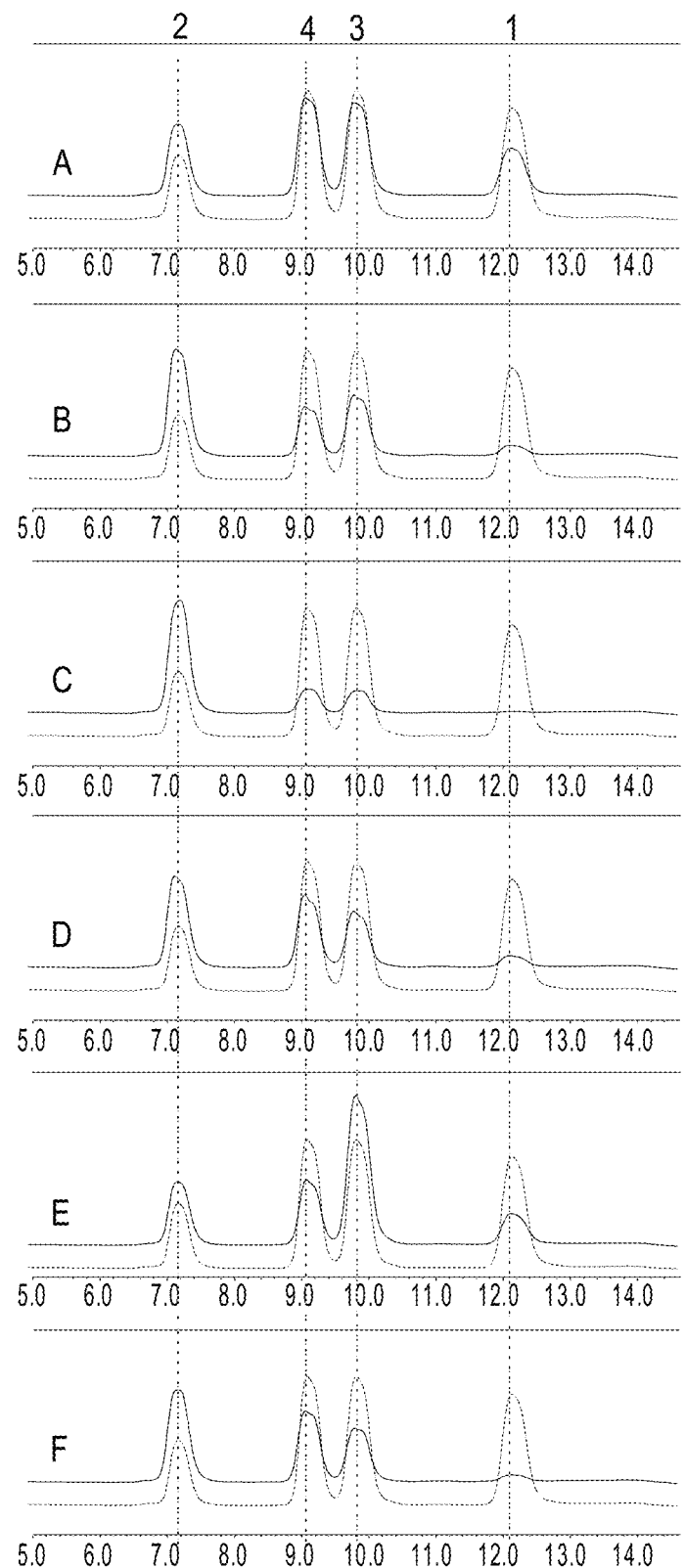
FIG. 16. Wild-type MalA (pink) reactions compared to mutants in black (A) MalA' (MalA L276P/R428P), (B) MalA W263A, (C) MalA W265A, (D) MalA S409A, (E) MalA H253A, (F) MalA F489H. The reactions are composed of MalA or MalA variants combined with a nonspecific flavin reductase, excess flavin cofactor, NaCl as a source for chloride ion, and NADH cofactor. Analysis was performed by monitoring the absorbance at 240 nm by HPLC.
Figure 17:
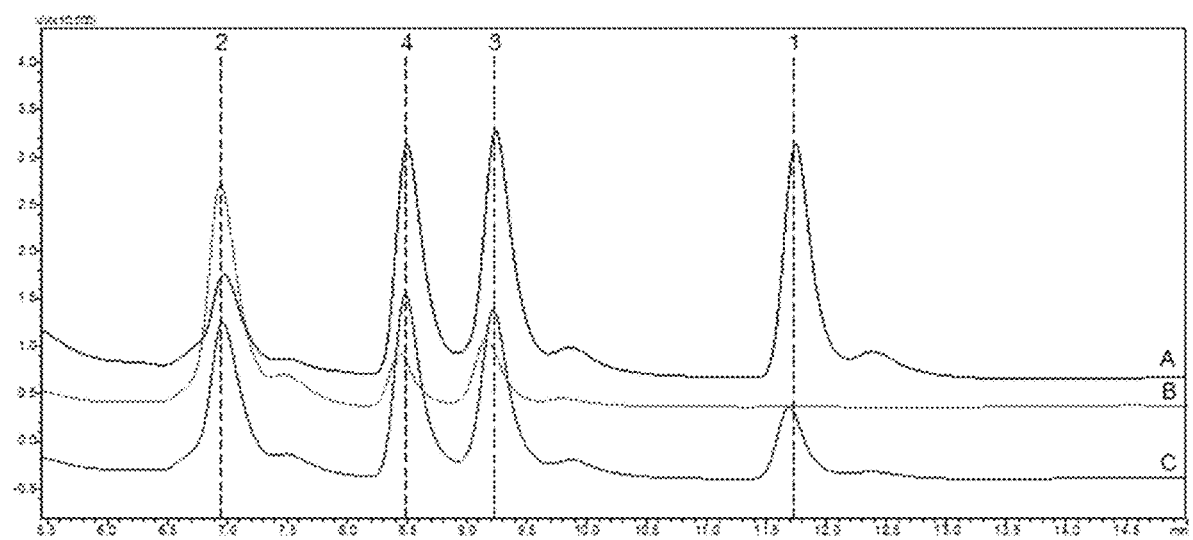
FIG. 17. (A) Wild-type MalA reaction compared to (B) MalA D109A, and (C) MalA S129A. The reactions are composed of MalA or MalA variants combined with a nonspecific flavin reductase, excess flavin cofactor, NaCl as a source for chloride ion, and NADH cofactor. Analysis was performed by monitoring the absorbance at 240 nm by HPLC.
Figure 18:
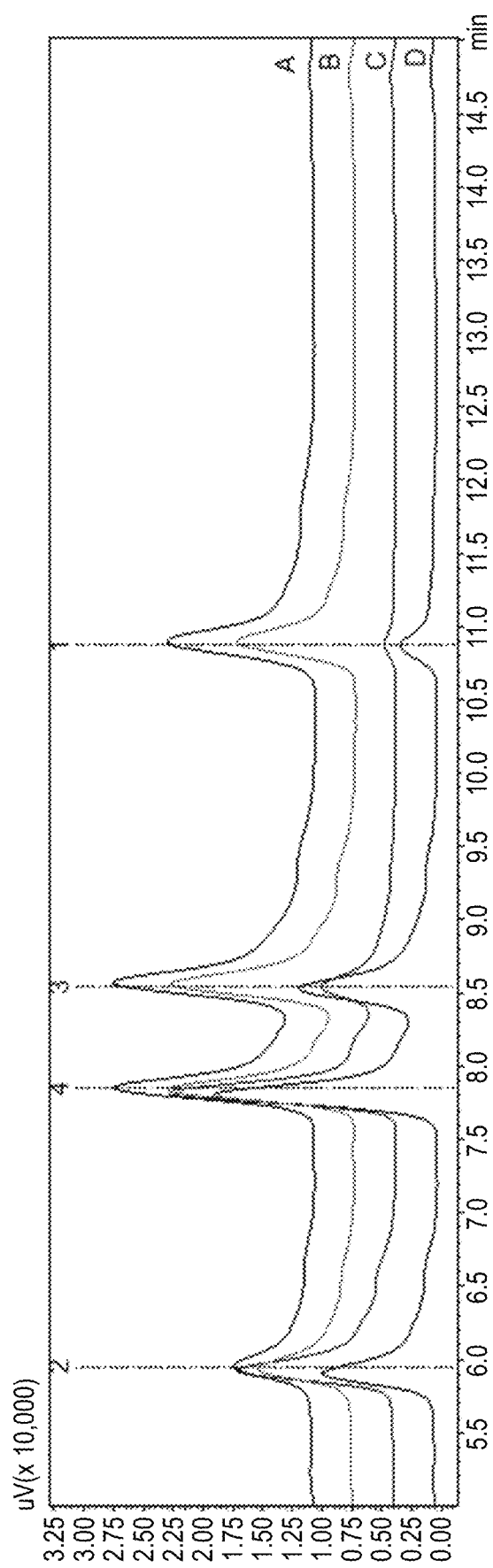
FIG. 18. (A) Wild-type MalA reaction compared to (B) MalA S129A, (C) MalA H253F, and (D) MalA S129A/H253F. The reactions are composed of MalA or MalA variants combined with a nonspecific flavin reductase, excess flavin cofactor, NaCl as a source for chloride ion, and NADH cofactor. Analysis was performed by monitoring the absorbance at 240 nm by HPLC.
Figure 19:
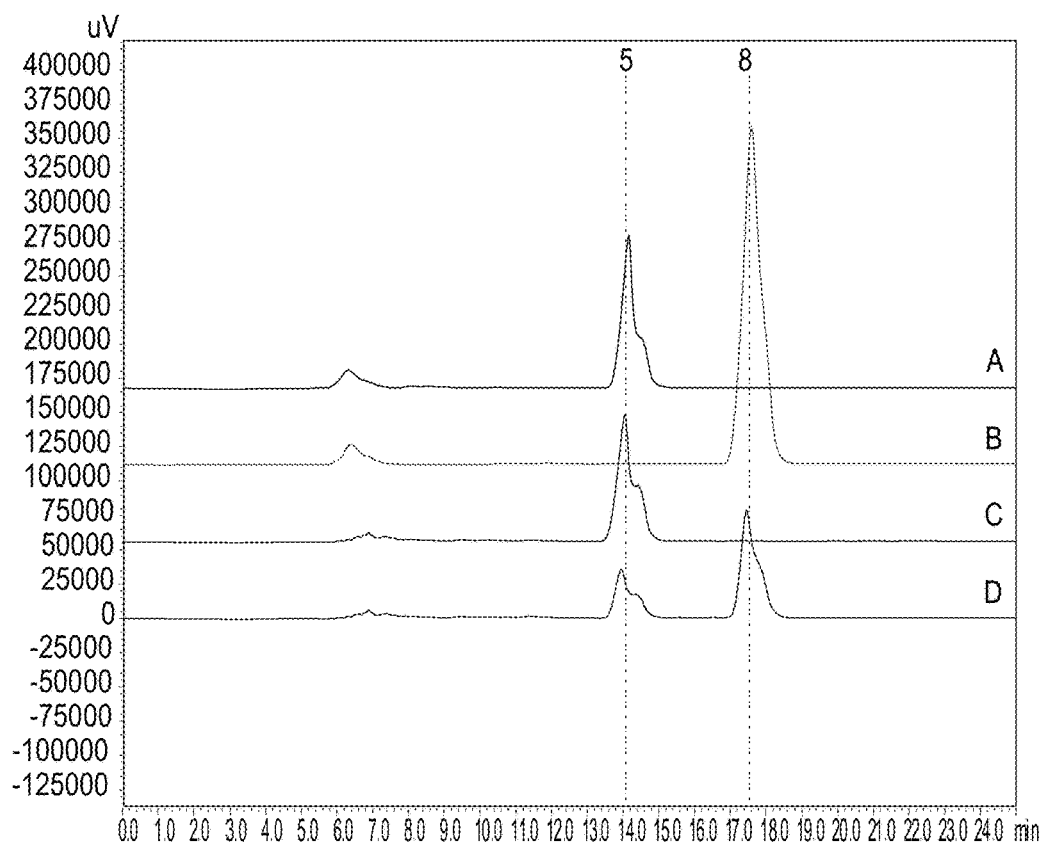
FIG. 19. Chlorination of compounds 5 and 6 to produce compounds 8 and 7. Top (A) standard compound 5, (B) standard compound 8, (C) control compound 5, (D) chlorination reaction of compound 5. Bottom, (A) standard compound 6, (B) standard compound 7, (C) control compound 6, (D) chlorination reaction of compound 6, (E) chlorination reaction of compound 2 to produce compound 1 standard.
Figure 19:
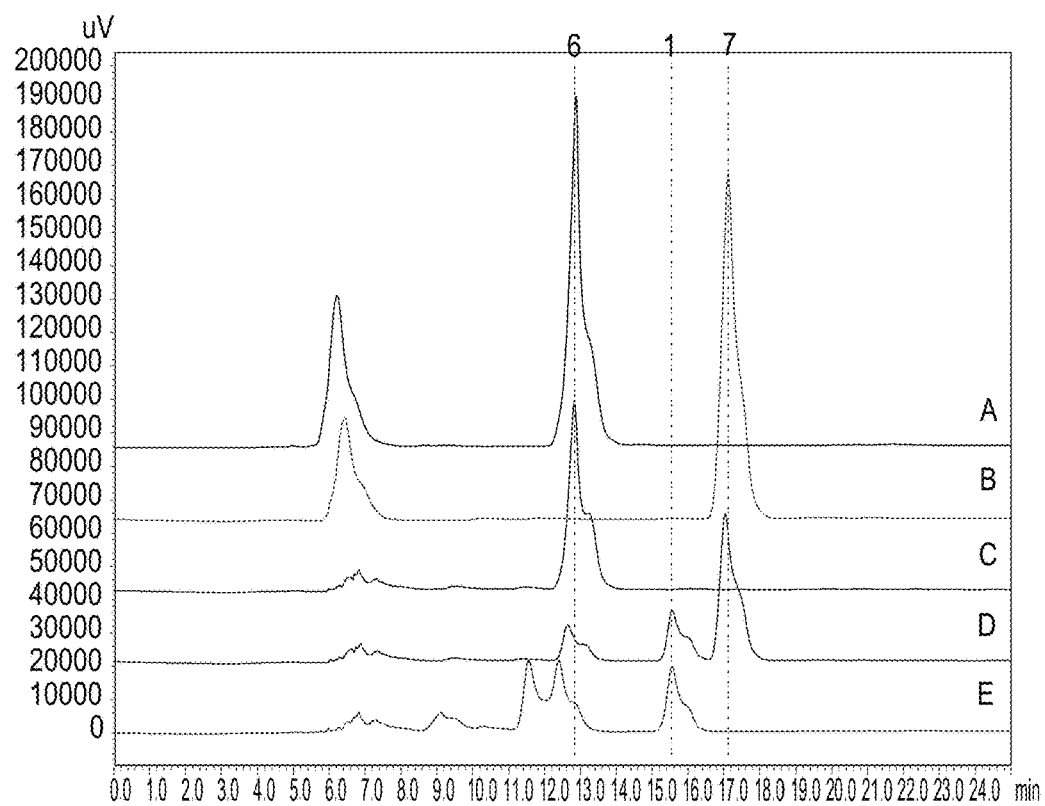

Development of MalA Halogenase as a Biocatalyst for Late-Stage C—H Funtionalization The malbrancheamides are complex hexacyclic fungal indole alkaloids with biological activity as calmodulin antagonists, and the halogenation of the indole ring significantly contributes to the potency of the molecules. MalA has been characterized as an iterative late-stage halogenase that provides the halogen moieties to produce brominated and chlorinated malbrancheamide analogs. Experimental investigation into the mechanism of halogenation has identified a serine residue within the active site as pivotal to catalysis of halogenation. This knowledge base has been used to engineer a range of MalA variants for selective halogenation on the natural substrate premalbrancheamide. Structural and computational analyses of the mutants has aided in determining a mechanism for modulating the selectivity of the chlorination reaction. The substrate scope of the MalA-catalyzed reaction has been analyzed by screening 1,000 computationally predicted substrates. The experimental work disclosed herein has led to the identification of MalA variants, i.e., the C9-selective mutants MalA G131S and S129A/I493S, and the C8-selective mutant MalA S129A/P85S. See FIG. 15. Crystal structures of the wild-type enzyme compared to variants have aided the visualization of how these mutations change the binding pocket and provide insight into the accommodation of unnatural substrates.

REFERENCES (1) Weichold, V.; Milbredt, D.; van Pee, K.-H. Angew. Chem. Int. Ed. 2016, 55, 2-18.
(2) Dong, C.; Flecks, S.; Unversucht, S.; Haupt, C.; van-Pee, K-H.; Naismith, J. H. Science. 2005, 309, 2216-2219.
(3) Yeh, E.; Blasiak, L. C.; Koglin, A.; Drennan, C. L.; Walsh, C. T. Biochemistry. 2007, 46(5), 1284-1292.
(4) Zeng, J.; Zhan, J. ChemBioChem. 2010, 11, 2119-2123.
(5) Ferrara, M.; Perrone, G.; Gambacorta, L.; Epifani, F.; Solfrizzo, M.; Gallo, A. Appl. Environ. Microbiol. 2016, 82(18), 5631-5641.
(6) Neumann, C. S.; Walsh, C. T.; Kay, R. R. Proc. Natl. Acad. Sci. U.S.A 2010, 107(13), 5798-803.
(7) Nielsen, M. T.; Nielsen, J. B.; Anyaogu, D. C.; Holm, D. K.; Nielsen, K. F.; Larsen, T. O.; Mortensen, U. H. PLoS One. 2013, 8(8), 1-10.
(8) Chankhamjon, P.; Boettger-Schmidt, D.; Scherlach, K.; Urbansky, B.; Lackner, G.; Kalb, D.; Dahse, H.-M.; Hoffmeister, D.; Hertweck, C. Angew. Chem. Int. Ed. 2014, 53, 13409-13413.
(9) Sato, M.; Winter, J. M.; Kishimoto, S.; Noguchi, H.; Tang, Y.; Watanabe, K. Org. Lett. 2016, 18, 1446-1449.
(10) Chankhamjon, P.; Tsunematsu, Y.; Ishida-Ito, M.; Sasa, Y.; Meyer, F.; Boettger-Schmidt, D.; Urbansky, B.; Menzel, K.-D.; Scherlach, K.; Watanabe, K.; Hertweck, C. Angew. Chem. Int. Ed. 2016, 55, 11955-11959.
(11) Cacho, R. A.; Chooi, Y.-H.; Zhou, H.; Tang, Y. ACS Chem. Biol. 2013, 8, 2322-2330.
(12) Menon, B. R. K.; Brandenburger, E.; Sharif, H. H.; Klemstein, U.; Shepherd, S. A.; Greaney, M. F.; Micklefield, J. Angew. Chem. Int. Ed. 2017, 10.1002/anie.201706342.
(13) Yeh, E.; Garneau, S.; Walsh, C. T. Proc. Natl. Acad. Sci. U.S.A 2005, 102(11), 3960-3965.
(14) Seibold, C.; Schnerr, H.; Rumpf, J.; Kunzendorf, A.; Hatscher, C.; Wage, T.; Ernyei, A. J.; Dong, C.; Naismith, J. H.; Van Pee, K.-H. Biocatal. Biotransform. 2006, 24(6), 401-408.
(15) Zehner, S.; Kotzsch, A.; Bister, B.; Süssmuth, R. D.; Méndez, C.; Salas, J. A.; van Pee, K-H. Chem. Biol. 2005, 12, 445-452.
(16) Dorrestein, P. C.; Yeh, E.; Garneau-Tsodikova, S.; Kelleher, N. L.; Walsh, C. T. Proc. Natl. Acad. Sci. U.S.A 2005, 102(39), 13843-13848.
(17) El Gamal, A.; Agarwal, V.; Diethelm, S.; Rahman, I.; Schorn, M. A.; Sneed, J. M.; Louie, G. V.; Whalen, K. E.; Mincer, T. J.; Noel, J. P.; Paul, V. J.; Moore, B. S. Proc. Natl. Acad. Sci. U.S.A. 2016, 113(14), 3797-3802.
(18) Martinez-Luis, S.; Rodriguez, R.; Acevedo, L.; Gonzalez, M. C.; Lira-Rocha, A.; Mata, R. Tetrahedron. 2006, 62, 1817-1822.
(19) Watts, K. R.; Loveridge, S. T.; Tenney, K.; Media, J.; Valeriote, F. A.; Crews, P. J. Org. Chem. 2011, 76(15), 6201-6208.
(20) Figueroa, M.; Gonzalez-Andrade, M.; Sosa-Peinado, A.; Madariaga-Mazon, A.; Del Rio-Portilla, F.; Del Carmen Gonzalez, M.; Mata, R. J. Enzyme Inhib. Med. Chem. 2011, 26(3): 378-385.
(21) Madariaga-Mazon, A.; Hernandez-Abreu, O.; Estrada-Soto, S.; Mata, R. J. Pharm. Pharmacol. 2015, 67(4), 551-558.
(22) Klas, K.; Tsukamoto, S.; Sherman, D. H.; Williams, R. M.; J. Org. Chem. 2015, 80, 11672-11685.
(23) Stocking, E. M.; Williams, R. M.; Angew. Chem. Int. Ed. 2003, 42, 3078-3115.
(24) Finefield, J. M.; Frisvad, J. C.; Sherman, D. H.; Williams, R. M. J. Nat. Prod. 2012, 75, 812-833.
(25) Ding, Y.; Greshock, T. J.; Miller, K. A.; Sherman, D. H.; Williams, R. M. Org. Lett. 2008, 10(21), 4863-4866.
(26) Li, S.; Krithika, S.; Tran, H.; Yu, F.; Finefield, J. M.; Sunderhaus, J. D.; McAfoos, T. J.; Tsukamoto, S.; Williams, R. M.; Sherman, D. H. MedChemComm. 2012, 3, 987-996.
(27) Zeng, J.; Zhan, J. Biotechnol. Lett. 2011, 33, 1607-1613.
(28) Buedenbender, S.; Rachid, S.; Müller, R.; Schulz, G. E. J. Mol. Biol. 2009, 385(2), 520-530.
(29) Podzelinska, K.; Latimer, R.; Bhattacharya, A.; Vining, L. C.; Zechel, D. L.; Jia, Z. J. Mol. Biol. 2010, 397, 316-331.
(30) Hillwig, M. L.; Liu, X. Nat. Chem. Biol. 2014, 10, 921-923.
(31) Gutekunst, W. R.; Baran, P. S. Chem. Soc. Rev. 2011, 40, 1976-1991.
(32) Chung, W.; Vanderwal, C. D. Angew. Chem. Int. Ed. 2016, 55, 4396-4434.
(33) Lang, A.; Polnick, S.; Nicke, T.; William, P.; Patallo, E. P.; Naismith, J. H.; van Pee, K.-H. Angew. Chem. Int. Ed. 2011, 50, 2951-2953.
(34) Glenn, W. S.; Nims, E.; O'Connor, S. E. J. Am. Chem. Soc. 2011, 133, 19346-19349.
(35) Shepherd, S. A.; Karthikeyan, C.; Latham, J.; Struck, A.-W.; Thompson, M. L.; Menon, B. R. K.; Styles, M. Q.; Levy, C.; Leys, D.; Micklefield, J. Chem. Sci. 2015, 6, 3454-3460.
(36) Shepherd, S. A.; Menon, B. R. K.; Fisk, H.; Struck, A.-W.; Levy, C.; Leys, D.; Micklefield, J. ChemBioChem. 2016, 17, 821-824.
(37) Payne, J. T.; Andorfer, M. C.; Lewis, J. C. Angew. Chem. Int. Ed. 2013, 52, 5271-5274.
(38) Payne, J. T.; Poor, C. B.; Lewis, J. C. Angew. Chem. Int. Ed. 2015, 54, 4226-4230.
(39) Andorfer, M. C.; Park, H. J.; Vergara-Coll, J.; Lewis, J. C. Chem. Sci. 2016, 7, 3720.
(40) MegAlign Pro®. Version 12.0. DNASTAR. Madison, Wis.

All publications and patents mentioned in the application are herein incorporated by reference in their entireties or in relevant part, as would be apparent from context. Various modifications and variations of the disclosed subject matter will be apparent to those skilled in the art without departing from the scope and spirit of the disclosure. Although the disclosure has been described in connection with specific preferred embodiments, it should be understood that the invention as claimed should not be unduly limited to such specific embodiments. Indeed, various modifications of the described modes for making or using the disclosed subject matter that are obvious to those skilled in the relevant field(s) are intended to be within the scope of the following claims.

What is claimed is:

1. A flavin-dependent halogenase (FDH) variant comprising one or two amino acid substitutions compared to the amino acid sequence set forth in SEQ ID NO:2 or SEQ ID NO:4, wherein the FDH variant comprises the sequence set forth in SEQ ID NO:2 with the one or two amino acid substitutions at position 129, 253, 129/253, 109, 489, 409, 265, 263, 82, 129/131, 131, 129/493, 493, 129/85, and/or 85, or wherein the FDH variant comprises the sequence set forth in SEQ ID NO:4 with the one or two amino acid substitutions at position 494, 253, 129, 129/493, 493, 129/85, 85, 129/131, and/or 131, and wherein the FDH variant is capable of catalyzing the halogenation of a complex organic compound.

2. The flavin-dependent halogenase (FDH) variant of claim 1 wherein the FDH variant comprises the sequence set forth in SEQ ID NO:2 with the one or two amino acid substitutions being S129A, H253F, S129A/H253F, H253A, D109A, F489H, S409A, W265A, W263A, S82A, S129A/G131S, G131S, S129A/I493S, I493S, S129A/P85S, and/or P85S, or wherein the FDH variant comprises the sequence set forth in SEQ ID NO:4 with the one or two amino acid substitutions being E494D, H253F, S129A, S129A/I493S, I493S, S129A/P85S, P85S, S129A/G131S, and/or G131S, and wherein the FDH variant is capable of catalyzing the halogenation of a complex organic compound.

3. The FDH variant of claim 2 wherein the complex organic compound is an aromatic heterocyclic organic compound.

4. The FDH variant of claim 3 wherein the aromatic heterocyclic organic compound comprises a bicyclo[2.2.2]diazaoctane ring.

5. The FDH variant of claim 3 wherein the aromatic heterocyclic organic compound comprises indole.

6. The FDH variant of claim 5 wherein the compound is an indole alkaloid.

7. The FDH variant of claim 6 wherein the indole alkaloid is a prenylated indole alkaloid.

8. The FDH variant of claim 2 wherein the FDH variant is derived from a fungal FDH.

9. The FDH variant of claim 2 wherein the FDH variant is derived from a bacterial FDH.

10. The FDH variant of claim 2 wherein the FDH variant is not derived from a fungal FDH or a bacterial FDH.

11. The FDH variant of claim 2 wherein the FDH variant is a Malbrancheamide A (MalA) halogenase variant.

12. The FDH variant of claim 11 wherein the FDH variant comprises one or two amino acid substitutions of the sequence set forth in SEQ ID NO:2, wherein each substitution is S129A, H253F, S129A/H253F, H253A, D109A, F489H, S409A, W265A, W263A, S82A, S129A/G131S, G131S, S129A/I493S, I493S, S129A/P85S, or P85S.

13. The FDH variant of claim 11 wherein the MalA halogenase comprises the sequence set forth in SEQ ID NO:6, 8, 12, or 16.

14. The FDH variant of claim 2 wherein the FDH variant is a Malbrancheamide A' (MalA') halogenase variant.

15. The FDH variant of claim 13 wherein the FDH variant comprises one or two amino acid substitutions of the sequence set forth in SEQ ID NO:4, wherein each substitution is at position 494, 253, 129, 129/493, 493, 129/85, 85, 129/131, or 131.

16. The FDH variant of claim 15 wherein the FDH variant comprises an amino acid substitution variant of the sequence set forth in SEQ ID NO:4, wherein the substitution is E494D, H253F, S129A, S129A/I493S, I493S, S129A/P85S, P85S, S129A/G131S, or G131S.

17. The FDH variant of claim 14 wherein the MalA' halogenase comprises the sequence set forth in SEQ ID NO:10, 14, or 18.

18. A polynucleotide encoding a FDH variant of claim 2.

19. The polynucleotide of claim 18 wherein the encoded FDH variant is a Malbrancheamide A (MalA) halogenase variant or a Malbrancheamide A' (MalA') halogenase variant.

* * * * *

UNITED STATES PATENT AND TRADEMARK OFFICE
CERTIFICATE OF CORRECTION

PATENT NO. : 11,008,553 B2
APPLICATION NO. : 16/516102
DATED : May 18, 2021
INVENTOR(S) : Sherman et al.

Page 1 of 1

It is certified that error appears in the above-identified patent and that said Letters Patent is hereby corrected as shown below:

In the Claims

At Column 85, Line 1, "5409A," should be -- S409A, --.

At Column 86, Line 9, "(MaIA')" should be -- (MalA') --.

At Column 86, Line 27, "(MaIA')" should be -- (MalA') --.

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*